US009440993B2

(12) United States Patent
Krohn et al.

(10) Patent No.: US 9,440,993 B2
(45) Date of Patent: Sep. 13, 2016

(54) SMALL MOLECULE INHIBITORS OF TRPA1

(75) Inventors: Michael Krohn, Lorsch (DE); Dirk Sombroek, Darmstadt (DE)

(73) Assignee: B.R.A.I.N. Biotechnology Research and Information Network AG, Zwingenberg (DE)

(*) Notice: Subject to any disclaimer, the term of this patent is extended or adjusted under 35 U.S.C. 154(b) by 236 days.

(21) Appl. No.: 14/116,832

(22) PCT Filed: May 11, 2012

(86) PCT No.: PCT/EP2012/058839
§ 371 (c)(1),
(2), (4) Date: Nov. 11, 2013

(87) PCT Pub. No.: WO2012/152940
PCT Pub. Date: Nov. 15, 2012

(65) Prior Publication Data
US 2014/0080842 A1    Mar. 20, 2014

(30) Foreign Application Priority Data

May 12, 2011 (EP) .................................... 11165879

(51) Int. Cl.
| | | |
|---|---|---|
| *C07D 513/04* | (2006.01) | |
| *C07D 249/08* | (2006.01) | |
| *C07C 255/44* | (2006.01) | |
| *C07C 69/78* | (2006.01) | |
| *C07C 62/30* | (2006.01) | |
| *A23L 1/22* | (2006.01) | |
| *A61K 31/235* | (2006.01) | |
| *A61Q 19/00* | (2006.01) | |
| *A61K 8/36* | (2006.01) | |
| *A61K 8/37* | (2006.01) | |
| *A61K 8/49* | (2006.01) | |
| *A61K 8/69* | (2006.01) | |

(52) U.S. Cl.
CPC ......... *C07D 513/04* (2013.01); *A23L 1/22083* (2013.01); *A23L 1/22091* (2013.01); *A61K 8/36* (2013.01); *A61K 8/37* (2013.01); *A61K 8/49* (2013.01); *A61K 8/496* (2013.01); *A61K 8/69* (2013.01); *A61K 31/235* (2013.01); *A61Q 19/00* (2013.01); *C07C 62/30* (2013.01); *C07C 69/78* (2013.01); *C07C 255/44* (2013.01); *C07D 249/08* (2013.01); *A61K 2800/782* (2013.01)

(58) Field of Classification Search
CPC C07D 513/04; C07D 249/08; C07C 255/44; C07C 62/30; C07C 69/78; A61K 8/36; A61K 8/69; A61K 8/37; A61K 8/49; A61K 8/496; A61K 31/235; A61K 2800/782; A23L 1/22083; A23L 1/22091; A61Q 19/00
See application file for complete search history.

(56) References Cited

U.S. PATENT DOCUMENTS

| 4,983,394 A | 1/1991 | Hussein et al. |
|---|---|---|
| 6,623,768 B1 | 9/2003 | Naguib |
| 2003/0143291 A1 | 7/2003 | Naguib |

FOREIGN PATENT DOCUMENTS

| CN | 101607907 A | 12/2009 |
|---|---|---|
| WO | 2004/087179 A1 | 10/2004 |
| WO | 2009/089082 A1 | 7/2009 |
| WO | 2009/089083 A1 | 7/2009 |
| WO | 2010/125469 A1 | 11/2010 |
| WO | 2010/138879 A1 | 12/2010 |
| WO | 2010/141805 A1 | 12/2010 |

OTHER PUBLICATIONS

Zurborg et al., "Direct Activation of the Ion Channel TRPA1 by Ca2+", Nature Neuroscience, vol. 10, No. 3, Mar. 2007, pp. 277-279.
Ross et al., "Pharmacodynamics: Mechanisms of Drug Action and the Relationship between Drug Concentration and Effect", Goodman & Gilman's The Pharmacological Basis of Therapeutics, Chapter 2, 10th Edition, 2001, 15 pages.
International Preliminary Report on Patentability received for PCT Patent Application No. PCT/EP2012/058839, mailed on Nov. 21, 2013, 17 pages.
International Search Report and Written Opinion received for PCT Patent Application No. PCT/EP2012/058839, mailed on Nov. 7, 2012, 23 pages.
Atoyan et al., "Non-Neuronal Expression of Transient Receptor Potential Type A1 (TRPA1) in Human Skin", Journal of Investigative Dermatology, vol. 129, 2009, pp. 2312-2315.
Bandell et al., "Noxious Cold Ion Channel TRPA1 is Activated by Pungent Compounds and Bradykinin", Neuron, vol. 41, Mar. 25, 2004, pp. 849-857.
Baraldi et al., "Transient Receptor Potential Ankyrin 1 (TRPA1) Channel as Emerging Target for Novel Analgesics and Anti-Inflammatory Agents", Journal of Medicinal Chemistry, vol. 53, No. 14, 2010, pp. 5085-5107.

(Continued)

Primary Examiner — Shailendra Kumar
(74) Attorney, Agent, or Firm — Morrison & Foerster LLP

(57) ABSTRACT

The present invention relates to the use of compounds which are capable of attenuating skin irritation when they are applied to the skin. Skin irritation can be caused, inter alia, by ingredients of cosmetic or pharmaceutical compositions and/or environmental irritants. In particular, the present invention relates to compounds having the property of antagonizing the activation of the transient receptor potential (TRP) ankyrin 1 (TRPA1) ion channel and the use of said compounds as soothing agents. Such compounds can be used in many fields, particularly in personal-care products, cosmetics, textile and packaging products, pharmaceutical compositions, medical devices, and foodstuffs. The present invention further relates to products and/or pharmaceutical compositions containing said compounds. The present invention also relates to the use of the compounds described herein for the modulation of the taste of a food product.

29 Claims, 10 Drawing Sheets

(56) References Cited

OTHER PUBLICATIONS

Figure 1:
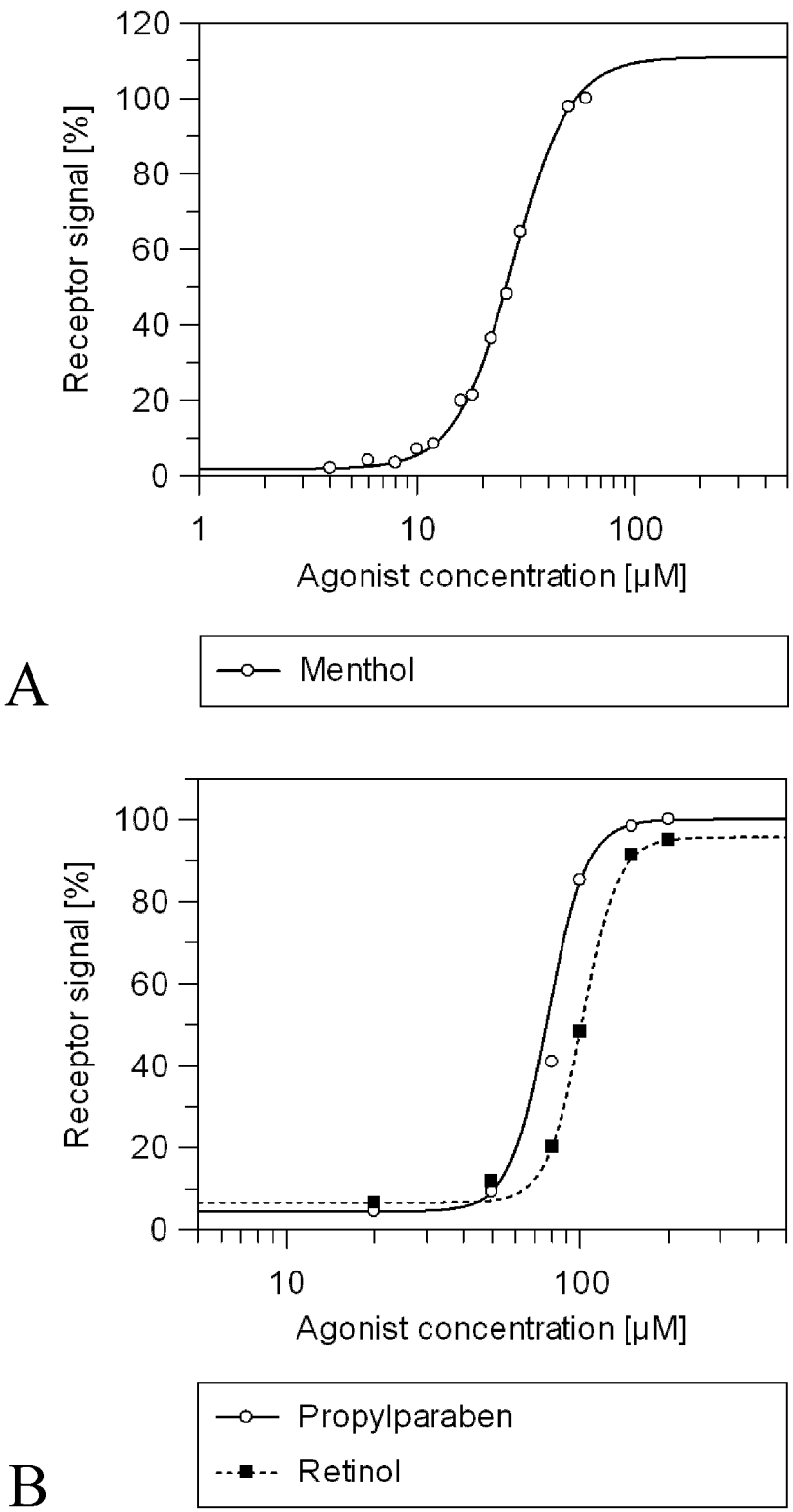

Bautista et al., "Pungent Products from Garlic Activate the Sensory Ion Channel TRPA1", PNAS, vol. 102, No. 34, Aug. 23, 2005, pp. 12248-12252.

Bautista et al., "TRPA1 Mediates the Inflammatory Actions of Environmental Irritants and Proalgesic Agents", Cell, vol. 124, Mar. 24, 2006, pp. 1269-1282.

Behrendt et al., "Characterization of the Mouse Cold-Menthol Receptor TRPM8 and Vanilloid Receptor Type-1 VR1 using a Fluorometric Imaging Plate Reader (FLIPR) Assay", British Journal of Pharmacology, vol. 141, No. 4, 2004, pp. 737-745.

Boukamp et al., "Normal Keratinization in a Spontaneously Immortalized Aneuploid Human Keratinocyte Cell Line", The Journal of Cell Biology, vol. 106, Mar. 1988, pp. 761-771.

Clapham, David E., "SnapShot: Mammalian TRP Channels", Cell, vol. 129, Apr. 6, 2007, pp. 220-220.e1.

Clapham, David E., "TRP Channels as Cellular Sensors", Nature, vol. 426, Dec. 4, 2003, pp. 517-524.

Corey et al., "TRPA1 is a Candidate for the Mechanosensitive Transduction Channel of Vertebrate Hair Cells", Nature, vol. 432, Dec. 9, 2004, pp. 723-730.

da Costa et al., "The Involvement of the Transient Receptor Potential A1 (TRPA1) in the Maintenance of Mechanical and Cold Hyperalgesia in Persistent Inflammation", Pain, vol. 148, 2010, pp. 431-437.

Fanger et al., "TRPA1 as an Analgesic Target", The Open Drug Discovery Journal, vol. 2, 2010, pp. 64-70.

Farage et al., "Sensitive Skin: Closing in on a Physiological Cause", Contact Dermatitis, vol. 62, 2010, pp. 137-149.

Fujita et al., "Methyl p-Hydroxybenzoate Causes Pain Sensation through Activation of TRPA1 Channels", British Journal of Pharmacology, vol. 151, 2007, pp. 134-141.

Gaudet, Rachelle, "TRP Channels Entering the Structural Era", J Physiol, vol. 586.15, 2008, pp. 3565-3575.

Genbank, Accession No. NM_007332.2 , "*Homo sapiens* Transient Receptor Potential Cation Channel, Subfamily A, Member 1 (TRPA1), mRNA", available at www.ncbi.nlm.nih.gov/nuccore/NM_007332, retrieved on Nov. 19, 2013, pp. 1-8.

Genbank, Accession No. NM_024080.4 , "*Homo sapiens* Transient Receptor Potential Cation Channel, Subfamily M, Member 8 (TRPM8), mRNA", available at www.ncbi.nlm.nih.gov/nuccore/NM_024080#sequence_109689694, retrieved on Nov. 19, 2013, pp. 1-7.

Geroushi et al., "Antiinflammatory Sesquiterpenes from the Root Oil of Ferula Hermonis", Phytotherapy Research, vol. 25, 2011, pp. 774-777.

Hinman et al., "TRP Channel Activation by Reversible Covalent Modification", PNAS, vol. 103, No. 51, Dec. 19, 2006, pp. 19564-19568.

Howard et al., "Hypothesis: A Helix of Ankyrin Repeats of the NOMPC-TRP Ion Channel is the Gating Spring of Mechanoreceptors", Current Biology, vol. 14, No. 6, 2004, pp. R224-R226.

Hu et al., "Activation of TRPA1 Channels by Fenamate Non-Steroidal Anti-Inflammatory Drugs", Pflugers Arch., vol. 459, No. 4, Mar. 2010, pp. 579-592.

Jordt et al., "Mustard Oils and Cannabinoids Excite Sensory Nerve Fibres through the TRP Channel ANKTM1", Nature, vol. 427, Jan. 15, 2004, pp. 260-265.

Kang et al., "Analysis of *Drosophila* TRPA1 Reveals an Ancient Origin for Human Chemical Nociception", Nature, vol. 464, No. 7288, Mar. 25, 2010, pp. 597-600.

Karashima et al., "Bimodal Action of Menthol on the Transient Receptor Potential Channel TRPA1", The Journal of Neuroscience, vol. 27, No. 37, Sep. 12, 2007, pp. 9874-9884.

Kremeyer et al., "A Gain-of-Function Mutation in TRPA1 Causes Familial Episodic Pain Syndrome", Neuron, vol. 66, Jun. 10, 2010, pp. 671-680.

Kwan et al., "TRPA1 Modulates Mechanotransduction in Cutaneous Sensory Neurons", The Journal of Neuroscience, vol. 29, No. 15, Apr. 15, 2009, pp. 4808-4819.

Lee et al., "Comparison of Objective and Sensory Skin Irritations of Several Cosmetic Preservatives", Contact Dermatitis, vol. 56, 2007, pp. 131-136.

Lishko et al., "The Ankyrin Repeats of TRPV1 Bind Multiple Ligands and Modulate Channel Sensitivity", Neuron, vol. 54, Jun. 21, 2007, pp. 905-918.

MacPherson et al., "Noxious Compounds Activate TRPA1 Ion Channels through Covalent Modification of Cysteines", Nature Letters, vol. 445, Feb. 1, 2007, pp. 541-545.

MacPherson et al., "The Pungency of Garlic: Activation of TRPA1 and TRPV1 in Response to Allicin", Current Biology, vol. 15, May 24, 2005, pp. 929-934.

McNamara et al., "TRPA1 Mediates Formalin-Induced Pain", PNAS, vol. 104, No. 33, Aug. 14, 2007, pp. 13525-13530.

Nazhimitdinova et al., "Structures of Fersin and Fersinin", Chemistry of Natural Compounds, vol. 30, No. 4, 1994, pp. 464-465.

Nihei et al., "Molecular Design of Multifunctional Food Additives: Antioxidative Antifungal Agents", Journal of Agricultural and Food Chemistry, vol. 52, No. 16, 2004, pp. 5011-5020.

Petrus et al., "A Role of TRPA1 in Mechanical Hyperalgesia is Revealed by Pharmacological Inhibition", Molecular Pain, vol. 3, 2007, 8 pages.

Ramsey et al., "An Introduction to TRP Channels", Annual Review of Physiology, vol. 68, 2006, pp. 619-647.

Rassouli et al., "Investigating the Cytotoxic and Apoptosis Inducing Effects of Monoterpenoid Stylosin in vitro", Fitoterapia, vol. 82, 2011, pp. 742-749.

Rasulev et al., "Molecular Modelling and QSAR Analysis of the Estrogenic Activity of Terpenoids Isolated from Ferula Plants", SAR and QSAR in Environmental Research, vol. 18, Nos. 7-8, Oct.-Dec. 2007, pp. 663-673.

Sone et al., "Pharmacological Studies of Stinging Caused by Parabens", Journal of Japanese Cosmetic Science Society, vol. 14, 1990, pp. 8-16. (English abstract only).

Sotomayor et al., "In Search of the Hair-Cell Gating Spring: Elastic Properties of Ankyrin and Cadherin Repeats", Structure, vol. 13, Apr. 2005, pp. 669-682.

Story et al., "ANKTM1, a TRP-like Channel Expressed in Nociceptive Neurons, is Activated by Cold Temperatures", Cell, vol. 112, Mar. 21, 2003, pp. 819-829.

Taylor-Clark et al., "Prostaglandin-Induced Activation of Nociceptive Neurons via Direct Interaction with Transient Receptor Potential A1 (TRPA1)", Molecular Pharmacology, vol. 73, No. 2, 2008, pp. 274-281.

Trevisani et al., "4-Hydroxynonenal, an Endogenous Aldehyde, Causes Pain and Neurogenic Inflammation through Activation of the Irritant Receptor TRPA1", PNAS, vol. 104, No. 33, Aug. 14, 2007., pp. 13519-13524.

Wang et al., "The Nociceptor Ion Channel TRPA1 is Potentiated and Inactivated by Permeating Calcium Ions", The Journal of Biological Chemistry, vol. 283, No. 47, Nov. 21, 2008, pp. 32691-32703.

Wang et al., "TRPA1 is a Component of the Nociceptive Response to CO2", The Journal of Neuroscience, vol. 30, No. 39, Sep. 29, 2010, pp. 12958-12963.

Wei et al., "Attenuation of Mechanical Hypersensitivity by an Antagonist of the TRPA1 Ion Channel in Diabetic Animals", Anesthesiology, vol. 111, No. 1, Jul. 2009, pp. 147-154.

Wei et al., "Spinal Transient Receptor Potential Ankyrin 1 Channel Contributes to Central Pain Hypersensitivity in Various Pathophysiological Conditions in the Rat", Pain, vol. 152, 2011, pp. 582-591.

Worm et al., "Discovery of N-(3-(Morpholinomethyl)-Phenyl)-Amides as Potent and Selective CB2 Agonists", Bioorganic & Medicinal Chemistry Letters, vol. 19, 2009, pp. 5004-5008.

Wu et al., "International Union of Basic and Clinical Pharmacology. LXXVI. Current Progress in the Mammalian TRP Ion Channel Family", Pharmacological Reviews, vol. 62, No. 3, 2010, pp. 381-404.

SMALL MOLECULE INHIBITORS OF TRPA1

CROSS REFERENCE TO RELATED APPLICATIONS

This is a U.S. National Phase patent application of PCT/EP2012/058839, filed May 11, 2012, which claims priority to EP Patent Application No. 11165879.5, filed May 12, 2011, each of which is hereby incorporated by reference in the present disclosure in its entirety.

SUBJECT OF THE INVENTION

The present invention relates to the use of compounds which are capable of attenuating skin irritation when they are applied to the skin. Skin irritation can be caused, inter alia, by ingredients of cosmetic or pharmaceutical compositions and/or environmental irritants. In particular, the present invention relates to compounds having the property of antagonizing the activation of the transient receptor potential (TRP) ankyrin 1 (TRPA1) ion channel and the use of said compounds as soothing agents. Such compounds can be used in many fields, particularly in personal-care products, cosmetics, textile and packaging products, pharmaceutical compositions, medical devices, and foodstuffs. The present invention further relates to products and/or pharmaceutical compositions containing said compounds. The present invention also relates to the use of the compounds described herein for the modulation of the taste of a food product.

BACKGROUND OF THE INVENTION

TRPA1 (formerly known as ANKTM1) (Story, 2003) belongs to the family of the transient receptor potential channels (TRP ion channels). In mammals this family consists of 28 different proteins grouped into six subfamilies by means of amino acid sequence homology: TRPC (canonical, seven members), TRPM (melastatin, eight members), TRPV (vanilloid, six members), TRPA (ankyrin, one member), TRPML (mucolipin, three members), and TRPP (polycystin, three members) (Ramsey, 2006; Clapham, 2007; Wu, 2010). The TRP proteins are composed of six putative transmembrane domains, a pore-forming loop between the fifth and sixth domain, and intracellularly located N- and C-termini (Gaudet, 2008). They apparently all assemble as tetramers to establish ion channels that mediate the flux of cations, especially $Na^+$ and $Ca^{2+}$, across membranes. Typically, activation of these channels leads to depolarization and initiates a multitude of cellular responses (Clapham, 2003).

TRPA1 is the only mammalian member of the "ankyrin" subfamily. The protein contains a high number of ankyrin repeats (at least 14) in its N-terminus. These are supposed to interact with the cytoskeleton or to modulate ligand binding (Howard and Bechsted, 2004; Sotomayor, 2005; Lishko, 2007). The channel is expressed in subpopulations of dorsal root, trigeminal, and nodose ganglia neurons, especially in C- and Ad-fibers of the pain pathway, were it plays an important role in nociception, neurogenic inflammation, and skin hypersensitivity (Story, 2003; Jordt, 2004, Bautista, 2006). In addition, TRPA1 is expressed in hair cells of the inner ear, endothelial and epithelial cells (Corey, 2004; Atoyan, 2009; Kwan, 2009)

TRPA1 responds to a wide variety of stimuli. For instance, it is activated by a multitude of exogenous and endogenous chemicals. Many of these chemicals are highly reactive electrophiles that form covalent adducts with intracellular cysteine residues of TRPA1 (Hinman, 2006; Macpherson, 2007). They are structurally quite diverse, including cinnamaldehyde, allicin and allyl isothiocyanate (the main pungent ingredients of cinnamon, garlic and mustard oil, respectively), environmental irritants such as acrolein, and endogenous compounds like 4-hydroxynonenal or certain prostaglandins (Bandell, 2004; Jordt, 2004; Bautista, 2005; Macpherson, 2005; Trevisani, 2007; Taylor-Clark, 2008). In its role as a sensor for reactive and therefore potentially harmful chemicals it is conserved from flies to men (Kang, 2010). However, TRPA1 is also activated by some more "classical" (lock and key) ligands, e.g. menthol and p-hydroxybenzoic acid esters, the so-called parabens (Karashima, 2007; Fujita, 2007).

Moreover, TRPA1 is activated downstream of certain G protein-coupled receptors (in a receptor-operated manner), by an increase in intracellular calcium, and through intracellular acidification (Zurborg, 2007; Wang, 2008; Wang, 2010). Further, it is proposed to be activated by noxious cold (<17° C.) and therefore presumably involved in thermosensation. Additional studies point to a role for TRPA1 in the mechanisms of mechanical and cold hypersensitivity produced by skin irritation or inflammation (Bautista, 2006; Petrus, 2007; da Costa, 2010; Wei, 2011).

Just recently a TRPA1-associated channelopathy was reported (Kremeyer, 2010). A gain-of-function mutation in the fourth transmembrane domain leads to a familial episodic pain syndrome. This report further strengthens the relevance of the channel in human pain signalling pathways.

Certain substances of cosmetic and/or pharmaceutical compositions can cause skin irritation if they are applied to the skin, especially the face. This may lead to unpleasant sensations like stinging, burning, and itching, especially in persons with sensitive skin. It is known that these nociceptive sensations are at least to a certain extent mediated by TRPA1. Examples of such substances in cosmetic compositions are emulsifiers, detergents, preservatives, anti-aging compounds, depilation agents, and peeling agents such as α-hydroxy acids. Preservatives such parabens are known triggers of skin irritation (Sone, 1990; Lee, 2007). In particular, Fujita et al. (2007) reported that parabens cause pain sensation through activation of TRPA1. Furthermore, the skin as a barrier of the organism is permanently affected by environmental factors such as ultraviolet (UV) radiation, extreme temperature, and weather conditions or polluting emissions.

Sensitive skin is a complex phenomenon because it is a heterogeneous and self-diagnosed medical condition (often occurring without measurable signs of skin inflammation). Consumers claiming that they have sensitive skin are a growing problem for the cosmetic as well as the pharmaceutical industry. Symptoms like stinging, burning, and itching may lead to dissatisfaction and thereby influence life quality and consumer preferences (Farage and Maibach, 2010). Increasing rates and accumulating reports of sensitive skin give rise to a constant need for new desensitizing (soothing) agents. It is reasonable to assume that up to 50% of people living in the industrial nations possess sensitive skin.

Numerous skin irritation-reducing compounds are established in the technical field referred to, but researchers are constantly looking for alternatives. Known inhibitors of TRPA1 include AP-18 (Petrus, 2007), HC-030031 (McNamara, 2007) and the related compounds A-967079 (WO 2009/089082) and CHEM-5861528 (Wei, 2009). Numerous other TRPA1 antagonists have been described in following exemplary patent applications: WO 2009/089083 (filed by Abbott Laboratories), WO 2010/141805 (Janssen Pharmaceutica), WO 2010/138879 (Hydra Biosciences), and WO 2010/125469 (Glenmark Pharmaceuticals).

Some of the above-mentioned compounds exhibit antagonist activity at TRPA1 at least to some extent, but may be insufficient and unsatisfactory in the retainability of the inhibitory effect. Furthermore, some of the TRPA1 antagonists/inhibitors known in the art may be insufficient with regard to their efficacy, their duration of action, their scent, their taste, their selectivity, their solubility, and/or their volatility. Accordingly, there is a need for TRPA1 antagonists/inhibitors that may overcome one or more of these drawbacks. Furthermore, several studies using TRPA1 inhibitors demonstrated a potential role of TRPA1 in the treatment of pain and analgesia. Hence, there is a strong demand in the art for providing alternative TRPA1 antagonists/inhibitors that can be used as soothing agents.

OBJECT AND SUMMARY OF THE INVENTION

It is an object of the invention to provide compounds that modulate the TRPA1 channel activity. In certain embodiments of the invention, such compounds exhibit antagonist activity at the TRPA1 channel. In certain embodiments of the invention, such compounds exhibit partial antagonist activity at the TRPA1 channel. In certain embodiments of the invention, such compounds exhibit selective antagonist activity at the TRPA1 channel. It is an objective of the invention to provide compounds that antagonize the functional modulation of the TRPA1 ion channel. In certain embodiments of the invention, such compounds act as partial or full TRPA1 antagonists by blocking channel activation.

In certain embodiments of the invention, compounds according to the invention exhibit activity for antagonizing or inhibiting TRPA1 in a lower concentration range than needed for antagonizing or inhibiting other ion channels and/or receptor proteins. In another embodiment, a compound of the invention acts as a TRPA1 antagonist, but not as a TRPM8 antagonist. In another embodiment, a compound of the invention acts as a TRPA1 partial antagonist, but not as a TRPM8 antagonist. In certain embodiments of the invention, such compounds act as TRPA1 antagonists/inhibitors without substantially modulating other ion channels and/or receptor proteins.

It is a further objective of the invention to provide compounds that attenuate skin irritation caused, inter alia, by ingredients of personal-care products, pharmaceutical compositions, textile products, medical devices, packaging products, or food products, and in particular of cosmetic or pharmaceutical compositions, and/or environmental irritants. In this context it is the objective to provide compounds that are usable as soothing agents. It is a further objective of the invention to provide compounds that selectively modulate the TRPA1 ion channel.

It is a further objective of the invention to provide compositions comprising said compounds that exhibit soothing effects when they are applied to the skin. It is a further objective to provide personal-care products, pharmaceutical compositions, textile products, packaging products, or food products comprising said compounds. Also, the object of the invention is to provide soothing agent compositions comprising one or more of said compounds.

Another object of the invention is to provide a compound which can be used to modulate the taste of a food product.

These objectives as well as others which will become apparent from the ensuing description are attained by the subject matter of the independent claims. Some of the embodiments of the present invention are defined by the subject matter of the dependent claims.

According to one embodiment, the present invention relates to a product comprising a compound that exhibits antagonist activity at TRPA1, and wherein the product is selected from the group consisting of a personal-care product, a pharmaceutical composition, a textile product, a medical device, a packaging product, and a food product.

In an optional embodiment, the compound exhibits selective antagonist activity at TRPA1.

In a further optional embodiment, the antagonist activity at TRPA1 is at least three times, at least five times, or even at least ten times greater than the antagonist activity of the compound at a different ion channel and/or receptor.

According to an optional embodiment, in a functional cell based assay the compound inhibits an increase in intracellular calcium concentration in human cells recombinantly expressing human TRPA1 at least three times, at least five times, or even at least ten times more efficient than that of human cells recombinantly expressing a different human ion channel and/or receptor.

Optionally, the other human ion channel and/or receptor is TRPM8 or TRPV1.

In a further optional embodiment, the compound is selected from the group consisting of Compounds I.2, I2.1, II.2, III.2, IV.2, and V.2, wherein the compounds have the general formulas as defined herein below.

In a further optional embodiment, the compound is selected from the group consisting of compounds I.3, II.3, III.3, IV.3, and V.3, the compounds having the following chemical structures:

| Compound | Chemical structure |
|---|---|
| I.3 | (structure shown) |
| II.3 | (structure shown) |
| III.3 | (structure shown) |

| Compound | Chemical structure |
|---|---|
| IV.3 | [structure: pyrrolidine-N-C(=O)-CH2- connected to thiadiazolopyrimidinone core with =CH-(2,5-dimethylpyrrole-N-(3-chlorophenyl)) substituent] |
| V.3 | [structure: dehydroabietic acid-like tricyclic terpenoid with isopropyl group, CH3 groups, and COOH] |

A further embodiment of the invention relates to a use of a compound as defined in any of claims 1 to 7 or herein below in a product selected from the group consisting of a personal-care product, a pharmaceutical composition, a medical device, a textile product, a packaging product, and a food product.

Optionally, the personal-care product is selected from the group consisting of a cosmetic product, a wound dressing and a hygiene product.

Optionally, the pharmaceutical composition is selected from the group consisting of medicaments for the treatment of pain.

A further embodiment of the invention relates to a compound as defined in any of claims 1 to 7 or herein below for use in therapy.

A further embodiment of the invention relates to a compound as defined in any of claims 1 to 7 or herein below for use in the treatment of pain.

Another embodiment of the invention relates to the product of any of claims 1 to 7 or as defined herein or the use of claim 8 or as defined herein, wherein the food product is selected from the group consisting of beverages or edibles.

Optionally, said beverages are selected from wine, coffee, fruit juices or tea.

Optionally, said edibles are selected from bakery and dairy products, products based on fruit or vegetables, convenience meals, sweets or snack foods.

A further embodiment of the invention relates to the product of any of claims 1 to 7 and 13 or as defined herein or the use of claim 8 or 13 or as defined herein, wherein the food product further comprises one or more ingredient(s) with a strong, pungent and/or astringent taste.

Another embodiment of the invention relates to the use of a compound as defined in any of claims 1 to 7 or as defined herein for the modulation of the taste of a food product.

A further embodiment of the invention relates to a cosmetic use of a compound as defined in any of claims 1 to 7 or herein below as soothing agent.

A further embodiment of the invention relates to an in vitro method of inhibiting TRPA1, wherein TRPA1 is contacted with a compound as defined in any of claims 1 to 7 or herein below.

FIGURE LEGENDS

The accompanying drawings, which are incorporated and form part of the specification, merely illustrate certain embodiments of the present invention. They are meant to serve to explain specific modes of the present invention to those of skilled in the art. In the drawings:

FIG. 1: Dose-response curves of TRPA1 agonists (calcium assay). Exemplary dose-response curves are shown. Agonistic efficacy of menthol ($EC_{80}$=35 µM), propylparaben ($EC_{80}$=80 µM), and retinol ($EC_{80}$=150 µM) was measured in a cell-based calcium assay system.
A: Agonistic activity of menthol at TRPA1.
B: Agonistic activity of propylparaben and retinol at TRPA1.

Figure 2:
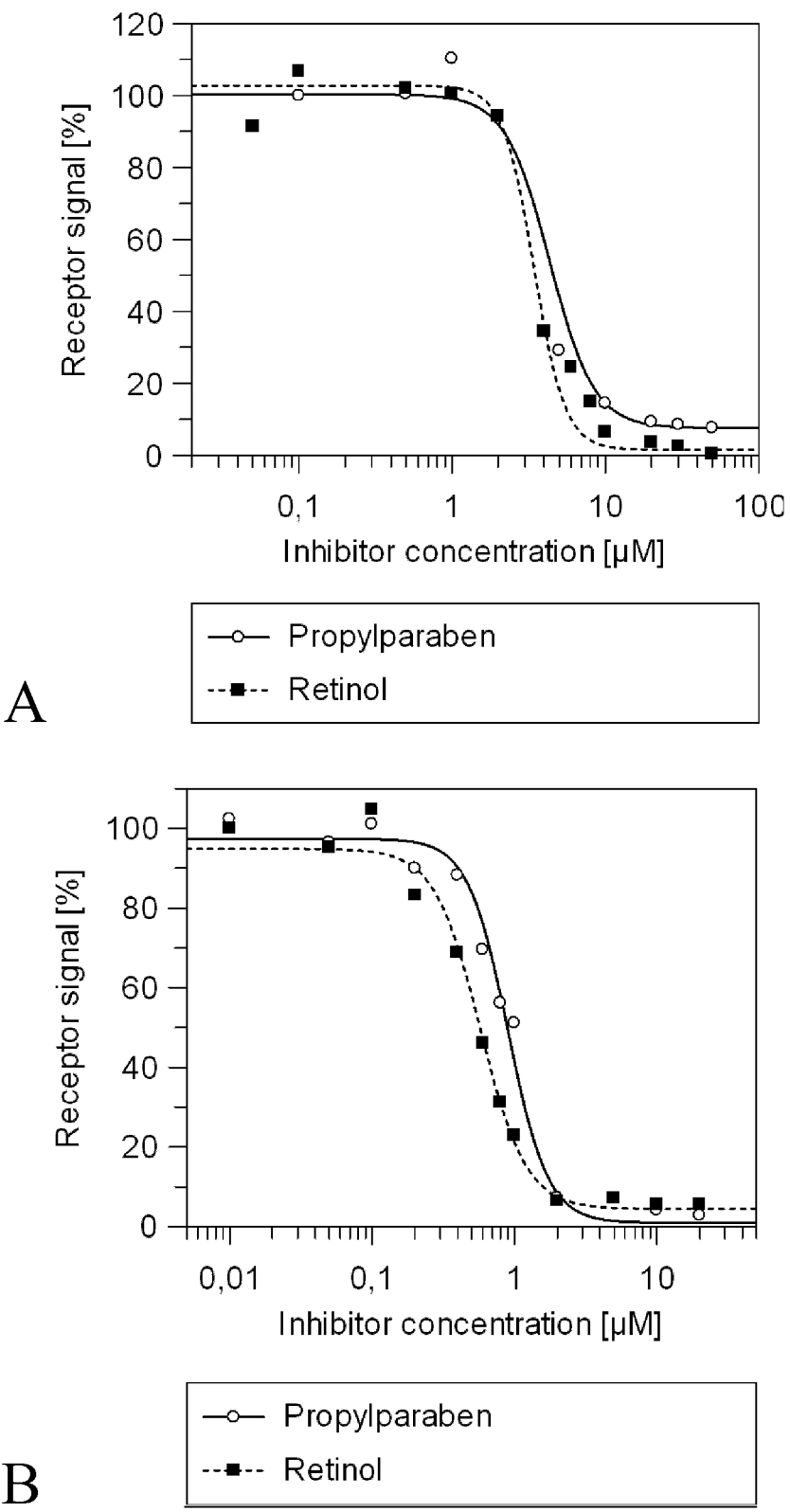

FIG. 2: Dose-response curves of TRPA1 antagonists (calcium assay). Exemplary dose-response curves are shown. Antagonistic efficacy of compound I.3 and II.3 against propylparaben and retinol (at their corresponding $EC_{80}$ concentrations) was measured in a cell-based calcium assay system.
A: Antagonistic activity of compound I.3 at TRPA1 against retinol and propylparaben.
B: Antagonistic activity of compound II.3 at TRPA1 against retinol and propylparaben.

Figure 3:
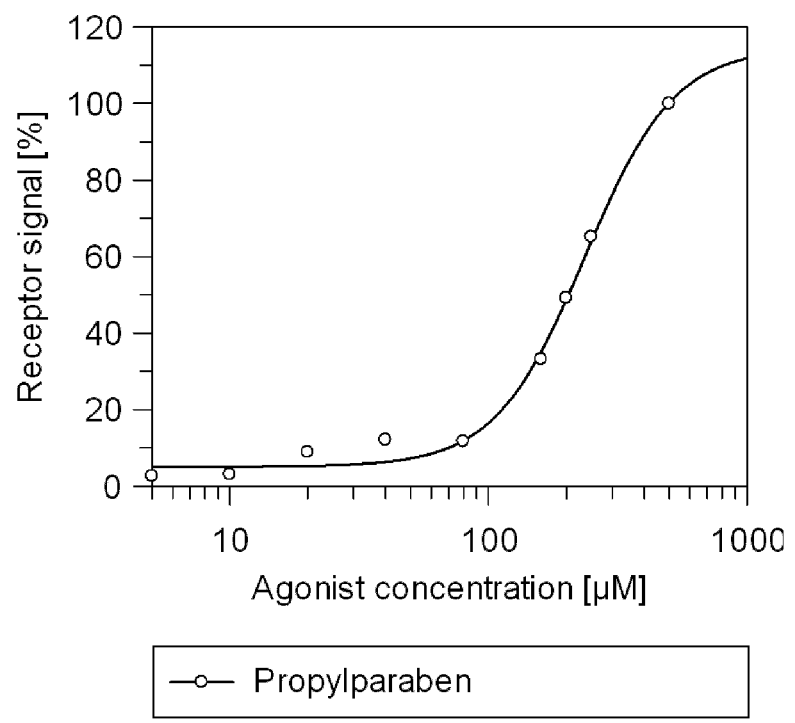

FIG. 3: Dose-response curve of a TRPA1 agonist (impedance assay). An exemplary dose-response curve is shown. Agonistic efficacy of propylparaben ($EC_{80}$=200 µM) was measured in a cell-based impedance assay system. FIG. 3 depicts the agonistic activity of propylparaben at TRPA1.

Figure 4:
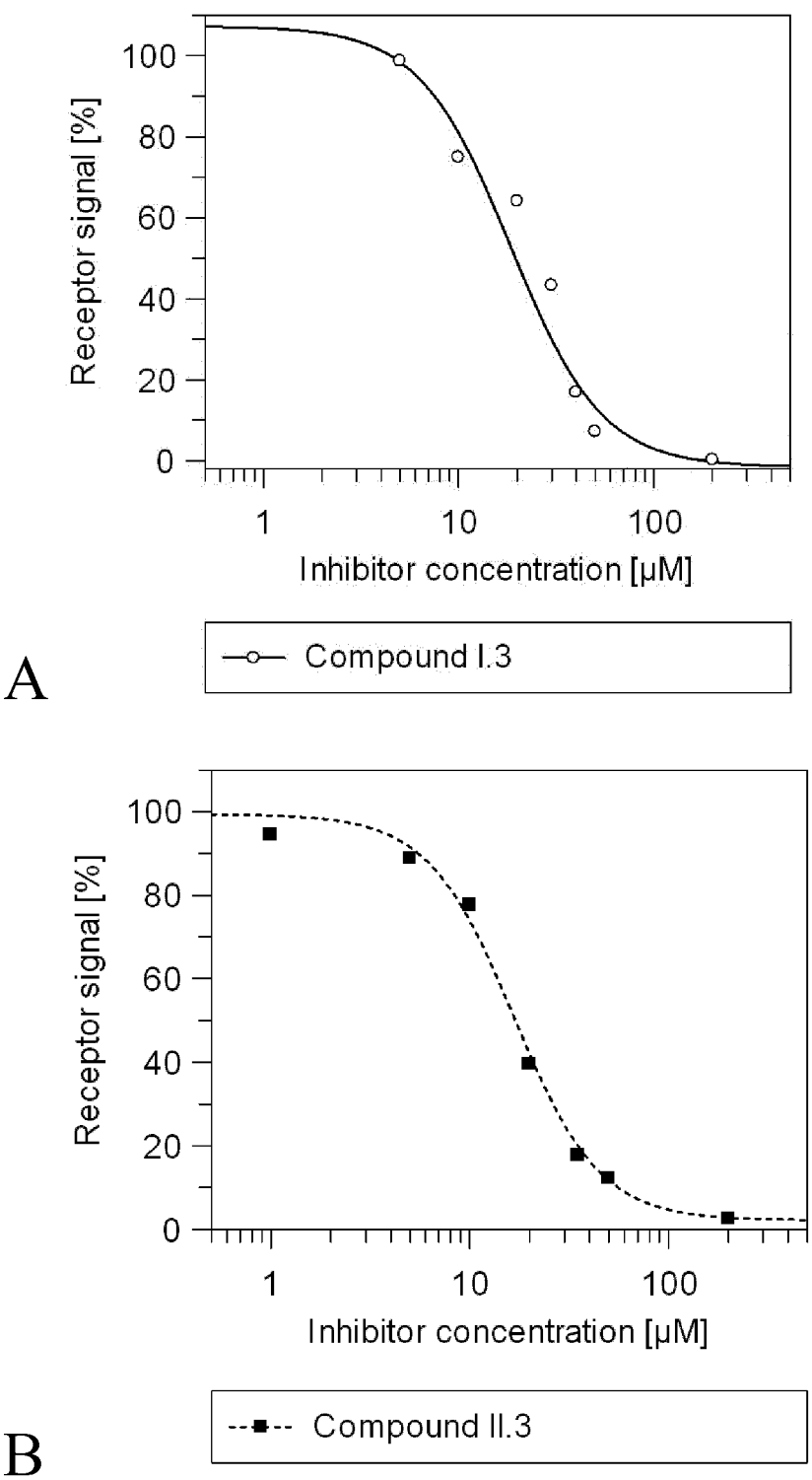

FIG. 4: Dose-response curves of TRPA1 antagonists (impedance assay). Exemplary dose-response curves are shown. Antagonistic efficacy of compound I.3 and II.3 against retinol and propylparaben (at their corresponding $EC_{80}$ concentrations) was measured in a cell-based impedance assay system.
A: Antagonistic activity of compound I.3 at TRPA1 against retinol.
B: Antagonistic activity of compound II.3 at TRPA1 against propylparaben.

Figure 5:
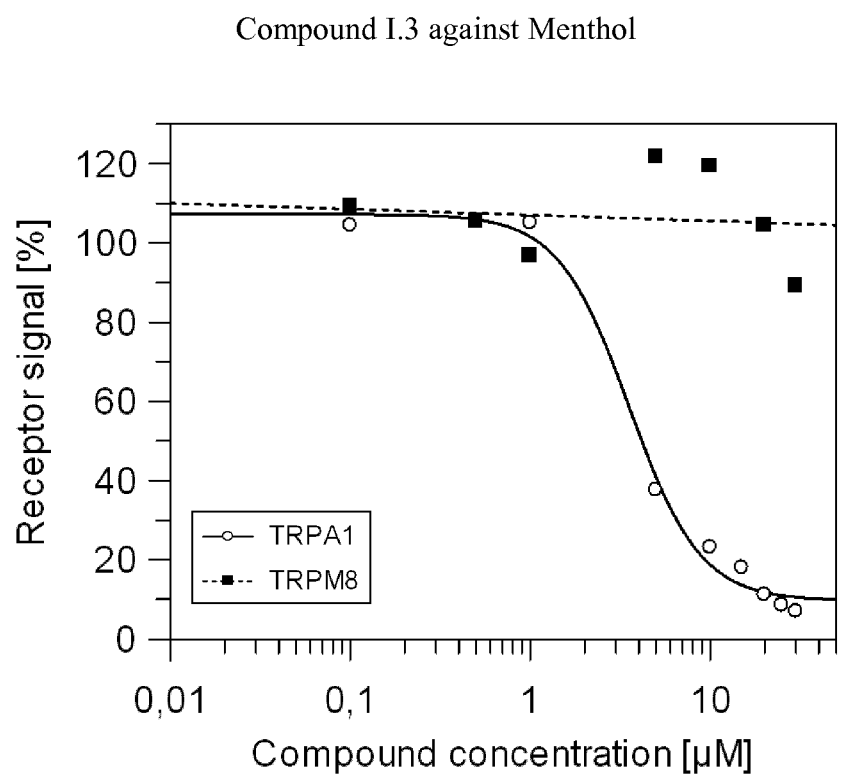
Figure 6:
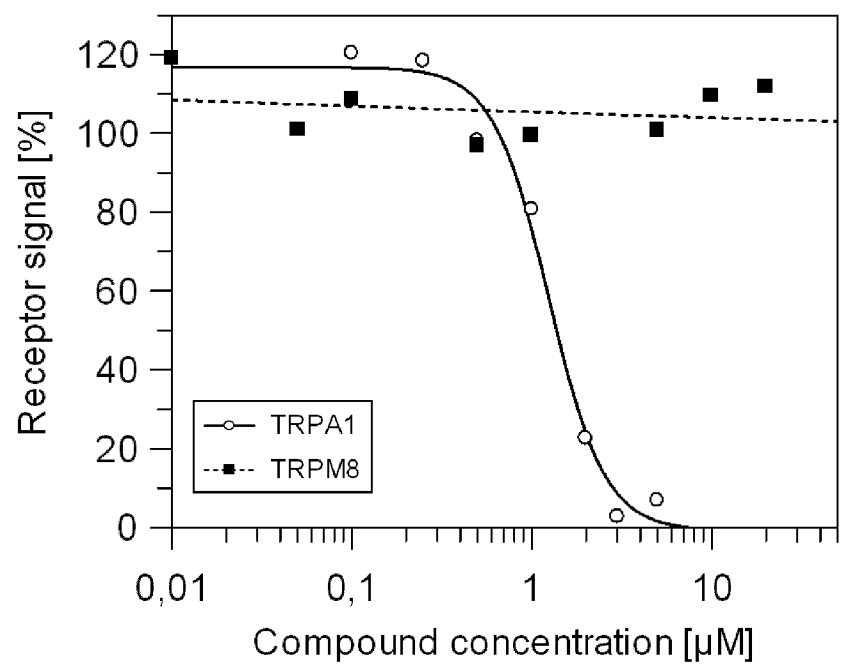
Figure 7:
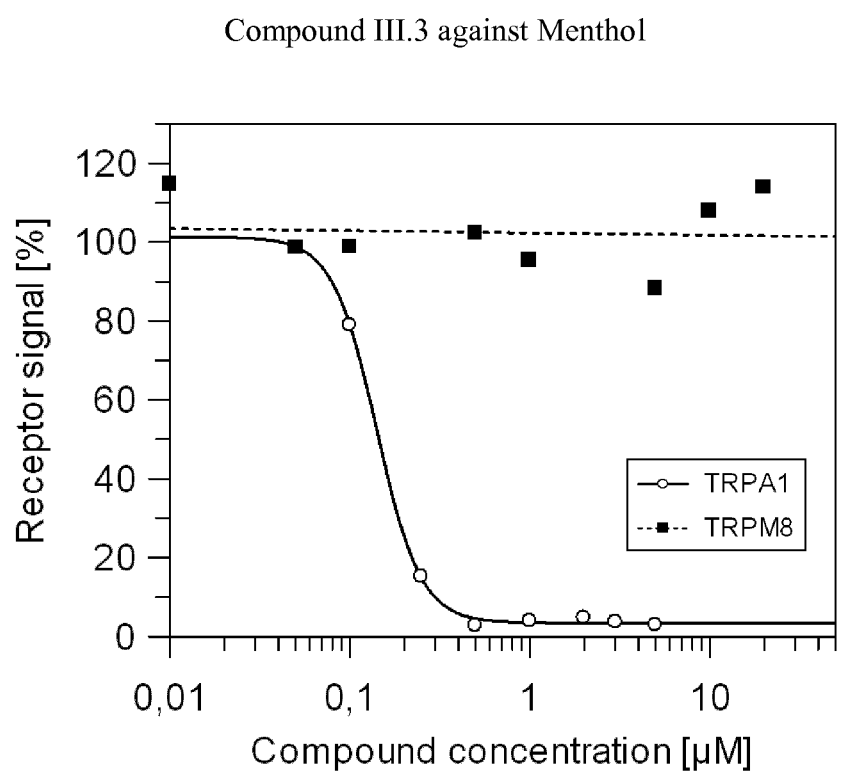
Figure 8:
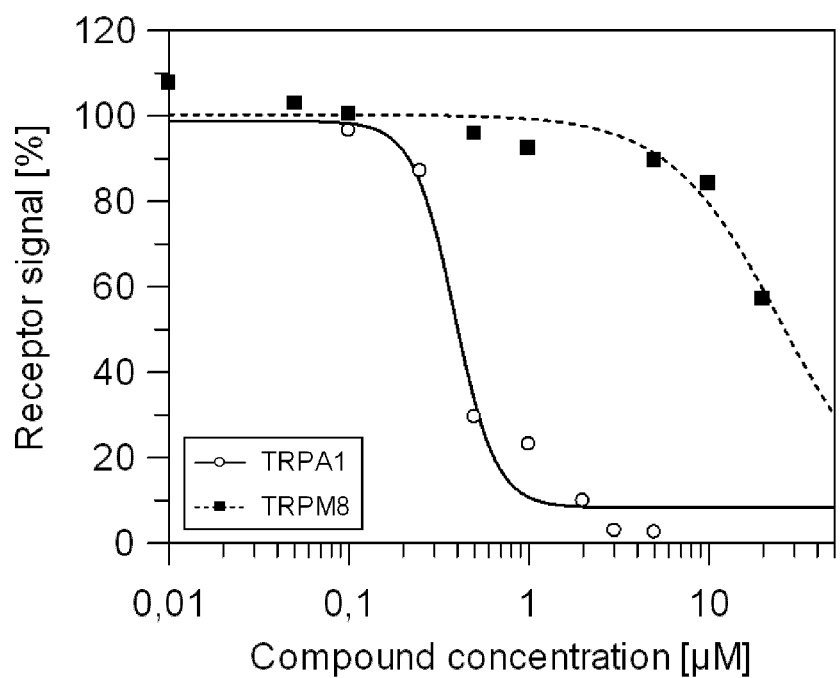
Figure 9:
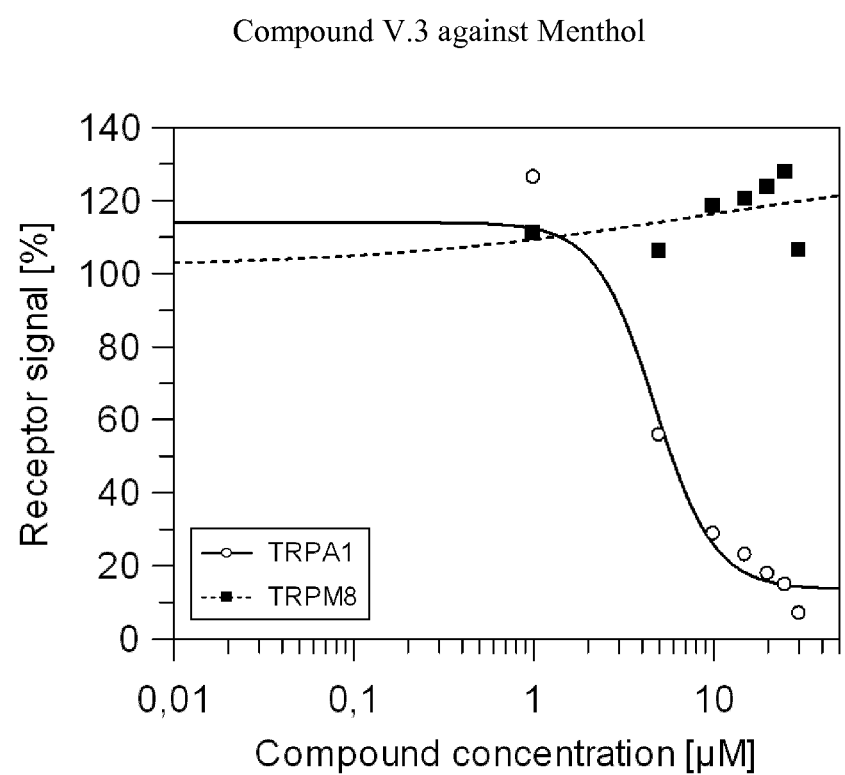

FIGS. 5-9: Dose-response curves of compound I.3-V.3 at TRPA1 and TRPM8 (calcium assay) against menthol, which is known to trigger both TRPA1 as well as TRPM8. The antagonistic activity of compounds I.3, II.3, III.3, IV.3 and V.3 at TRPA1 (open circles, continuous line) as well as the antagonistic activity of said compounds at TRPM8 (filled squares, dotted line) was measured and compared. Activation of the two ion channels was triggered by addition of menthol, which is known to trigger both TRPA1 as well as TRPM8 ($EC_{80}$-[TRPA1]=35 µM and $EC_{80}$-[TRPM8]=12 µM). The receptor signals were normalized to the pure menthol signal in each case. FIG. 5: Antagonistic activity of Compound I.3 at TRPA1 (open circles, continuous line) and TRPM8 (filled squares, dotted line) against menthol. FIG. 6: Antagonistic activity of Compound II.3 at TRPA1 (open circles, continuous line) and TRPM8 (filled squares, dotted line) against menthol. FIG. 7: Antagonistic activity of Compound III.3 at TRPA1 (open circles, continuous line) and TRPM8 (filled squares, dotted line) against menthol. FIG. 8: Antagonistic activity of Compound IV.3 at TRPA1 (open circles, continuous line) and TRPM8 (filled squares, dotted line) against menthol. FIG. 9: Antagonistic activity of Compound V.3 at TRPA1 (open circles, continuous line) and TRPM8 (filled squares, dotted line) against menthol.

Figure 10:
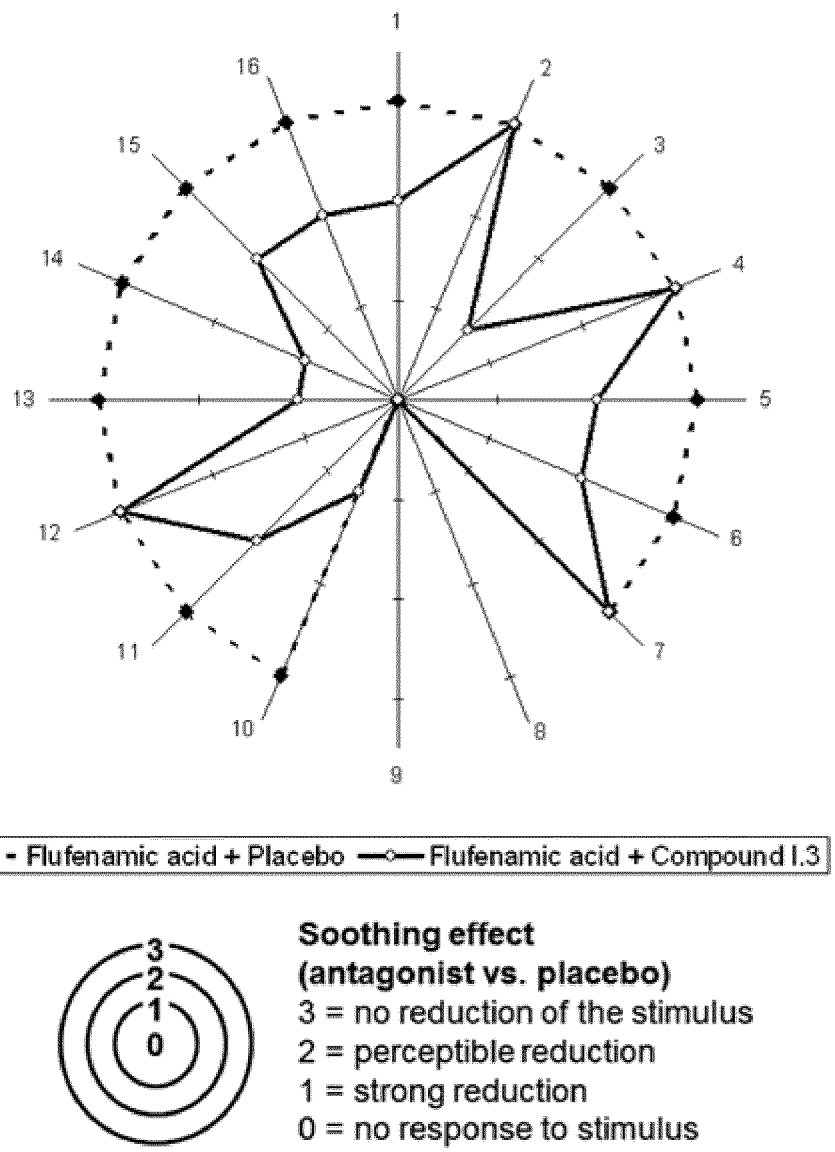

FIG. 10: Results of the blinded study on the lid-cheek junction of 16 persons performed according to example 7 showing the in vivo activity of compound I.3 according to the invention.

DETAILED DESCRIPTION OF THE INVENTION

The present invention illustratively described in the following may suitably be practiced in the absence of any element or elements, limitation or limitations, not specifically disclosed herein.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes.

Where the term "comprising" is used in the present description and claims, it does not exclude other elements or steps. For the purposes of the present invention, the term "consisting of" is considered to be a preferred embodiment of the term "comprising of". If hereinafter a group is defined to comprise at least a certain number of embodiments, this is also to be understood to disclose a group which optionally consists only of these embodiments.

Where an indefinite or definite article is used when referring to a singular noun e.g. "a" or "an", "the", this includes a plural of that noun unless something else is specifically stated.

The term "about" in the context of the present invention denotes an interval of accuracy that the person skilled in the art will understand to still ensure the technical effect of the feature in question. The term typically indicates deviation from the indicated numerical value of ±10%, and optionally ±5%.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Further definitions of term will be given in the following in the context of which the terms are used.

Compounds

In one embodiment, the present invention relates to a compound having the following general formula (I):

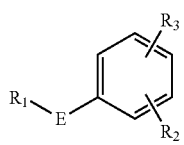

(I)

or a pharmaceutically acceptable derivative thereof wherein:
E is selected from —O—, —C(O)—, —C(=O)O—, —C(=O)NH—, —OC(=O)NH—, —OC(=O)O—, —S—, —S(=O)—, —S(=O)$_2$—, —S(=O)$_2$O—, —S(=O)$_2$NH—, —S(=O)O—, —S(=O)NH—, or —NH—;

$R_1$ is selected from —($C_3$-$C_{20}$)cycloalkyl, —($C_6$-$C_{14}$)bicycloalkyl, —($C_8$-$C_{20}$)tricycloalkyl, —($C_5$-$C_{20}$)cycloalkenyl, —($C_7$-$C_{14}$)bicycloalkenyl, —($C_8$-$C_{20}$)tricycloalkenyl, -(5- or 6-membered)heterocycle, or -(7- to 10-membered)bicycloheterocycle, each of which is unsubstituted or substituted with 1, 2, 3, 4, 5, 6, 7 or 8 independently selected $R_4$ groups;

$R_2$ and $R_3$ are each independently selected from:
  (a) -hydrogen; or
  (b) -halo, —CN, —NO$_2$; or
  (c) —OT$_3$, —OC(=O)T$_3$, —OC(=O)N(T$_1$)(T$_2$), —OC(=O)OT$_3$; or
  (d) —C(=O)T$_3$, —C(=O)OT$_3$, —C(=O)N(T$_1$)(T$_2$); or
  (e) —ST$_3$, —S(=O)T$_3$, —S(=O)$_2$T$_3$, —S(=O)$_2$OT$_3$, —S(=O)$_2$N(T$_1$)(T$_2$), —S(=O)OT$_3$, —S(=O)N(T$_1$)(T$_2$); or
  (f) —N(T$_1$)(T$_2$), —N(T$_3$)N(T$_1$)(T$_2$), —N(T$_3$)C(=O)T$_3$, —N(T$_3$)C(=O)OT$_3$, —N(T$_3$)C(=O)N(T$_1$)(T$_2$), —N(T$_3$)S(=O)$_2$T$_3$, —N(T$_3$)S(=O)$_2$N(T$_1$)(T$_2$), —N(T$_3$)S(=O)T$_3$, —N(T$_3$)S(=O)N(T$_1$)(T$_2$); or
  (g) —($C_1$-$C_6$)alkyl, —($C_2$-$C_6$)alkenyl, —($C_2$-$C_6$)alkynyl, —($C_1$-$C_6$)alkoxy, —($C_3$-$C_7$)cycloalkyl, —($C_6$-$C_{14}$)bicycloalkyl, each of which is unsubstituted or substituted with 1, 2 or 3 independently selected $R_5$ groups; or
  (h) -phenyl or -(5- or 6-membered)heteroaryl, each of which is unsubstituted or substituted with 1, 2 or 3 independently selected $R_6$ groups;

with the proviso that $R_2$ and $R_3$ are not both hydrogen;

$R_4$ and $R_5$ are each independently selected from —($C_1$-$C_4$)alkyl, —($C_2$-$C_6$)alkenyl, —($C_2$-$C_6$)alkynyl, -(5- or 6-membered)heteroaryl, -phenyl, —($C_1$-$C_6$)alkylCOOR$_7$, —OR$_7$, —SR$_7$, —C(halo)$_3$, —CH(halo)$_2$, —CH$_2$(halo), —CN, =O, =S, -halo, —N$_3$, —NO$_2$, —CH=N(R$_7$), —NR$_7$($C_1$-$C_6$)alkylCOOR$_7$, —N(R$_7$)$_2$, —N(R$_7$)OH, —N(R$_7$)S(=O)R$_8$, —N(R$_7$)S(=O)$_2$R$_8$, —N(R$_7$)C(=O)R$_8$, —N(R$_7$)C(=O)N(R$_7$)$_2$, —N(R$_7$)C(=O)OR$_8$, —C(=O)R$_7$, —C(=O)—C(=O)OR$_7$, —C(=O)N(R$_7$)$_2$, —C(=O)OR$_7$, —OC(=O)R$_7$, —OC(=O)N(R$_7$)$_2$, —OC(=O)OR$_7$, —S(=O)R$_7$, or —S(=O)$_2$R$_7$;

each $R_6$ is independently selected from —($C_1$-$C_4$)alkyl, —($C_2$-$C_6$)alkenyl, —($C_2$-$C_6$)alkynyl, —OR$_7$, —SR$_7$, —C(halo)$_3$, —CH(halo)$_2$, —CH$_2$(halo), —CN, -halo, —N$_3$, —NO$_2$, —CH=N(R$_7$), —N(R$_7$)$_2$, —N(R$_7$)OH, —N(R$_7$)S(=O)R$_8$, —N(R$_7$)S(=O)$_2$R$_8$, —N(R$_7$)C(=O)R$_8$, —N(R$_7$)C(=O)N(R$_7$)$_2$, —N(R$_7$)C(=O)OR$_8$, —C(=O)R$_7$, —C(=O)N(R$_7$)$_2$, —C(=O)OR$_7$, —OC(=O)R$_7$, —OC(=O)N(R$_7$)$_2$, —OC(=O)OR$_7$, —S(=O)R$_7$, or —S(=O)$_2$R$_7$;

each $R_7$ is independently selected from —H, —($C_1$-$C_6$)alkyl, —($C_2$-$C_6$)alkenyl, —($C_2$-$C_6$)alkynyl, —($C_1$-$C_6$)alkoxy, —($C_3$-$C_8$)cycloalkyl, —($C_5$-$C_8$)cycloalkenyl, -phenyl, -benzyl, -(3- to 6-membered)heterocycle, -(5- to 10-membered)heteroaryl, —C(halo)$_3$, —CH(halo)$_2$, or —CH$_2$(halo);

each $R_8$ is independently selected from —H or —($C_1$-$C_4$)alkyl;

each $T_1$, $T_2$, and $T_3$ is independently —H or —($C_1$-$C_{10}$)alkyl which is unsubstituted or substituted with 1, 2 or 3 independently selected $R_5$ groups; and each halo is independently selected from —F, —Cl, —Br, or —I.

In a further embodiment, the present invention relates to a compound having the following general formula (I.1):

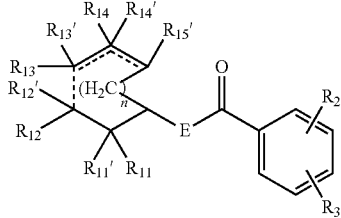
(I.1)

or a pharmaceutically acceptable derivative thereof wherein:
E is selected from O and N($T_3$);
n is an integer selected from 0 or 1;
$R_{11}$, $R_{12}$, $R_{13}$, $R_{14}$, and $R_{15}$ are each independently selected from —H, —($C_1$-$C_4$)alkyl, —($C_2$-$C_6$)alkenyl, —($C_2$-$C_6$)alkynyl, —($C_1$-$C_6$)alkylCOO$R_7$, —O$R_7$, —S$R_7$, —C(halo)$_3$, —CH(halo)$_2$, —$CH_2$(halo), —CN, -halo, —$N_3$, —$NO_2$, —CH=N($R_7$), —N($R_7$)$_2$, —N($R_7$)OH, —C(=O)$R_7$, —C(=O)—C(=O)O$R_7$, —C(=O)N($R_7$)$_2$, —C(=O)O$R_7$, —OC(=O)$R_7$, —OC(=O)N($R_7$)$_2$, —OC(=O)O$R_7$, —S(=O)$R_7$, or —S(=O)$_2$$R_7$;
the dashed lines between $R_{13}'$ and $R_{14}'$, and between $R_{14}'$ and $R_{15}'$ each denote the presence or absence of a bond, wherein:
(a) $R_{13}'$, $R_{14}'$ and $R_{15}'$ are each present if both bonds are absent; or
(b) $R_{13}'$ and $R_{14}'$ are each absent and $R_{15}'$ is present if the bond between $R_{13}'$ and $R_{14}'$ is present and the bond between $R_{14}'$ and $R_{15}'$ is absent; or
(c) $R_{13}'$ is present and $R_{14}'$ and $R_{15}'$ are absent if the bond between $R_{13}'$ and $R_{14}'$ is absent and the bond between $R_{14}'$ and $R_{15}'$ is present;
$R_{11}'$, $R_{12}'$, $R_{13}'$, $R_{14}'$, and $R_{15}'$, if present, are each independently selected from:
(a) —H, or —($C_1$-$C_4$)alkyl; or
(b) $R_{12}'$, $R_{13}'$ are each independently selected from —H, or —($C_1$-$C_4$)alkyl, and $R_{11}'$ and $R_{14}'$ together form a ($C_1$-$C_2$) bridge which is unsubstituted or substituted with 1, 2, 3 or 4 substituents independently selected from —OH, —($C_1$-$C_4$)alkyl, -halo, and —C(halo)$_3$; or
(c) $R_{11}'$ and $R_{14}'$ are each independently selected from —H, or —($C_1$-$C_4$)alkyl, and $R_{12}'$ and $R_{13}'$ together form a —($C_3$-$C_7$)cycloalkyl, —($C_6$-$C_{14}$)bicycloalkyl, —($C_5$-$C_{10}$)cycloalkenyl, —($C_7$-$C_{14}$)bicycloalkenyl, each of which is unsubstituted or substituted with 1, 2 or 3 independently selected $R_5$ groups, and wherein the bond indicated by the dashed line between $R_{12}'$ and $R_{13}'$ can be present or absent; or
(d) $R_{13}'$, $R_{14}'$ are each independently selected from —H, or —($C_1$-$C_4$)alkyl, and $R_{11}'$ and $R_{12}'$ together form a —($C_3$-$C_7$)cycloalkyl, —($C_6$-$C_{14}$)bicycloalkyl, —($C_5$-$C_{10}$)cycloalkenyl, or —($C_7$-$C_{14}$)bicycloalkenyl, each of which is unsubstituted or substituted with 1, 2 or 3 independently selected $R_5$ groups;
$R_2$ and $R_3$ are each independently selected from:
(a) -halo, —CN, —$NO_2$; or
(b) —O$T_3$, —OC(=O)$T_3$; or
(c) —C(=O)$T_3$, —C(=O)O$T_3$, —C(=O)N($T_1$)($T_2$); or
(d) —($C_1$-$C_4$)alkyl, —($C_2$-$C_4$)alkenyl, —($C_2$-$C_4$)alkynyl, —($C_1$-$C_4$)alkoxy, each of which is unsubstituted or substituted with 1 or 2 independently selected $R_5$ groups;

each $R_5$ is independently selected from —($C_1$-$C_3$)alkyl, —($C_2$-$C_3$)alkenyl, —($C_2$-$C_3$)alkynyl, —($C_1$-$C_3$)alkyl-COO$R_7$, —O$R_7$, —S$R_7$, —C(halo)$_3$, —CH(halo)$_2$, —$CH_2$(halo), —CN, =O, =S, -halo, —$N_3$, —$NO_2$, —N($R_7$)$_2$, —N($R_7$)OH, —C(=O)$R_7$, —C(=O)O$R_7$, —OC(=O)$R_7$, —S(=O)$R_7$, or —S(=O)$_2$$R_7$;
each $R_7$ is independently selected from —H, —$CH_3$, or —$CH_2CH_3$;
each $T_1$, $T_2$, and $T_3$ is independently —H or —($C_1$-$C_5$)alkyl which is unsubstituted or substituted with 1 or 2 independently selected $R_5$ groups; and
each halo is independently selected from —F, —Cl, —Br, or —I.

In a further embodiment, the present invention relates to a compound having the following general formula (III):

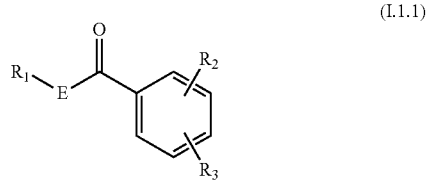
(I.1.1)

or a pharmaceutically acceptable derivative thereof wherein:
E is selected from O and N($T_3$);
$R_1$ is selected from the following general formulae:

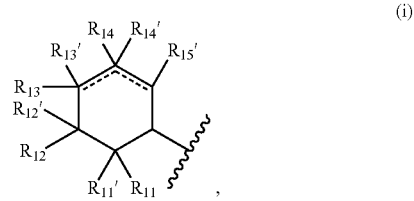
(i)

wherein
$R_{11}$, $R_{12}$, $R_{13}$ and $R_{14}$ are each independently selected from —H, —($C_2$-$C_6$)alkenyl, —($C_2$-$C_6$)alkynyl, —($C_1$-$C_6$)alkylCOO$R_7$, —O$R_7$, —S$R_7$, —C(halo)$_3$, —CH(halo)$_2$, —$CH_2$(halo), —CN, -halo, —$N_3$, —$NO_2$, —CH=N($R_7$), —N($R_7$)$_2$, —N($R_7$)OH, —C(=O)$R_7$, —C(=O)—C(=O)O$R_7$, —C(=O)N($R_7$)$_2$, —C(=O)O$R_7$, —OC(=O)$R_7$, —OC(=O)N($R_7$)$_2$, —OC(=O)O$R_7$, —S(=O)$R_7$, or —S(=O)$_2$$R_7$;
the dashed lines between $R_{13}'$ and $R_{14}'$ and $R_{14}'$ and $R_{15}'$ each denote the presence or absence of a bond, wherein:
(a) $R_{13}'$, $R_{14}'$ and $R_{15}'$ are each present if both bonds are absent; or
(b) $R_{13}'$ and $R_{14}'$ are each absent and $R_{15}'$ is present if the bond between $R_{13}'$ and $R_{14}'$ is present and the bond between $R_{14}'$ and $R_{15}'$ is absent; or
(c) $R_{13}'$ is present and $R_{14}'$ and $R_{15}'$ are absent if the bond between $R_{13}'$ and $R_{14}'$ is absent and the bond between $R_{14}'$ and $R_{15}'$ is present; and
$R_{11}'$, $R_{12}'$, $R_{13}'$, $R_{14}'$, and $R_{15}'$, if present, are each independently selected from —H, or —($C_1$-$C_4$)alkyl, wherein $R_{11}'$ and $R_{14}'$ together can form a ($C_1$-$C_2$) bridge which is unsubstituted or substituted with 1, 2, 3 or 4 substituents independently selected from —OH, —($C_1$-$C_4$)alkyl, -halo, and —C(halo)$_3$; or

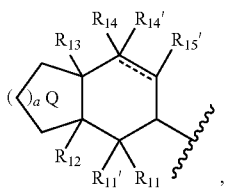
(ii)

wherein
$R_{11}$, $R_{12}$, $R_{13}$ and $R_{14}$ are each independently selected from —H, —($C_1$-$C_4$)alkyl, —($C_2$-$C_6$)alkenyl, —($C_2$-$C_6$)alkynyl, —($C_1$-$C_6$)alkylCOOR$_7$, —OR$_7$, —SR$_7$, —C(halo)$_3$, —CH(halo)$_2$, —CH$_2$(halo), —CN, -halo, —N$_3$, —NO$_2$, —CH=N(R$_7$), —N(R$_7$)$_2$, —N(R$_7$)OH, —C(=O)R$_7$, —C(=O)—C(=O)OR$_7$, —C(=O)N(R$_7$)$_2$, —C(=O)OR$_7$, —OC(=O)R$_7$, —OC(=O)N(R$_7$)$_2$, —OC(=O)OR$_7$, —S(=O)R$_7$, or —S(=O)$_2$R$_7$;
the dashed line between $R_{14}'$ and $R_{15}'$ denotes the presence or absence of a bond, wherein:
(a) $R_{14}'$ and $R_{15}'$ are present if the bond is absent; or
(b) $R_{14}'$ and $R_{15}'$ are absent if the bond is present;
$R_{11}'$, $R_{14}'$, and $R_{15}'$, if present, are each independently selected from —H, or —($C_1$-$C_4$)alkyl; and
a is an integer selected from 1, 2, or 3; wherein:
(a) if a=1, the ring denoted as Q is —($C_5$)cycloalkyl, or —($C_5$)cycloalkenyl, each of which is unsubstituted or substituted with 1, 2 or 3 independently selected $R_5$ groups;
(b) if a=2, the ring denoted as Q is —($C_6$)cycloalkyl, or —($C_6$)cycloalkenyl, each of which is unsubstituted or substituted with 1, 2 or 3 independently selected $R_5$ groups;
(c) if a=3, the ring denoted as Q is —($C_7$)cycloalkyl, or —($C_7$)cycloalkenyl, each of which is unsubstituted or substituted with 1, 2, 3 or 4 independently selected $R_5$ groups; or

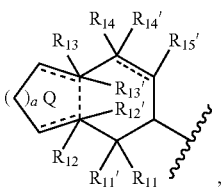
(iii)

wherein
$R_{11}$, $R_{12}$, $R_{13}$ and $R_{14}$ are each independently selected from —H, —($C_1$-$C_4$)alkyl, —($C_2$-$C_6$)alkenyl, —($C_2$-$C_6$)alkynyl, —($C_1$-$C_6$)alkylCOOR$_7$, —OR$_7$, —SR$_7$, —C(halo)$_3$, —CH(halo)$_2$, —CH$_2$(halo), —CN, -halo, —N$_3$, —NO$_2$, —CH=N(R$_7$), —N(R$_7$)$_2$, —N(R$_7$)OH, —C(=O)R$_7$, —C(=O)—C(=O)OR$_7$, —C(=O)N(R$_7$)$_2$, —C(=O)OR$_7$, —OC(=O)R$_7$, —OC(=O)N(R$_7$)$_2$, —OC(=O)OR$_7$, —S(=O)R$_7$, or —S(=O)$_2$R$_7$;
the dashed line between $R_{14}'$ and $R_{15}'$ denotes the presence or absence of a bond, wherein:
(a) $R_{14}'$ and $R_{15}'$ are present if the bond is absent; or
(b) $R_{14}'$ and $R_{15}'$ are absent if the bond is present;
the dashed line between $R_{12}$ and $R_{13}$ denotes the absence of a bond;
the dashed lines together with the solid lines in the ring denoted as Q each independently denote the presence or absence of a double bond, wherein $R_{12}'$ is absent if the carbon atom carrying $R_{12}'$ is unsaturated, and wherein $R_{13}'$ is absent if the carbon atom carrying $R_{13}'$ is unsaturated;
$R_{11}'$, $R_{12}'$, $R_{13}'$, $R_{14}'$, and $R_{15}'$, if present, are each independently selected from —H, or —($C_1$-$C_4$)alkyl; and
a is an integer selected from 1, 2, or 3; wherein:
(a) if a=1, the ring denoted as Q is —($C_5$)cycloalkyl, or —($C_5$)cycloalkenyl, each of which is unsubstituted or substituted with 1, 2 or 3 independently selected $R_5$ groups;
(b) if a=2, the ring denoted as Q is —($C_6$)cycloalkyl, or —($C_6$)cycloalkenyl, each of which is unsubstituted or substituted with 1, 2 or 3 independently selected $R_5$ groups;
(c) if a=3, the ring denoted as Q is —($C_7$)cycloalkyl, or —($C_7$)cycloalkenyl, each of which is unsubstituted or substituted with 1, 2, 3 or 4 independently selected $R_5$ groups; or

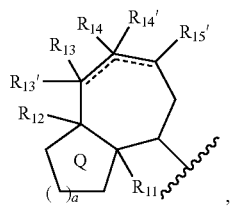
(iv)

wherein
$R_{11}$, $R_{12}$, $R_{13}$ and $R_{14}$ are each independently selected from —H, —($C_1$-$C_4$)alkyl, —($C_2$-$C_6$)alkenyl, —($C_2$-$C_6$)alkynyl, —($C_1$-$C_6$)alkylCOOR$_7$, —OR$_7$, —SR$_7$, —C(halo)$_3$, —CH(halo)$_2$, —CH$_2$(halo), —CN, -halo, —N$_3$, —NO$_2$, —CH=N(R$_7$), —N(R$_7$)$_2$, —N(R$_7$)OH, —C(=O)R$_7$, —C(=O)—C(=O)OR$_7$, —C(=O)N(R$_7$)$_2$, —C(=O)OR$_7$, —OC(=O)R$_7$, —OC(=O)N(R$_7$)$_2$, —OC(=O)OR$_7$, —S(=O)R$_7$, or —S(=O)$_2$R$_7$;
the dashed lines between $R_{13}'$ and $R_{14}'$ and $R_{14}'$ and $R_{15}'$ each denote the presence or absence of a bond, wherein:
(a) $R_{13}'$, $R_{14}'$ and $R_{15}'$ are each present if both bonds are absent; or
(b) $R_{13}'$ and $R_{14}'$ are each absent and $R_{15}'$ is present if the bond between $R_{13}'$ and $R_{14}'$ is present and the bond between $R_{14}'$ and $R_{15}'$ is absent; or
(c) $R_{13}'$ is present and $R_{14}'$ and $R_{15}'$ are absent if the bond between $R_{13}'$ and $R_{14}'$ is absent and the bond between $R_{14}'$ and $R_{15}'$ is present;
$R_{11}'$, $R_{12}'$, $R_{13}'$, $R_{14}'$, and $R_{15}'$, if present, are each independently selected from —H, or —($C_1$-$C_4$)alkyl; and
a is an integer selected from 1, 2, or 3; wherein:
(a) if a=1, the ring denoted as Q is —($C_5$)cycloalkyl, or —($C_5$)cycloalkenyl, each of which is unsubstituted or substituted with 1, 2 or 3 independently selected $R_5$ groups;
(b) if a=2, the ring denoted as Q is —($C_6$)cycloalkyl, or —($C_6$)cycloalkenyl, each of which is unsubstituted or substituted with 1, 2 or 3 independently selected $R_5$ groups;
(c) if a=3, the ring denoted as Q is —($C_7$)cycloalkyl, or —($C_7$)cycloalkenyl, each of which is unsubstituted or substituted with 1, 2, 3 or 4 independently selected $R_5$ groups;

$R_2$ and $R_3$ are each independently selected from:
  (a) -halo, —CN, —$NO_2$; or
  (b) —$OT_3$, —OC(=O)$T_3$; or
  (c) —C(=O)$T_3$, —C(=O)O$T_3$, —C(=O)N($T_1$)($T_2$); or
  (d) —($C_1$-$C_4$)alkyl, —($C_2$-$C_4$)alkenyl, —($C_2$-$C_4$)alkynyl, —($C_1$-$C_4$)alkoxy, each of which is unsubstituted or substituted with 1 or 2 independently selected $R_5$ groups;
each $R_5$ is independently selected from —($C_1$-$C_3$)alkyl, —($C_2$-$C_3$)alkenyl, —($C_2$-$C_3$)alkynyl, —($C_1$-$C_3$)alkyl-COO$R_7$, —O$R_7$, —S$R_7$, —C(halo)$_3$, —CH(halo)$_2$, —$CH_2$(halo), —CN, =O, =S, -halo, —$N_3$, —$NO_2$, —N($R_7$)$_2$, —N($R_7$)OH, —C(=O)$R_7$, —C(=O)O$R_7$, —OC(=O)$R_7$, —S(=O)$R_7$, or —S(=O)$_2R_7$;
each $R_6$ is independently selected from —($C_1$-$C_3$)alkyl, —($C_2$-$C_3$)alkenyl, —($C_2$-$C_3$)alkynyl, —O$R_7$, —S$R_7$, —C(halo)$_3$, —CH(halo)$_2$, —$CH_2$(halo), —CN, -halo, —$N_3$, —$NO_2$, —N($R_7$)$_2$, —N($R_7$)OH, —C(=O)$R_7$, —C(=O)O$R_7$, —OC(=O)$R_7$, —S(=O)$R_7$, or —S(=O)$_2R_7$;
each $R_7$ is independently selected from —H, —$CH_3$, or —$CH_2CH_3$;
each $T_1$, $T_2$, and $T_3$ is independently —H or —($C_1$-$C_3$)alkyl which is unsubstituted or substituted with 1 or 2 independently selected $R_5$ groups; and
each halo is independently selected from —F, —Cl, —Br, or —I.

In a further embodiment, the present invention relates to a compound having the following general formula (I.2):

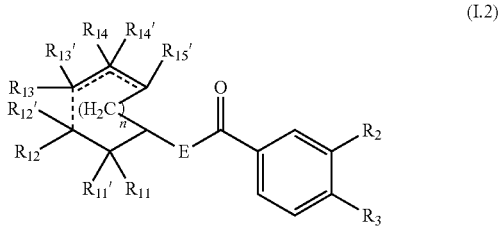

(I.2)

or a pharmaceutically acceptable derivative thereof wherein:
E is selected from O and N($T_3$);
n is an integer selected from 0 or 1;
$R_{11}$, $R_{12}$, $R_{13}$, and $R_{14}$ are each independently selected from —H, —($C_1$-$C_4$)alkyl, —($C_2$-$C_4$)alkenyl, —($C_2$-$C_4$)alkynyl, —O$R_7$, —S$R_7$, —C(halo)$_3$, —CH(halo)$_2$, —$CH_2$(halo), —CN, -halo, —$N_3$, —$NO_2$, —N($R_7$)$_2$, —N($R_7$)OH, —C(=O)$R_7$, —C(=O)N($R_7$)$_2$, —C(=O)O$R_7$, —OC(=O)$R_7$, —S(=O)$R_7$, or —S(=O)$_2R_7$;
the dashed line between $R_{14}'$ and $R_{15}'$ denotes the presence or absence of a bond, wherein:
  (a) $R_{14}'$ and $R_{15}'$ are present if the bond is absent; or
  (b) $R_{14}'$ and $R_{15}'$ are absent if the bond is present;
$R_{11}'$, $R_{12}'$, $R_{13}'$, $R_{14}'$, and $R_{15}'$, if present, are each independently selected from:
  (a) —H, or —($C_1$-$C_3$)alkyl; or
  (b) $R_{12}'$, $R_{13}'$ are each independently selected from —H, or —($C_1$-$C_3$)alkyl, and $R_{11}'$ and $R_{14}'$ together form a ($C_1$-$C_2$) bridge which is unsubstituted or substituted with 1, 2, 3 or 4 substituents independently selected from —OH, —($C_1$-$C_2$)alkyl, -halo, and —C(halo)$_3$; or
  (c) if n=0, $R_{11}'$ and $R_{14}'$ are each independently selected from —H, or —($C_1$-$C_3$)alkyl, and $R_{12}'$ and $R_{13}'$ together form a —($C_5$-$C_7$)cycloalkyl or —($C_5$-$C_7$)cycloalkenyl, each of which is unsubstituted or substituted with 1, 2, 3 or 4 independently selected $R_5$ groups, and wherein the bond indicated by the dashed line between $R_{12}'$ and $R_{13}'$ can be present or absent; or
  (d) if n=1, $R_{13}'$, $R_{14}'$ are each independently selected from —H, or —($C_1$-$C_4$)alkyl, and $R_{11}'$ and $R_{12}'$ together form a —($C_5$-$C_7$)cycloalkyl or —($C_5$-$C_7$)cycloalkenyl, each of which is unsubstituted or substituted with 1, 2, 3 or 4 independently selected $R_5$ groups;
$R_2$ and $R_3$ are each independently selected from:
  (a) -halo, —CN, —$NO_2$; or
  (b) —$OT_3$, —OC(=O)$T_3$; or
  (c) —C(=O)$T_3$, —C(=O)O$T_3$, —C(=O)N($T_1$)($T_2$); or
  (d) —($C_1$-$C_3$)alkyl, —($C_2$-$C_3$)alkenyl, —($C_2$-$C_3$)alkynyl, —($C_1$-$C_3$)alkoxy, each of which is unsubstituted or substituted with 1 or 2 independently selected $R_5$ groups;
each $R_5$ is independently selected from —H, —($C_1$-$C_3$)alkyl, —($C_3$)alkenyl, —($C_3$)alkynyl, —O$R_7$, —C(halo)$_3$, —CH(halo)$_2$, —$CH_2$(halo), —CN, -halo, —$N_3$, —$NO_2$, —N($R_7$)$_2$, —N($R_7$)OH, —C(=O)$R_7$, or —C(=O)O$R_7$;
each $R_7$ is independently selected from —H, or —$CH_3$;
each $T_1$, $T_2$, and $T_3$ is independently —H or —$CH_3$; and
each halo is independently selected from —F, —Cl, —Br, or —I.

In a further embodiment, the present invention relates to a compound having the following general formula (I.2.1):

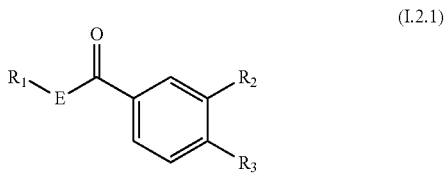

(I.2.1)

or a pharmaceutically acceptable derivative thereof wherein:
E is selected from O and N($T_3$);
$R_1$ is selected from the following general formulae:

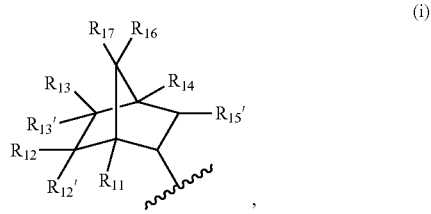

(i)

wherein
  $R_{11}$, $R_{12}$, $R_{13}$, and $R_{14}$ are each independently selected from —H, —($C_1$-$C_4$)alkyl, —($C_2$-$C_4$)alkenyl, —($C_2$-$C_4$)alkynyl, —O$R_7$, —S$R_7$, —C(halo)$_3$, —CH(halo)$_2$, —$CH_2$(halo), —CN, -halo, —$N_3$, —$NO_2$, —N($R_7$)$_2$, —N($R_7$)OH, —C(=O)$R_7$, —C(=O)N($R_7$)$_2$, —C(=O)O$R_7$, —OC(=O)$R_7$, —S(=O)$R_7$, or —S(=O)$_2R_7$;
  $R_{11}'$, $R_{12}'$, $R_{13}'$, $R_{14}'$, and $R_{15}'$, if present, are each independently selected from —H, or —($C_1$-$C_3$)alkyl; and
  $R_{16}$ and $R_{17}$ are each independently selected from —H, —OH, —($C_1$-$C_2$)alkyl, -halo, and —C(halo)$_3$; or

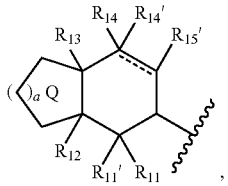

(ii)

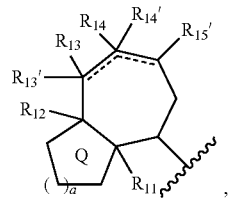

(iv)

wherein $R_{11}$, $R_{12}$, $R_{13}$, and $R_{14}$ are each independently selected from —H, —$(C_1-C_4)$alkyl, —$(C_2-C_4)$alkenyl, —$(C_2-C_4)$alkynyl, —$OR_7$, —$SR_7$, —$C(halo)_3$, —$CH(halo)_2$, —$CH_2(halo)$, —CN, -halo, —$N_3$, —$NO_2$, —$N(R_7)_2$, —$N(R_7)OH$, —$C(=O)R_7$, —$C(=O)N(R_7)_2$, —$C(=O)OR_7$, —$OC(=O)R_7$, —$S(=O)R_7$, or —$S(=O)_2R_7$;

the dashed line between $R_{14}'$ and $R_{15}'$ denotes the presence or absence of a bond, wherein:
 (a) $R_{14}'$ and $R_{15}'$ are present if the bond is absent; or
 (b) $R_{14}'$ and $R_{15}'$ are absent if the bond is present;

$R_{11}'$, $R_{14}'$, and $R_{15}'$, if present, are each independently selected from —H, or —$(C_1-C_3)$alkyl; and a is an integer selected from 2 or 3; wherein:
 (a) if a=2, the ring denoted as Q is —$(C_6)$cycloalkyl, or —$(C_6)$cycloalkenyl, each of which is unsubstituted or substituted with 1, 2 or 3 independently selected $R_5$ groups;
 (b) if a=3, the ring denoted as Q is —$(C_7)$cycloalkyl, or —$(C_7)$cycloalkenyl, each of which is unsubstituted or substituted with 1, 2, 3 or 4 independently selected $R_5$ groups; or

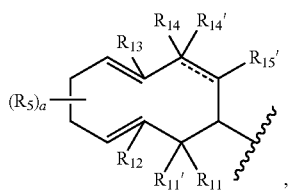

(iii)

wherein $R_{11}$, $R_{12}$, $R_{13}$, and $R_{14}$ are each independently selected from —H, —$(C_1-C_4)$alkyl, —$(C_2-C_4)$alkenyl, —$(C_2-C_4)$alkynyl, —$OR_7$, —$SR_7$, —$C(halo)_3$, —$CH(halo)_2$, —$CH_2(halo)$, —CN, -halo, —$N_3$, —$NO_2$, —$N(R_7)_2$, —$N(R_7)OH$, —$C(=O)R_7$, —$C(=O)N(R_7)_2$, —$C(=O)OR_7$, —$OC(=O)R_7$, —$S(=O)R_7$, or —$S(=O)_2R_7$;

the dashed line between $R_{14}'$ and $R_{15}'$ denotes the presence or absence of a bond, wherein:
 (a) $R_{14}'$ and $R_{15}'$ are present if the bond is absent; or
 (b) $R_{14}'$ and $R_{15}'$ are absent if the bond is present;

$R_{11}'$, $R_{14}'$, and $R_{15}'$, if present, are each independently selected from —H, or —$(C_1-C_3)$alkyl; and a is an integer selected from 1, 2 or 3; or wherein $R_{11}$, $R_{12}$, $R_{13}$, and $R_{14}$ are each independently selected from —H, —$(C_1-C_4)$alkyl, —$(C_2-C_4)$alkenyl, —$(C_2-C_4)$alkynyl, —$OR_7$, —$SR_7$, —$C(halo)_3$, —$CH(halo)_2$, —$CH_2(halo)$, —CN, -halo, —$N_3$, —$NO_2$, —$N(R_7)_2$, —$N(R_7)OH$, —$C(=O)R_7$, —$C(=O)N(R_7)_2$, —$C(=O)OR_7$, —$OC(=O)R_7$, —$S(=O)R_7$, or —$S(=O)_2R_7$;

the dashed lines between $R_{13}'$ and $R_{14}'$ and $R_{14}'$ and $R_{15}'$ each denote the presence or absence of a bond, wherein:
 (a) $R_{13}'$, $R_{14}'$ and $R_{15}'$ are each present if both bonds are absent; or
 (b) $R_{13}'$ and $R_{14}'$ are each absent and $R_{15}'$ is present if the bond between $R_{13}'$ and $R_{14}'$ is present and the bond between $R_{14}'$ and $R_{15}'$ is absent; or
 (c) $R_{13}'$ is present and $R_{14}'$ and $R_{15}'$ are absent if the bond between $R_{13}'$ and $R_{14}'$ is absent and the bond between $R_{14}'$ and $R_{15}'$ is present;

$R_{11}'$, $R_{12}'$, $R_{13}'$, $R_{14}'$, and $R_{15}'$, if present, are each independently selected from —H, or —$(C_1-C_3)$alkyl; and a is an integer selected from 1 or 2; wherein:
 (a) if a=1, the ring denoted as Q is —$(C_5)$cycloalkyl, or —$(C_5)$cycloalkenyl, each of which is unsubstituted or substituted with 1, 2 or 3 independently selected $R_5$ groups;
 (b) if a=2, the ring denoted as Q is —$(C_6)$cycloalkyl, or —$(C_6)$cycloalkenyl, each of which is unsubstituted or substituted with 1, 2 or 3 independently selected $R_5$ groups;

$R_2$ and $R_3$ are each independently selected from:
 (a) -halo, —CN, —$NO_2$; or
 (b) —$OT_3$, —$OC(=O)T_3$; or
 (c) —$C(=O)T_3$, —$C(=O)OT_3$, —$C(=O)N(T_1)(T_2)$; or
 (d) —$(C_1-C_3)$alkyl, —$(C_2-C_3)$alkenyl, —$(C_2-C_3)$alkynyl, —$(C_1-C_3)$alkoxy, each of which is unsubstituted or substituted with 1 or 2 independently selected $R_5$ groups;

each $R_5$ is independently selected from —H, —$(C_1-C_3)$alkyl, —$(C_3)$alkenyl, —$(C_3)$alkynyl, —$OR_7$, —$C(halo)_3$, —$CH(halo)_2$, —$CH_2(halo)$, —CN, -halo, —$N_3$, —$NO_2$, —$N(R_7)_2$, —$N(R_7)OH$, —$C(=O)R_7$, or —$C(=O)OR_7$;

each $R_7$ is independently selected from —H, or —$CH_3$;

each $T_1$, $T_2$, and $T_3$ is independently —H or —$CH_3$; and each halo is independently selected from —F, —Cl, —Br, or —I.

In an optional embodiment, the present invention relates to a compound having the general formula (I.2) or (I.2.1) or a pharmaceutically acceptable derivative thereof, wherein E is O.

In an optional embodiment, the present invention relates to a compound having the general formula (I.2) or (I.2.1) or a pharmaceutically acceptable derivative thereof, wherein $R_2$ and $R_3$ are each independently selected from —OH, —$OCH_3$, —$OC(=O)H$, —$OC(=O)CH_3$, —$C(=O)H$, —$C(=O)CH_3$, —$C(=O)OH$, or —$C(=O)OCH_3$.

In an optional embodiment, the present invention relates to a compound having the general formula (I.2) or (I.2.1) or a pharmaceutically acceptable derivative thereof, wherein $R_2$ is selected from —OH or —OCH$_3$, and $R_3$ is selected from —OH, —OCH$_3$, —OC(=O)H or —OC(=O)CH$_3$.

In an optional embodiment, the present invention relates to a compound having the general formula (I.2) or (I.2.1) or a pharmaceutically acceptable derivative thereof, wherein $R_{11}$, $R_{12}$, $R_{13}$, $R_{14}$, and $R_{15}$ are each independently selected from —H, —(C$_1$-C$_3$)alkyl, —OH, or —OCH$_3$.

In an optional embodiment, the present invention relates to a compound having the general formula (I.2.1) or a pharmaceutically acceptable derivative thereof, wherein $R_1$ is:

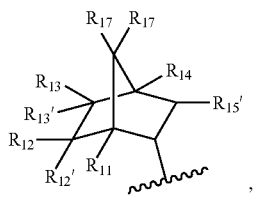

wherein $R_{11}$, $R_{12}$, $R_{13}$, and $R_{14}$ are each independently selected from —H, —(C$_1$-C$_3$)alkyl, —OH, or —OCH$_3$;

$R_{11}'$, $R_{12}'$, $R_{13}'$, $R_{14}'$, and $R_{15}'$, if present, are each independently selected from —H, or —(C$_1$-C$_3$)alkyl; and $R_{16}$ and $R_{17}$ are each independently selected from —H, and —(C$_1$-C$_2$)alkyl.

In an optional embodiment, the present invention relates to a compound having the general formula (I.2.1) or a pharmaceutically acceptable derivative thereof, wherein $R_1$ is:

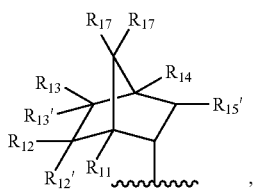

wherein $R_{11}$, $R_{12}$, $R_{13}$, and $R_{14}$ are each independently selected from —H, —(C$_1$-C$_4$)alkyl, —(C$_2$-C$_4$)alkenyl, —(C$_2$-C$_4$)alkynyl, —OR$_7$, —SR$_7$, —C(halo)$_3$, —CH(halo)$_2$, —CH$_2$(halo), —CN, -halo, —N$_3$, —NO$_2$, —N(R$_7$)$_2$, —N(R$_7$)OH, —C(=O)R$_7$, —C(=O)N(R$_7$)$_2$, —C(=O)OR$_7$, —OC(=O)R$_7$, —S(=O)R$_7$, or —S(=O)$_2$R$_7$;

$R_{11}'$, $R_{12}'$, $R_{13}'$, $R_{14}'$, and $R_{15}'$, if present, are each independently selected from —H, or —(C$_1$-C$_3$)alkyl; and $R_{16}$ and $R_{17}$ are each independently selected from —H, —OH, —(C$_1$-C$_2$)alkyl, -halo, and —C(halo)$_3$.

In an optional embodiment, the present invention relates to a compound having the general formula (I.2.1) or a pharmaceutically acceptable derivative thereof, wherein $R_1$ is:

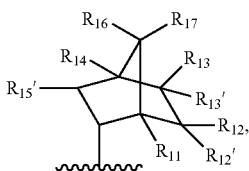

wherein $R_{11}$, $R_{12}$, $R_{13}$, and $R_{14}$ are each independently selected from —H, —(C$_1$-C$_4$)alkyl, —(C$_2$-C$_4$)alkenyl, —(C$_2$-C$_4$)alkynyl, —OR$_7$, —SR$_7$, —C(halo)$_3$, —CH(halo)$_2$, —CH$_2$(halo), —CN, -halo, —N$_3$, —NO$_2$, —N(R$_7$)$_2$, —N(R$_7$)OH, —C(=O)R$_7$, —C(=O)N(R$_7$)$_2$, —C(=O)OR$_7$, —OC(=O)R$_7$, —S(=O)R$_7$, or —S(=O)$_2$R$_7$;

$R_{11}'$, $R_{12}'$, $R_{13}'$, $R_{14}'$, and $R_{15}'$, if present, are each independently selected from —H, or —(C$_1$-C$_3$)alkyl; and $R_{16}$ and $R_{17}$ are each independently selected from —H, —OH, —(C$_1$-C$_2$)alkyl, -halo, and —C(halo)$_3$.

In an optional embodiment, the present invention relates to a compound having the general formula (I.2.1) or a pharmaceutically acceptable derivative thereof, wherein $R_1$ is:

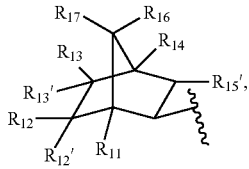

wherein $R_{11}$, $R_{12}$, $R_{13}$, and $R_{14}$ are each independently selected from —H, —(C$_1$-C$_4$)alkyl, —(C2-C4)alkenyl, —(C$_2$-C$_4$)alkynyl, —OR$_7$, —SR$_7$, —C(halo)$_3$, —CH(halo)$_2$, —CH$_2$(halo), —CN, -halo, —N$_3$, —NO$_2$, —N(R$_7$)$_2$, —N(R$_7$)OH, —C(=O)R$_7$, —C(=O)N(R$_7$)$_2$, —C(=O)OR$_7$, —OC(=O)R$_7$, —S(=O)R$_7$, or —S(=O)$_2$R$_7$;

$R_{11}'$, $R_{12}'$, $R_{13}'$, $R_{14}'$, and $R_{15}'$, if present, are each independently selected from —H, or —(C$_1$-C$_3$)alkyl; and $R_{16}$ and $R_{17}$ are each independently selected from —H, —OH, —(C$_1$-C$_2$)alkyl, -halo, and —C(halo)$_3$.

In an optional embodiment, the present invention relates to a compound having the general formula (I.2.1) or a pharmaceutically acceptable derivative thereof, wherein $R_1$ is:

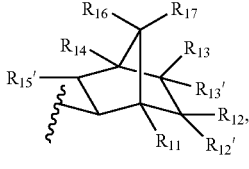

wherein $R_{11}$, $R_{12}$, $R_{13}$, and $R_{14}$ are each independently selected from —H, —(C$_1$-C$_4$)alkyl, —(C2-C4)alkenyl, —(C$_2$-C$_4$)alkynyl, —OR$_7$, —SR$_7$, —C(halo)$_3$, —CH(halo)$_2$, —CH$_2$(halo), —CN, -halo, —N$_3$, —NO$_2$, —N(R$_7$)$_2$, —N(R$_7$)OH, —C(=O)R$_7$, —C(=O)N(R$_7$)$_2$, —C(=O)OR$_7$, —OC(=O)R$_7$, —S(=O)R$_7$, or —S(=O)$_2$R$_7$;

$R_{11}'$, $R_{12}'$, $R_{13}'$, $R_{14}'$, and $R_{15}'$, if present, are each independently selected from —H, or —($C_1$-$C_3$)alkyl; and
$R_{16}$ and $R_{17}$ are each independently selected from —H, —OH, —($C_1$-$C_2$)alkyl, -halo, and —C(halo)$_3$.

In an optional embodiment, the present invention relates to a compound having the general formula (I.2.1) or a pharmaceutically acceptable derivative thereof, wherein $R_1$ is:

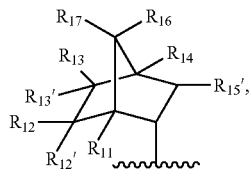

wherein
$R_{11}$, $R_{12}$, $R_{13}$, and $R_{14}$ are each independently selected from —H, —($C_1$-$C_3$)alkyl, —OH, or —OCH$_3$;
$R_{11}'$, $R_{12}'$, $R_{13}'$, $R_{14}'$, and $R_{15}'$, if present, are each independently selected from —H, or —($C_1$-$C_3$)alkyl; and
$R_{16}$ and $R_{17}$ are each independently selected from —H, and —($C_1$-$C_2$)alkyl.

In an optional embodiment, the present invention relates to a compound having the general formula (I.2.1) or a pharmaceutically acceptable derivative thereof, wherein $R_1$ is:

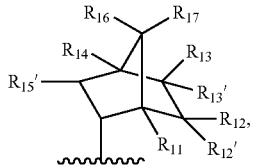

wherein
$R_{11}$, $R_{12}$, $R_{13}$, and $R_{14}$ are each independently selected from —H, —($C_1$-$C_3$)alkyl, —OH, or —OCH$_3$;
$R_{11}'$, $R_{12}'$, $R_{13}'$, $R_{14}'$, and $R_{15}'$, if present, are each independently selected from —H, or —($C_1$-$C_3$)alkyl; and
$R_{16}$ and $R_{17}$ are each independently selected from —H, and —($C_1$-$C_2$)alkyl.

In an optional embodiment, the present invention relates to a compound having the general formula (I.2.1) or a pharmaceutically acceptable derivative thereof, wherein $R_1$ is:

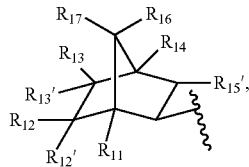

wherein
$R_{11}$, $R_{12}$, $R_{13}$, and $R_{14}$ are each independently selected from —H, —($C_1$-$C_3$)alkyl, —OH, or —OCH$_3$;
$R_{11}'$, $R_{12}'$, $R_{13}'$, $R_{14}'$, and $R_{15}'$, if present, are each independently selected from —H, or —($C_1$-$C_3$)alkyl; and
$R_{16}$ and $R_{17}$ are each independently selected from —H, and —($C_1$-$C_2$)alkyl.

In an optional embodiment, the present invention relates to a compound having the general formula (I.2.1) or a pharmaceutically acceptable derivative thereof, wherein $R_1$ is:

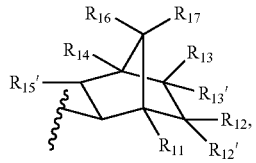

wherein
$R_{11}$, $R_{12}$, $R_{13}$, and $R_{14}$ are each independently selected from —H, —($C_1$-$C_3$)alkyl, —OH, or —OCH$_3$;
$R_{11}'$, $R_{12}'$, $R_{13}'$, $R_{14}'$, and $R_{15}'$, if present, are each independently selected from —H, or —($C_1$-$C_3$)alkyl; and
$R_{16}$ and $R_{17}$ are each independently selected from —H, and —($C_1$-$C_2$)alkyl.

In an optional embodiment, the present invention relates to a compound having the general formula (I.2.1) or a pharmaceutically acceptable derivative thereof, wherein $R_1$ is selected from (+)-borneole, (−)-borneole, (+)-isoborneole, or (−)-isoborneole.

In an optional embodiment, the present invention relates to a compound having the general formula (I.2.1) or a pharmaceutically acceptable derivative thereof, wherein $R_1$ is:

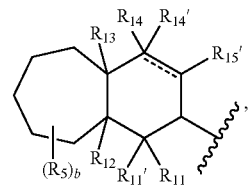

wherein
$R_{11}$, $R_{12}$, $R_{13}$, and $R_{14}$ are each independently selected —H, —($C_1$-$C_3$)alkyl, —OH, or —OCH$_3$;
the dashed line between $R_{14}'$ and $R_{15}'$ denotes the presence or absence of a bond, wherein:
(a) $R_{14}'$ and $R_{15}'$ are present if the bond is absent; or
(b) $R_{14}'$ and $R_{15}'$ are absent if the bond is present;
$R_{11}'$, $R_{14}'$, and $R_{15}'$, if present, are each independently selected from —H, or —($C_1$-$C_2$)alkyl;
b is an integer selected from 2, 3 or 4; and
each $R_5$ is independently selected from —H, —($C_1$-$C_3$)alkyl, —OH, or —OCH$_3$.

In an optional embodiment, the present invention relates to a compound having the general formula (I.2.1) or a pharmaceutically acceptable derivative thereof, wherein $R_1$ is:

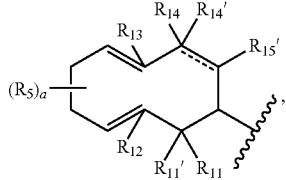

wherein
R$_{11}$, R$_{12}$, R$_{13}$, and R$_{14}$ are each independently selected —H, —(C$_1$-C$_3$)alkyl, —OH, or —OCH$_3$;

the dashed line between R$_{14}$' and R$_{15}$' denotes the presence or absence of a bond, wherein:
(a) R$_{14}$' and R$_{15}$' are present if the bond is absent; or
(b) R$_{14}$' and R$_{15}$' are absent if the bond is present;

R$_{11}$', R$_{14}$', and R$_{15}$', if present, are each independently selected from —H, or —(C$_1$-C$_2$)alkyl;

a is an integer selected from 0, 1, 2 or 3; and each R$_5$ is independently selected from —H, —(C$_1$-C$_3$)alkyl, —OH, or —OCH$_3$.

In an optional embodiment, the present invention relates to a compound having the general formula (I.2.1) or a pharmaceutically acceptable derivative thereof, wherein R$_1$ is:

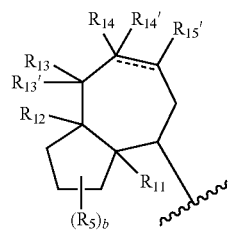

wherein
R$_{11}$, R$_{12}$, R$_{13}$, and R$_{14}$ are each independently selected —H, —(C$_1$-C$_3$)alkyl, —OH, or —OCH$_3$;

the dashed line between R$_{14}$' and R$_{15}$' denotes the presence or absence of a bond, wherein:
(a) R$_{14}$' and R$_{15}$' are present if the bond is absent; or
(b) R$_{14}$' and R$_{15}$' are absent if the bond is present;

R$_{11}$', R$_{14}$', and R$_{15}$', if present, are each independently selected from —H, or —(C$_1$-C$_2$)alkyl;

b is an integer selected from 1, 2 or 3; and each R$_5$ is independently selected from —H, —(C$_1$-C$_3$)alkyl, —OH, or —OCH$_3$.

In an optional embodiment, the present invention relates to a compound having the following general formula (I.2A):

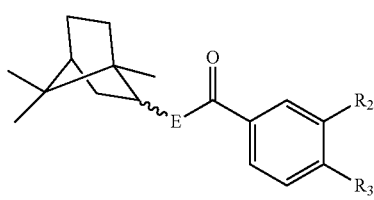

(I.2A)

or a pharmaceutically acceptable derivative thereof wherein:
E is selected from O and NH, optionally O; and
R$_2$ and R$_3$ are each independently selected from —OH, —OCH$_3$, —OC(=O)H, —OC(=O)CH$_3$, —C(=O)H, —C(=O)CH$_3$, —C(=O)OH, or —C(=O)OCH$_3$.

In an optional embodiment, the present invention relates to a compound having the following general formula (I.2B):

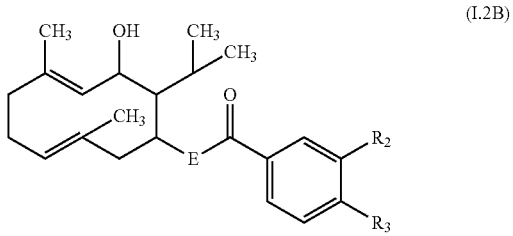

(I.2B)

or a pharmaceutically acceptable derivative thereof wherein:
E is selected from O and NH, optionally O; and
R$_2$ and R$_3$ are each independently selected from —OH, —OCH$_3$, —OC(=O)H, —OC(=O)CH$_3$, —C(=O)H, —C(=O)CH$_3$, —C(=O)OH, or —C(=O)OCH$_3$.

In an optional embodiment, the present invention relates to a compound having the following general formula (I.2C):

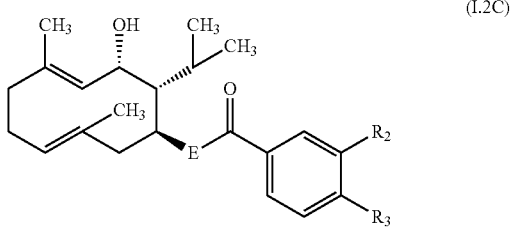

(I.2C)

or a pharmaceutically acceptable derivative thereof wherein:
E is selected from O and NH, optionally O; and
R$_2$ and R$_3$ are each independently selected from —OH, —OCH$_3$, —OC(=O)H, —OC(=O)CH$_3$, —C(=O)H, —C(=O)CH$_3$, —C(=O)OH, or —C(=O)OCH$_3$.

In an optional embodiment, the present invention relates to a compound having the following general formula (I.2D):

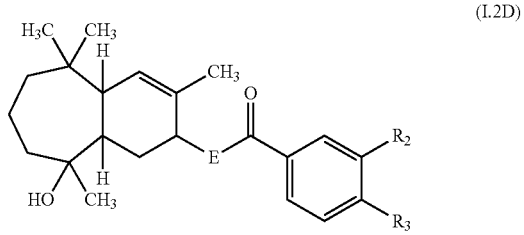

(I.2D)

or a pharmaceutically acceptable derivative thereof wherein:
E is selected from O and NH, optionally O; and
R$_2$ and R$_3$ are each independently selected from —OH, —OCH$_3$, —OC(=O)H, —OC(=O)CH$_3$, —C(=O)H, —C(=O)CH$_3$, —C(=O)OH, or —C(=O)OCH$_3$.

In an optional embodiment, the present invention relates to a compound having the following general formula (I.2E):

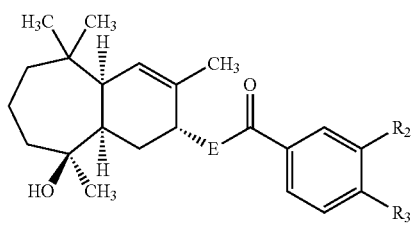
(I.2E)

or a pharmaceutically acceptable derivative thereof wherein:

E is selected from O and NH, optionally O; and $R_2$ and $R_3$ are each independently selected from —OH, —OCH$_3$, —OC(=O)H, —OC(=O)CH$_3$, —C(=O)H, —C(=O)CH$_3$, —C(=O)OH, or —C(=O)OCH$_3$.

In an optional embodiment, the present invention relates to a compound having the following general formula (I.2F):

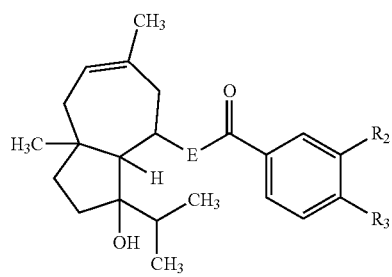
(I.2F)

or a pharmaceutically acceptable derivative thereof wherein:

E is selected from O and NH, optionally O; and $R_2$ and $R_3$ are each independently selected from —OH, —OCH$_3$, —OC(=O)H, —OC(=O)CH$_3$, —C(=O)H, —C(=O)CH$_3$, —C(=O)OH, or —C(=O)OCH$_3$.

In an optional embodiment, the present invention relates to a compound having the following general formula (I.2G):

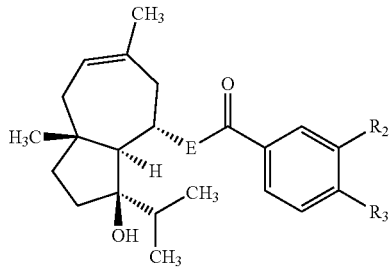
(I.2G)

or a pharmaceutically acceptable derivative thereof wherein:

E is selected from O and NH, optionally O; and $R_2$ and $R_3$ are each independently selected from —OH, —OCH$_3$, —OC(=O)H, —OC(=O)CH$_3$, —C(=O)H, —C(=O)CH$_3$, —C(=O)OH, or —C(=O)OCH$_3$.

In an optional embodiment, the present invention relates to a compound having the following formula (I.2H):

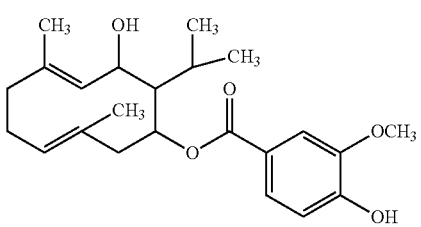
(I.2H)

In an optional embodiment, the present invention relates to a compound having the following formula (I.2I):

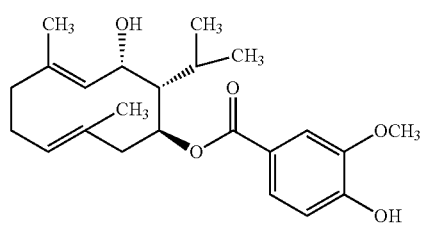
(I.2I)

In an optional embodiment, the present invention relates to a compound having the following formula (I.2J):

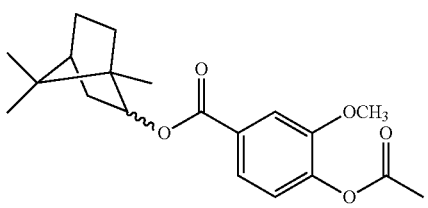
(I.2J)

In an optional embodiment, the present invention relates to a compound having the following formula (I.2K):

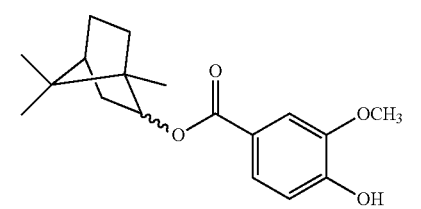
(I.2K)

In an optional embodiment, the present invention relates to a compound having the following formula (I.2L):

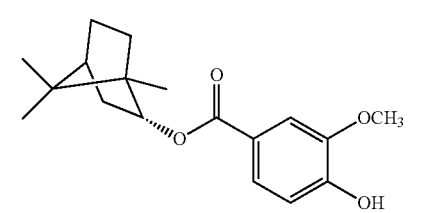
(I.2L)

In an optional embodiment, the present invention relates to a compound having the following formula (I.2M):

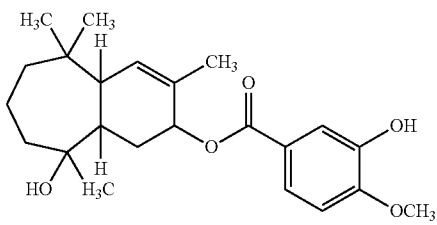

(I.2M)

In an optional embodiment, the present invention relates to a compound having the following formula (I.2N):

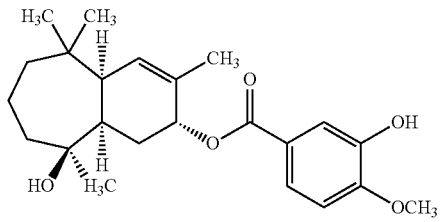

(I.2N)

In an optional embodiment, the present invention relates to a compound having the following formula (I.2O):

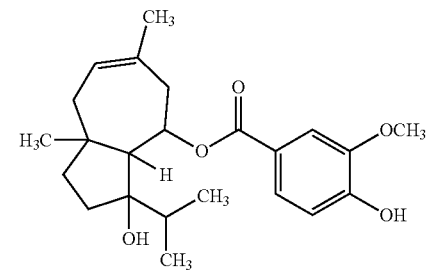

(I.2O)

In an optional embodiment, the present invention relates to a compound having the following formula (I.2P):

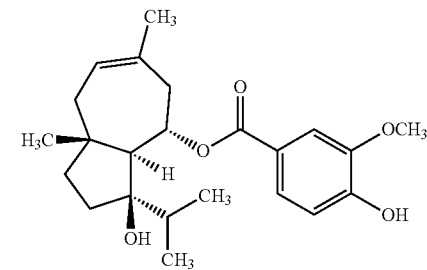

(I.2P)

In a further embodiment, the present invention relates to a compound having the following general formula (II):

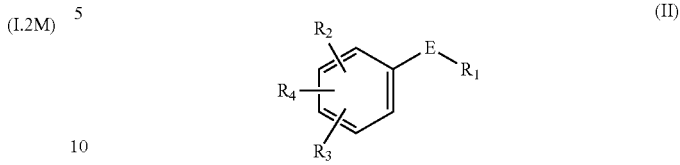

(II)

or a pharmaceutically acceptable derivative thereof wherein:
E is selected from —O—, —C(O)—, —C(=O)O—, —C(=O)NH—, —OC(=O)NH—, —OC(=O)O—, —S—, —S(=O)—, —S(=O)$_2$—, —S(=O)$_2$O—, —S(=O)$_2$NH—, —S(=O)O—, —S(=O)NH—, or —NH—;
$R_1$ is selected from —($C_1$-$C_6$)alkyl, —($C_2$-$C_6$)alkenyl, —($C_2$-$C_6$)alkynyl, —($C_1$-$C_6$)alkoxy, —($C_3$-$C_7$)cycloalkyl, —($C_6$-$C_{14}$)bicycloalkyl, each of which is unsubstituted or substituted with 1, 2 or 3 independently selected $R_5$ groups;
$R_2$ and $R_3$ are each independently selected from —H, —($C_1$-$C_4$)alkyl, —($C_2$-$C_6$)alkenyl, —($C_2$-$C_6$)alkynyl, —$OR_7$, —$SR_7$, —C(halo)$_3$, —CH(halo)$_2$, —CH$_2$(halo), —CN, -halo, —N$_3$, —NO$_2$, —CH=N($R_7$), —N($R_7$)$_2$, —N($R_7$)OH, —N($R_7$)S(=O)$R_8$, —N($R_7$)S(=O)$_2R_8$, —N($R_7$)C(=O)$R_8$, —N($R_7$)C(=O)N($R_7$)$_2$, —N($R_7$)C(=O)$OR_8$, —C(=O)$R_7$, —C(=O)N($R_7$)$_2$, —C(=O)$OR_7$, —OC(=O)$R_7$, —OC(=O)N($R_7$)$_2$, —OC(=O)$OR_7$, —S(=O)$R_7$, or —S(=O)$_2R_7$;
with the proviso that $R_2$ and $R_3$ are not both hydrogen;
$R_4$ is selected from:
(a) —($C_3$-$C_7$)cycloalkyl, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, -(5- or 6-membered)heterocycle, or -(7- to 10-membered)bicycloheterocycle, each of which is unsubstituted or substituted with 1, 2 or 3 independently selected $R_5$ groups; or
(b) -phenyl, or -(5- or 6-membered)heteroaryl, each of which is unsubstituted or substituted with 1, 2 or 3 independently selected $R_6$ groups;
each $R_5$ is independently selected from —($C_1$-$C_4$)alkyl, —($C_2$-$C_6$)alkenyl, —($C_2$-$C_6$)alkynyl, -(5- or 6-membered)heteroaryl, -phenyl, —($C_1$-$C_6$)alkylCOOR$_7$, —$OR_7$, —$SR_7$, —C(halo)$_3$, —CH(halo)$_2$, —CH$_2$(halo), —CN, =O, =S, -halo, —N$_3$, —NO$_2$, —CH=N($R_7$), —NR$_7$($C_1$-$C_6$)alkyl-COOR$_7$, —N($R_7$)$_2$, —N($R_7$)OH, —N($R_7$)S(=O)$R_8$, —N($R_7$)S(=O)$_2R_8$, —N($R_7$)C(=O)$R_8$, —N($R_7$)C(=O)N($R_7$)$_2$, —N($R_7$)C(=O)$OR_8$, —C(=O)$R_7$, —C(=O)—C(=O)$OR_7$, —C(=O)N($R_7$)$_2$, —C(=O)$OR_7$, —OC(=O)$R_7$, —OC(=O)N($R_7$)$_2$, —OC(=O)$OR_7$, —S(=O)$R_7$, or —S(=O)$_2R_7$;
each $R_6$ is independently selected from —($C_1$-$C_4$)alkyl, —($C_2$-$C_6$)alkenyl, —($C_2$-$C_6$)alkynyl, —$OR_7$, —$SR_7$, —C(halo)$_3$, —CH(halo)$_2$, —CH$_2$(halo), —CN, -halo, —N$_3$, —NO$_2$, —CH=N($R_7$), —N($R_7$)$_2$, —N($R_7$)OH, —N($R_7$)S(=O)$R_8$, —N($R_7$)S(=O)$_2R_8$, —N($R_7$)C(=O)$R_8$, —N($R_7$)C(=O)N($R_7$)$_2$, —N($R_7$)C(=O)$OR_8$, —C(=O)$R_7$, —C(=O)N($R_7$)$_2$, —C(=O)$OR_7$, —OC(=O)$R_7$, —OC(=O)N($R_7$)$_2$, —OC(=O)$OR_7$, —S(=O)$R_7$, or —S(=O)$_2R_7$;
each $R_7$ is independently selected from —H, —($C_1$-$C_6$)alkyl, —($C_2$-$C_6$)alkenyl, —($C_2$-$C_6$)alkynyl, —($C_1$-$C_6$)alkoxy, —($C_3$-$C_8$)cycloalkyl, —($C_5$-$C_8$)cycloalkenyl, -phenyl, -benzyl, -(3- to 6-membered)heterocycle, -(5- to 10-membered)heteroaryl, —C(halo)$_3$, —CH(halo)$_2$, or —CH$_2$(halo);

each $R_8$ is independently selected from —H or —($C_1$-$C_4$)alkyl;
each $T_1$, $T_2$, and $T_3$ is independently —H or —($C_1$-$C_{10}$)alkyl which is unsubstituted or substituted with 1, 2 or 3 independently selected $R_5$ groups; and
each halo is independently selected from —F, —Cl, —Br, or —I.

In a further embodiment, the present invention relates to a compound having the following general formula (II.1):

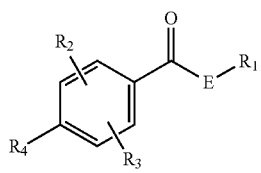

(II.1)

or a pharmaceutically acceptable derivative thereof wherein:
E is O or N($T_3$);
$R_1$ is selected from —($C_1$-$C_4$)alkyl, —($C_2$-$C_4$)alkenyl, or —($C_2$-$C_4$)alkynyl, each of which is unsubstituted or substituted with 1 or 2 independently selected $R_5$ groups;
$R_2$ and $R_3$ are each independently selected from —H, —($C_2$-$C_3$)alkenyl, —($C_2$-$C_3$)alkynyl, —$OR_7$, —$SR_7$, —$N_3$, —$NO_2$, —CH=N($R_7$), —N($R_7$)$_2$, —N($R_7$)OH, —N($R_7$)S(=O)$R_8$, —N($R_7$)S(=O)$_2R_8$, —N($R_7$)C(=O)$R_8$, —N($R_7$)C(=O)N($R_7$)$_2$, —CN, —C(=O)$R_7$, —C(=O)$OR_7$, —OC(=O)$R_7$, —S(=O)$R_7$, or —S(=O)$_2R_7$; with the proviso that
$R_2$ and $R_3$ are not both hydrogen;
$R_4$ is selected from -phenyl, or -(5- or 6-membered)heteroaryl containing at least one nitrogen atom, each of which is unsubstituted or substituted with 1 or 2 independently selected $R_6$ groups;
each $R_5$ is independently selected from —($C_1$-$C_3$)alkyl, —($C_2$-$C_3$)alkenyl, —($C_2$-$C_3$)alkynyl, —($C_1$-$C_3$)alkyl-$COOR_7$, —$OR_7$, —$SR_7$, —C(halo)$_3$, —CH(halo)$_2$, —$CH_2$(halo), —CN, =O, =S, -halo, —$N_3$, —$NO_2$, —N($R_7$)$_2$, —N($R_7$)OH, —C(=O)$R_7$, —C(=O)$OR_7$, —OC(=O)$R_7$, —S(=O)$R_7$, or —S(=O)$_2R_7$;
each $R_6$ is independently selected from —($C_1$-$C_3$)alkyl, —($C_2$-$C_3$)alkenyl, —($C_2$-$C_3$)alkynyl, —$OR_7$, —$SR_7$, —C(halo)$_3$, —CH(halo)$_2$, —$CH_2$(halo), —CN, -halo, —$N_3$, —$NO_2$, —N($R_7$)$_2$, —N($R_7$)OH, —C(=O)$R_7$, —C(=O)$OR_7$, —OC(=O)$R_7$, —S(=O)$R_7$, or —S(=O)$_2R_7$;
each $R_7$ is independently selected from —H, —$CH_3$, or —$CH_2CH_3$;
each $T_3$ is independently —H or —($C_1$-$C_5$)alkyl which is unsubstituted or substituted with 1 or 2 independently selected $R_5$ groups; and
each halo is independently selected from —F, —Cl, —Br, or —I.

In a further embodiment, the present invention relates to a compound having the following general formula (II.2):

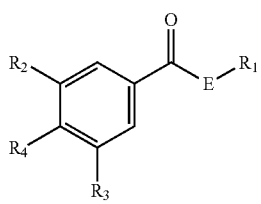

(II.2)

or a pharmaceutically acceptable derivative thereof wherein:
E is O or N($T_3$);
$R_1$ is —($C_1$-$C_3$)alkyl which is unsubstituted or substituted with 1 or 2 independently selected $R_5$ groups;
$R_2$ and $R_3$ are each independently selected from —CN, -halo, —$N_3$, —$NO_2$, —N($R_7$)$_2$, —N($R_7$)OH;
$R_4$ is selected from -phenyl or -(5- or 6-membered)heteroaryl selected from the group consisting of diazole, triazole, pyridine, pyrazine, pyridazine and pyrimidine;
each $R_5$ is independently selected from —H, —($C_1$-$C_2$)alkyl, —($C_2$)alkenyl, —($C_2$)alkynyl, —$OR_7$, —$SR_7$, —C(halo)$_3$, —CH(halo)$_2$, —$CH_2$(halo), —CN, -halo, —$N_3$, —$NO_2$, —N($R_7$)$_2$, —N($R_7$)OH, —C(=O)$R_7$, —C(=O)$OR_7$, —S(=O)$R_7$, or —S(=O)$_2R_7$;
each $R_7$ is independently selected from —H, or —$CH_3$; and
each $T_3$ is independently selected from —H or —$CH_3$; and
each halo is independently selected from —F, —Cl, —Br, or —I.

In an optional embodiment, the present invention relates to a compound having the general formula (II.2) or a pharmaceutically acceptable derivative thereof, wherein E is O.

In an optional embodiment, the present invention relates to a compound having the general formula (II.2) or a pharmaceutically acceptable derivative thereof, wherein $R_1$ is —$CH_3$ or —$CH_2CH_3$.

In an optional embodiment, the present invention relates to a compound having the general formula (II.2) or a pharmaceutically acceptable derivative thereof, wherein $R_2$ and $R_3$ are each independently selected from —$NO_2$, or —$NH_2$, optionally —$NO_2$.

In an optional embodiment, the present invention relates to a compound having the general formula (II.2) or a pharmaceutically acceptable derivative thereof, wherein $R_4$ is a diazole or a triazole ring.

In an optional embodiment, the present invention relates to a compound having the general formula (II.2) or a pharmaceutically acceptable derivative thereof, wherein $R_4$ is

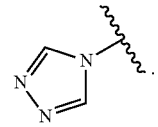

In a further embodiment, the present invention relates to a compound having the following general formula (III):

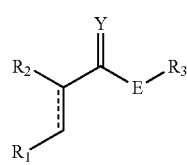

(III)

or a pharmaceutically acceptable derivative thereof wherein:
$R_1$ is selected from:
(a) —($C_3$-$C_7$)cycloalkyl, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, -(5- or 6-membered)heterocycle, or -(7- to 10-membered)bicycloheterocycle, each of which is unsubstituted or substituted with 1, 2 or 3 independently selected $R_4$ groups; or
(b) -phenyl, -naphthalenyl, —$(C_{1-4})$aryl, or -(5- or 6-membered)heteroaryl, each of which is unsubstituted or substituted with 1, 2 or 3 independently selected $R_4$ groups;

$R_2$ is selected from:
(a) —H; or
(b) -halo, —CN, —$NO_2$; or
(c) =O, —$OT_3$, —OC(=O)$T_3$, —OC(=O)N($T_1$)($T_2$), —OC(=O)$OT_3$; or
(d) —C(=O)$T_3$, —C(=O)$OT_3$, —C(=O)N($T_1$)($T_2$); or
(e) =S, —$ST_3$, —S(=O)$T_3$, —S(=O)$_2T_3$, —S(=O)$_2OT_3$, —S(=O)$_2$N($T_1$)($T_2$), —S(=O)$OT_3$, —S(=O)N($T_1$)($T_2$); or
(f) =$NT_3$, —N($T_1$)($T_2$), —N($T_3$)N($T_1$)($T_2$), —N($T_3$)C(=O)$T_3$, —N($T_3$)C(=O)$OT_3$, —N($T_3$)C(=O)N($T_1$)($T_2$), —N($T_3$)S(=O)$_2T_3$, —N($T_3$)S(=O)$_2$N($T_1T_2$), —N($T_3$)S(=O)$T_3$, —N($T_3$)S(=O)N($T_1$)($T_2$); or
(g) —$(C_1-C_6)$alkyl, —$(C_2-C_6)$alkenyl, —$(C_2-C_6)$alkynyl, —$(C_1-C_6)$alkoxy, —$(C_3-C_7)$cycloalkyl, —$(C_6-C_{14})$bicycloalkyl, —$(C_8-C_{20})$tricycloalkyl, —$(C_5-C_{10})$cycloalkenyl, —$(C_7-C_{14})$bicycloalkenyl, —$(C_8-C_{20})$tricycloalkenyl, -(5- or 6-membered)heterocycle, or -(7- to 10-membered)bicycloheterocycle, each of which is unsubstituted or substituted with 1, 2 or 3 independently selected $R_5$ groups; or
(h) -phenyl or -(5- or 6-membered)heteroaryl, each of which is unsubstituted or substituted with 1, 2 or 3 independently selected $R_6$ groups;

Y is O, S, or N($T_3$);
E is O, S, or N($T_3$);
$R_3$ is selected from:
(a) —$(C_3-C_7)$cycloalkyl, —$(C_6-C_{14})$bicycloalkyl, —$(C_8-C_{20})$tricycloalkyl, —$(C_5-C_{10})$cycloalkenyl, —$(C_7-C_{14})$bicycloalkenyl, —$(C_8-C_{20})$tricycloalkenyl, -(5- or 6-membered)heterocycle, or -(7- to 10-membered)bicycloheterocycle, each of which is unsubstituted or substituted with 1, 2 or 3 independently selected $R_6$ groups; or
(b) -phenyl, -naphthalenyl, —$(C_{1-4})$aryl, or -(5- or 6-membered)heteroaryl, each of which is unsubstituted or substituted with 1, 2 or 3 independently selected $R_6$ groups;

each $R_4$ is independently selected from —$(C_1-C_4)$alkyl, —$(C_2-C_6)$alkenyl, —$(C_2-C_6)$alkynyl, —$OR_7$, —$SR_7$, —C(halo)$_3$, —CH(halo)$_2$, —$CH_2$(halo), —CN, -halo, —$N_3$, —$NO_2$, —CH=N($R_7$), —N($R_7$)$_2$, —N($R_7$)OH, —N($R_7$)S(=O)$R_8$, —N($R_7$)S(=O)$_2R_8$, —N($R_7$)C(=O)$R_8$, —N($R_7$)C(=O)N($R_7$)$_2$, —N($R_7$)C(=O)$OR_8$, —C(=O)$R_7$, —C(=O)N($R_7$)$_2$, —C(=O)$OR_7$, —OC(=O)$R_7$, —OC(=O)N($R_7$)$_2$, —OC(=O)$OR_7$, —S(=O)$R_7$, or —S(=O)$_2R_7$;

each $R_5$ is independently selected from —$(C_1-C_4)$alkyl, —$(C_2-C_6)$alkenyl, —$(C_2-C_6)$alkynyl, -(5- or 6-membered)heteroaryl, -phenyl, —$(C_1-C_6)$alkyl$COOR_7$, —$OR_7$, —$SR_7$, —C(halo)$_3$, —CH(halo)$_2$, —$CH_2$(halo), —CN, =O, =S, -halo, —$N_3$, —$NO_2$, —CH=N($R_7$), —$NR_7(C_1-C_6)$alkyl$COOR_7$, —N($R_7$)$_2$, —N($R_7$)OH, —N($R_7$)S(=O)$R_8$, —N($R_7$)S(=O)$_2R_8$, —N($R_7$)C(=O)$R_8$, —N($R_7$)C(=O)N($R_7$)$_2$, —N($R_7$)C(=O)$OR_8$, —C(=O)$R_7$, —C(=O)—C(=O)$OR_7$, —C(=O)N($R_7$)$_2$, —C(=O)$OR_7$, —OC(=O)$R_7$, —OC(=O)N($R_7$)$_2$, —OC(=O)$OR_7$, —S(=O)$R_7$, or —S(=O)$_2R_7$;

each $R_6$ is independently selected from —$(C_1-C_4)$alkyl, —$(C_2-C_6)$alkenyl, —$(C_2-C_6)$alkynyl, —$OR_7$, —$SR_7$, —C(halo)$_3$, —CH(halo)$_2$, —$CH_2$(halo), —CN, -halo, —$N_3$, —$NO_2$, —CH=N($R_7$), —N($R_7$)$_2$, —N($R_7$)OH, —N($R_7$)S(=O)$R_8$, —N($R_7$)S(=O)$_2R_8$, —N($R_7$)C(=O)$R_8$, —N($R_7$)C(=O)N($R_7$)$_2$, —N($R_7$)C(=O)$OR_8$, —C(=O)$R_7$, —C(=O)N($R_7$)$_2$, —C(=O)$OR_7$, —OC(=O)$R_7$, —OC(=O)N($R_7$)$_2$, —OC(=O)$OR_7$, —S(=O)$R_7$, or —S(=O)$_2R_7$;

each $R_7$ is independently selected from —H, —$(C_1-C_6)$alkyl, —$(C_2-C_6)$alkenyl, —$(C_2-C_6)$alkynyl, —$(C_1-C_6)$alkoxy, —$(C_3-C_8)$cycloalkyl, —$(C_5-C_8)$cycloalkenyl, -phenyl, -benzyl, -(3- to 6-membered)heterocycle, -(5- to 10-membered)heteroaryl, —C(halo)$_3$, —CH(halo)$_2$, or —$CH_2$(halo);

each $R_8$ is independently selected from —H or —$(C_1-C_4)$alkyl;

each $T_1$, $T_2$, and $T_3$ is independently —H or —$(C_1-C_{10})$alkyl which is unsubstituted or substituted with 1, 2 or 3 independently selected $R_5$ groups;

the dashed line denotes the presence or absence of a bond; and each halo is independently selected from —F, —Cl, —Br, or —I.

In a further embodiment, the present invention relates to a compound having the following general formula (III.1):

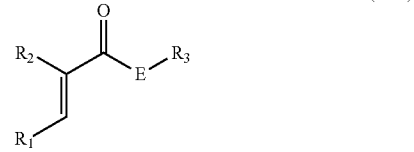

or a pharmaceutically acceptable derivative thereof wherein:
$R_1$ is selected from -phenyl or -(5- or 6-membered)heteroaryl, each of which is unsubstituted or substituted with 1 or 2 independently selected $R_4$ groups;

$R_2$ is selected from:
(a) —H; or
(b) -halo, —CN, —$NO_2$; or
(c) —$OT_3$, —OC(=O)$T_3$; or
(d) —C(=O)$T_3$, —C(=O)$OT_3$, —C(=O)N($T_1$)($T_2$); or
(e) =$NT_3$, —N($T_1$)($T_2$), —N($T_3$)N($T_1$)($T_2$), —N($T_3$)C(=O)$T_3$, —N($T_3$)C(=O)$OT_3$, —N($T_3$)C(=O)N($T_1$)($T_2$); or
(f) —$(C_1-C_5)$alkyl, —$(C_2-C_5)$alkenyl, —$(C_2-C_5)$alkynyl, —$(C_1-C_5)$alkoxy, —$(C_3-C_7)$cycloalkyl, —$(C_5-C_{10})$cycloalkenyl, or -(5- or 6-membered)heterocycle, each of which is unsubstituted or substituted with 1 or 2 independently selected $R_5$ groups;

E is selected from O or $NT_3$;
$R_3$ is selected from -phenyl or -(5- or 6-membered)heteroaryl, each of which is unsubstituted or substituted with 1 or 2 independently selected $R_6$ groups;

each $R_4$ is independently selected from —$(C_1-C_3)$alkyl, —$(C_2-C_3)$alkenyl, —$(C_2-C_3)$alkynyl, —$OR_7$, —$SR_7$, —C(halo)$_3$, —CH(halo)$_2$, —$CH_2$(halo), —CN, -halo, —$N_3$, —$NO_2$, —N($R_7$)$_2$, —N($R_7$)OH, —C(=O)$R_7$, —C(=O)$OR_7$, —C(=O)N($R_7$)$_2$, —OC(=O)$R_7$, —S(=O)$R_7$, or —S(=O)$_2R_7$;

each $R_5$ is independently selected from —$(C_1-C_3)$alkyl, —$(C_2-C_3)$alkenyl, —$(C_2-C_3)$alkynyl, —$(C_1-C_3)$alkyl$COOR_7$, —$OR_7$, —$SR_7$, —C(halo)$_3$, —CH(halo)$_2$, —$CH_2$(halo), —CN, =O, =S, -halo, —$N_3$, —$NO_2$, —N($R_7$)$_2$, —N($R_7$)OH, —C(=O)$R_7$, —C(=O)$OR_7$, —OC(=O)$R_7$, —S(=O)$R_7$, or —S(=O)$_2R_7$;

each $R_6$ is independently selected from —$(C_1$-$C_3)$alkyl, —$(C_2$-$C_3)$alkenyl, —$(C_2$-$C_3)$alkynyl, —$OR_7$, —$SR_7$, —$C(halo)_3$, —$CH(halo)_2$, —$CH_2(halo)$, —CN, -halo, —$N_3$, —$NO_2$, —$N(R_7)_2$, —$N(R_7)OH$, —$C(=O)R_7$, —$C(=O)OR_7$, —$OC(=O)R_7$, —$S(=O)R_7$, or —$S(=O)_2R_7$;

each $R_7$ is independently selected from —H, —$CH_3$, or —$CH_2CH_3$;

each $T_1$, $T_2$, and $T_3$ is independently —H or —$(C_1$-$C_5)$alkyl which is unsubstituted or substituted with 1 or 2 independently selected $R_5$ groups; and each halo is independently selected from —F, —Cl, —Br, or —I.

In a further embodiment, the present invention relates to a compound having the following general formula (III.2):

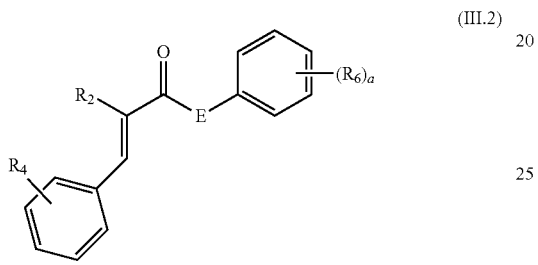

(III.2)

or a pharmaceutically acceptable derivative thereof wherein:

E is O or NH;

$R_2$ is selected from —$(C_1$-$C_2)$alkyl, —$(C_2)$alkenyl, —$(C_2)$alkynyl, —$OR_7$, —CN, —$N_3$, —$NO_2$, —$N(R_7)_2$, —$N(R_7)$OH, —$C(=O)R_7$, —$C(=O)OR_7$;

$R_4$ is selected from —$OR_7$, —$SR_7$, —$C(=O)R_7$, —$C(=O)N(R_7)_2$, —$C(=O)OR_7$, —$S(=O)R_7$, or —$S(=O)_2R_7$;

each $R_6$ is independently selected from —$C(halo)_3$, —$CH(halo)_2$, —$CH_2(halo)$, or -halo;

a is an integer selected from 1 or 2;

each $R_7$ is independently selected from —H, or —$CH_3$; and each halo is independently selected from —F, —Cl, —Br, or —I.

In an optional embodiment, the present invention relates to a compound having the general formula (III.2) or a pharmaceutically acceptable derivative thereof, wherein a is 1 and the phenyl group comprising —$(R_6)_a$ is substituted as follows:

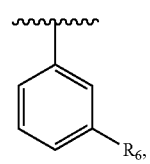

wherein $R_6$ is defined as above.

In an optional embodiment, the present invention relates to a compound having the general formula (III.2) or a pharmaceutically acceptable derivative thereof, wherein a is 1 and the phenyl group comprising —$(R_6)_a$ is substituted as follows:

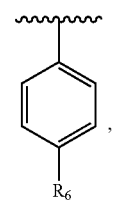

wherein $R_6$ is defined as above.

In an optional embodiment, the present invention relates to a compound having the general formula (III.2) or a pharmaceutically acceptable derivative thereof, wherein a is 1 and Hal is F.

In an optional embodiment, the present invention relates to a compound having the general formula (III.2) or a pharmaceutically acceptable derivative thereof, wherein a is 1 and the phenyl group comprising —$(R_6)_a$ is substituted as follows:

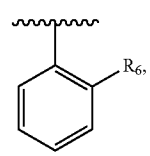

wherein $R_6$ is -Hal, optionally —F.

In an optional embodiment, the present invention relates to a compound having the general formula (III.2) or a pharmaceutically acceptable derivative thereof, wherein the phenyl group comprising —$R_4$ is substituted as follows:

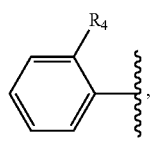

wherein $R_4$ is defined as above.

In an optional embodiment, the present invention relates to a compound having the general formula (III.2) or a pharmaceutically acceptable derivative thereof, wherein the phenyl group comprising —$R_4$ is substituted as follows:

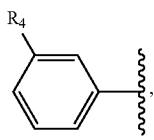

wherein $R_4$ is defined as above.

In an optional embodiment, the present invention relates to a compound having the general formula (III.2) or a pharmaceutically acceptable derivative thereof, wherein the phenyl group comprising —$R_4$ is substituted as follows:

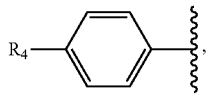

wherein $R_4$ is defined as above.

In an optional embodiment, the present invention relates to a compound having the general formula (III.2) or a pharmaceutically acceptable derivative thereof, wherein the phenyl group comprising —$R_4$ is substituted as follows:

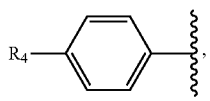

wherein $R_4$ is —C(O)OH, —C(O)OCH$_3$, —C(=O)NH$_2$, or —C(=O)N(CH$_3$)$_2$, optionally —C(O)OCH$_3$.

In an optional embodiment, the present invention relates to a compound having the general formula (III.2) or a pharmaceutically acceptable derivative thereof, wherein a is 1 and the phenyl group comprising —(R$_6$)$_a$ is substituted as follows:

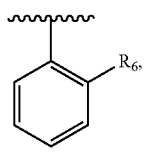

wherein $R_6$ is defined as above; and wherein the phenyl group comprising —$R_4$ is substituted as follows:

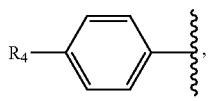

wherein $R_4$ is defined as above.

In an optional embodiment, the present invention relates to a compound having the general formula (III.2) or a pharmaceutically acceptable derivative thereof, wherein a is 1 and the phenyl group comprising —(R$_6$)$_a$ is substituted as follows:

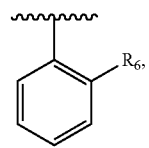

wherein $R_6$ is -Hal, optionally —F; and wherein the phenyl group comprising —$R_4$ is substituted as follows:

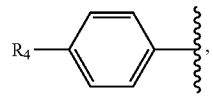

wherein $R_4$ is —C(O)OH or —C(O)OCH$_3$.

In an optional embodiment, the present invention relates to a compound having the general formula (III.2) or a pharmaceutically acceptable derivative thereof, wherein E is O.

In an optional embodiment, the present invention relates to a compound having the general formula (III.2) or a pharmaceutically acceptable derivative thereof, wherein $R_2$ is selected from —(C$_2$)alkenyl, —(C$_2$)alkynyl, or —CN.

In an optional embodiment, the present invention relates to a compound having the general formula (III.2) or a pharmaceutically acceptable derivative thereof, wherein $R_2$ is —CN.

In a further embodiment, the present invention relates to a compound having the following general formula (IV):

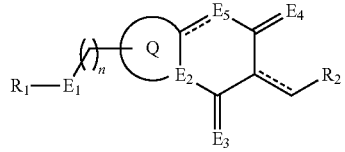

(IV)

or a pharmaceutically acceptable derivative thereof wherein:
$R_1$ is selected from:
  (a) —(C$_3$-C$_7$)cycloalkyl, —(C$_6$-C$_{14}$)bicycloalkyl, —(C$_5$-C$_{10}$)cycloalkenyl, —(C$_7$-C$_{14}$)bicycloalkenyl, -(5- or 6-membered)heterocycle, or -(7- to 10-membered)bicycloheterocycle, each of which is unsubstituted or substituted with 1, 2 or 3 independently selected $R_5$ groups; or
  (b) -phenyl or -(5- or 6-membered)heteroaryl, each of which is unsubstituted or substituted with 1, 2 or 3 independently selected $R_6$ groups;
$R_2$ is selected from:
  (a) —(C$_3$-C$_7$)cycloalkyl, —(C$_6$-C$_{14}$)bicycloalkyl, —(C$_5$-C$_{10}$)cycloalkenyl, —(C$_7$-C$_{14}$)bicycloalkenyl, -(5- or 6-membered)heterocycle, or -(7- to 10-membered)bicycloheterocycle, each of which is unsubstituted or substituted with 1, 2 or 3 independently selected $R_3$ groups; or
  (b) -phenyl or -(5- or 6-membered)heteroaryl, each of which is unsubstituted or substituted with 1, 2 or 3 independently selected $R_3$ groups;
each $R_3$ is independently selected from:
  (a) -halo, —CN, —NO$_2$; or
  (b) —OT$_3$, —OC(=O)T$_3$, —OC(=O)N(T$_1$)(T$_2$), —OC(=O)OT$_3$; or (c) —C(=O)T$_3$, —C(=O)OT$_3$, —C(=O)N(T$_1$)(T$_2$); or
(d) —ST$_3$, —S(=O)T$_3$, —S(=O)$_2$T$_3$, —S(=O)$_2$OT$_3$, —S(=O)$_2$N(T$_1$)(T$_2$), —S(=O)OT$_3$, —S(=O)N(T$_1$)(T$_2$); or
(e) —N(T$_1$)(T$_2$), —N(T$_3$)N(T$_1$)(T$_2$), —N(T$_3$)C(=O)T$_3$, —N(T$_3$)C(=O)OT$_3$, —N(T$_3$)C(=O)N(T$_1$)(T$_2$), —N(T$_3$)S(=O)$_2$T$_3$, —N(T$_3$)S(=O)$_2$N(T$_1$)(T$_2$), —N(T$_3$)S(=O)T$_3$, —N(T$_3$)S(=O)N(T$_1$)(T$_2$); or
(f) —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_6$-C$_{14}$)bicycloalkyl, each of which is unsubstituted or substituted with 1, 2 or 3 independently selected R$_5$ groups; or
(g) -phenyl or -(5- or 6-membered)heteroaryl, each of which is unsubstituted or substituted with 1, 2 or 3 independently selected R$_6$ groups;

E$_1$ is selected from —O—, —C(O)—, —C(=O)O—, —C(=O)NH—, —OC(=O)NH—, —OC(=O)O—, —S—, —S(=O)—, —S(=O)$_2$—, —S(=O)$_2$O—, —S(=O)$_2$NH—, —S(=O)O—, —S(=O)NH—, or —NH—;
E$_2$ is selected from C(T$_3$) or N;
E$_3$ and E$_4$ are each independently selected from C(T$_3$)$_2$, O, S or NT$_3$;
the dashed lines each denote the presence or absence of a bond, wherein E$_5$ is selected from C(T$_3$)$_2$, O, S or NT$_3$ if the bond is absent, and E$_5$ is selected from CT$_3$, or N if the bond is present;
Q is selected from fused benzo or (5- or 6-membered) heterocycle;
n is an integer selected from 0, 1, 2, or 3;
each R$_5$ is independently selected from —(C$_1$-C$_4$)alkyl, —(C$_2$-C$_6$)alkenyl, —(C$_2$-C$_6$)alkynyl, -(5- or 6-membered)heteroaryl, -phenyl, —(C$_1$-C$_6$)alkylCOOR$_7$, —OR$_7$, —SR$_7$, —C(halo)$_3$, —CH(halo)$_2$, —CH$_2$(halo), —CN, =O, =S, -halo, —N$_3$, —NO$_2$, —CH=N(R$_7$), —NR$_7$(C$_1$-C$_6$)alkylCOOR$_7$, —N(R$_7$)$_2$, —N(R$_7$)OH, —N(R$_7$)S(=O)R$_8$, —N(R$_7$)S(=O)$_2$R$_8$, —N(R$_7$)C(=O)R$_8$, —N(R$_7$)C(=O)N(R$_7$)$_2$, —N(R$_7$)C(=O)OR$_8$, —C(=O)R$_7$, —C(=O)—C(=O)OR$_7$, —C(=O)N(R$_7$)$_2$, —C(=O)OR$_7$, —OC(=O)R$_7$, —OC(=O)N(R$_7$)$_2$, —OC(=O)OR$_7$, —S(=O)R$_7$, or —S(=O)$_2$R$_7$;
each R$_6$ is independently selected from —(C$_1$-C$_4$)alkyl, —(C$_2$-C$_6$)alkenyl, —(C$_2$-C$_6$)alkynyl, —OR$_7$, —SR$_7$, —C(halo)$_3$, —CH(halo)$_2$, —CH$_2$(halo), —CN, -halo, —N$_3$, —NO$_2$, —CH=N(R$_7$), —N(R$_7$)$_2$, —N(R$_7$)OH, —N(R$_7$)S(=O)R$_8$, —N(R$_7$)S(=O)$_2$R$_8$, —N(R$_7$)C(=O)R$_8$, —N(R$_7$)C(=O)N(R$_7$)$_2$, —N(R$_7$)C(=O)OR$_8$, —C(=O)R$_7$, —C(=O)N(R$_7$)$_2$, —C(=O)OR$_7$, —OC(=O)R$_7$, —OC(=O)N(R$_7$)$_2$, —OC(=O)OR$_7$, —S(=O)R$_7$, or —S(=O)$_2$R$_7$;
each R$_7$ is independently selected from —H, —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_8$)cycloalkyl, —(C$_5$-C$_8$)cycloalkenyl, -phenyl, -benzyl, -(3- to 6-membered)heterocycle, -(5- to 10-membered)heteroaryl, —C(halo)$_3$, —CH(halo)$_2$, or —CH$_2$(halo);
each R$_8$ is independently selected from —H or —(C$_1$-C$_4$)alkyl;
each T$_1$, T$_2$, and T$_3$ is independently —H or —(C$_1$-C$_{10}$)alkyl which is unsubstituted or substituted with 1, 2 or 3 independently selected R$_5$ groups; and
each halo is independently selected from —F, —Cl, —Br, or —I.

In a further embodiment, the present invention relates to a compound having the following general formula (IV.1):

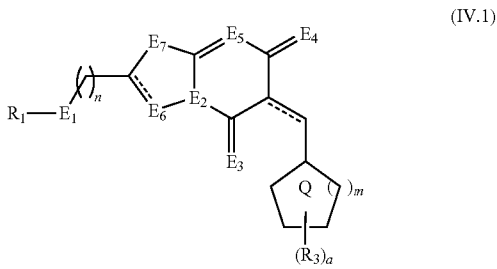

(IV.1)

or a pharmaceutically acceptable derivative thereof wherein:
R$_1$ is —(C$_3$-C$_7$)cycloalkyl, —(C$_5$-C$_{10}$)cycloalkenyl, or -(5- or 6-membered)heterocycle, each of which is unsubstituted or substituted with 1 or 2 independently selected R$_5$ groups;
each R$_3$ is independently selected from:
(a) -halo, —CN, —NO$_2$; or
(b) —OT$_3$, —OC(=O)T$_3$, —OC(=O)N(T$_1$)(T$_2$), —OC(=O)OT$_3$; or
(c) —C(=O)T$_3$, —C(=O)OT$_3$, —C(=O)N(T$_1$)(T$_2$); or
(d) —ST$_3$, —S(=O)T$_3$, —S(=O)$_2$T$_3$, —S(=O)$_2$OT$_3$, —S(=O)$_2$N(T$_1$)(T$_2$), —S(=O)OT$_3$, —S(=O)N(T$_1$)(T$_2$); or
(e) —N(T$_1$)(T$_2$), —N(T$_3$)N(T$_1$)(T$_2$), —N(T$_3$)C(=O)T$_3$, —N(T$_3$)C(=O)OT$_3$, —N(T$_3$)C(=O)N(T$_1$)(T$_2$), —N(T$_3$)S(=O)$_2$T$_3$, —N(T$_3$)S(=O)$_2$N(T$_1$)(T$_2$), —N(T$_3$)S(=O)T$_3$, —N(T$_3$)S(=O)N(T$_1$)(T$_2$); or
(f) —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_6$-C$_{14}$)bicycloalkyl, each of which is unsubstituted or substituted with 1, 2 or 3 independently selected R$_5$ groups; or
(g) -phenyl or -(5- or 6-membered)heteroaryl, each of which is unsubstituted or substituted with 1, 2 or 3 independently selected R$_6$ groups;

E$_1$ is selected from —C(O)—, —C(=O)O—, —C(=O)NH—, —S(=O)—, —S(=O)$_2$—, —S(=O)O—, or —S(=O)NH—;
E$_2$ is selected from C(T$_3$) or N;
E$_3$ and E$_4$ are each independently selected from C(T$_3$)$_2$, O, S or NT$_3$;
E$_5$ is selected from CT$_3$, or N;
the dashed lines each denote the presence or absence of a bond, wherein E$_6$ is selected from C(T$_3$)$_2$, O, S or NT$_3$ if the bond is absent, and E$_6$ is selected from CT$_3$, or N if the bond is present;
E$_7$ is selected from C(T$_3$)$_2$, O, S or NT$_3$;
n is an integer selected from 0, 1, or 2;
m is an integer selected from 1 or 2; wherein:
(a) if m=1, the ring denoted as Q is -(5-membered)heteroaryl containing 1 or 2 nitrogen atoms in place of a ring carbon atom; and
(b) if m=2, the ring denoted as Q is -phenyl or -(6-membered)heteroaryl containing 1 or 2 nitrogen atoms in place of a ring carbon atom;
a is an integer selected from 1, 2, or 3;
each R$_5$ is independently selected from —(C$_1$-C$_3$)alkyl, —(C$_2$-C$_3$)alkenyl, —(C$_2$-C$_3$)alkynyl, —(C$_1$-C$_3$)alkylCOOR$_7$, —OR$_7$, —SR$_7$, —C(halo)$_3$, —CH(halo)$_2$, —CH$_2$(halo), —CN, =O, =S, -halo, —N$_3$, —NO$_2$, —N(R$_7$)$_2$, —N(R$_7$)OH, —C(=O)R$_7$, —C(=O)OR$_7$, —OC(=O)R$_7$, —S(=O)R$_7$, or —S(=O)$_2$R$_7$;
each R$_6$ is independently selected from —(C$_1$-C$_3$)alkyl, —(C$_2$-C$_3$)alkenyl, —(C$_2$-C$_3$)alkynyl, —OR$_7$, —SR$_7$, —C(halo)$_3$, —CH(halo)$_2$, —CH$_2$(halo), —CN, -halo, —N$_3$, —NO₂, —N(R₇)₂, —N(R₇)OH, —C(═O)R₇, —C(═O)OR₇, —OC(═O)R₇, —S(═O)R₇, or —S(═O)₂R₇;
each R₇ is independently selected from —H, —CH₃, or —CH₂CH₃;
each T₁, T₂, and T₃ is independently —H or —(C₁-C₅)alkyl which is unsubstituted or substituted with 1 or 2 independently selected R₅ groups; and
each halo is independently selected from —F, —Cl, —Br, or —I.

In a further embodiment, the present invention relates to a compound having the following general formula (IV.2):

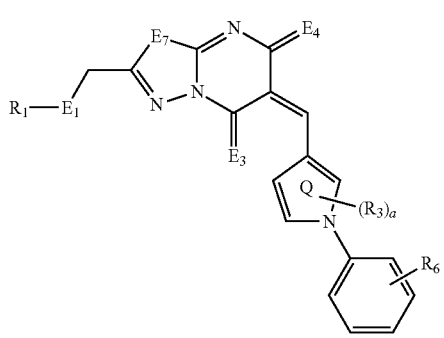

(IV.2)

or a pharmaceutically acceptable derivative thereof wherein:
R₁ is -(5- or 6-membered)heterocycle containing at least one nitrogen atom, each of which is unsubstituted or substituted with 1 or 2 independently selected R₅ groups;
each R₃ is independently selected from —(C₁-C₃)alkyl, —(C₂-C₃)alkenyl, —(C₂-C₃)alkynyl, or —(C₁-C₃)alkoxy;
each R₆ is independently selected from —C(halo)₃, —CH(halo)₂, —CH₂(halo), or -halo;
a is an integer selected from 1 or 2;
E₁ is selected from —C(O)—, —C(═O)O—, —C(═O)NH—, —S(═O)—, or —S(═O)₂—;
E₃ and E₄ are each independently selected from O, S or NT₃;
E₇ is selected from CH₂, O or S;
the 5-membered ring denoted as Q is a -(5-membered) heteroaryl containing at least one nitrogen atom at the position as depicted in formula (IV.2);
R₅ is selected from —H, —(C₁-C₂)alkyl, —(C₂)alkenyl, —(C₂)alkynyl, —OR₇, —SR₇, —C(halo)₃, —CH(halo)₂, —CH₂(halo), —CN, -halo, —N₃, —NO₂, —N(R₇)₂, —N(R₇)OH, —C(═O)R₇, —C(═O)OR₇, —S(═O)R₇, or —S(═O)₂R₇;
each R₇ is independently selected from —H, or —CH₃;
each T₃ is independently selected from —H or —CH₃; and
each halo is independently selected from —F, —Cl, —Br, or —I.

In an optional embodiment, the present invention relates to a compound having the general formula (IV.2) or a pharmaceutically acceptable derivative thereof, wherein R₁ is:

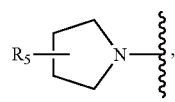

wherein R₅ is defined as above.

In an optional embodiment, the present invention relates to a compound having the general formula (IV.2) or a pharmaceutically acceptable derivative thereof, wherein R₁ is:

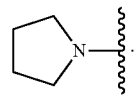

In an optional embodiment, the present invention relates to a compound having the general formula (IV.2) or a pharmaceutically acceptable derivative thereof, wherein E₁ is —C(O)—.

In an optional embodiment, the present invention relates to a compound having the general formula (IV.2) or a pharmaceutically acceptable derivative thereof, wherein E₃ is NT₃, wherein T₃ is selected from —H or —CH₃.

In an optional embodiment, the present invention relates to a compound having the general formula (IV.2) or a pharmaceutically acceptable derivative thereof, wherein E₃ is NH.

In an optional embodiment, the present invention relates to a compound having the general formula (IV.2) or a pharmaceutically acceptable derivative thereof, wherein E₄ is O.

In an optional embodiment, the present invention relates to a compound having the general formula (IV.2) or a pharmaceutically acceptable derivative thereof, wherein E₇ is S.

In an optional embodiment, the present invention relates to a compound having the general formula (IV.2) or a pharmaceutically acceptable derivative thereof, wherein E₁ is —C(O)—, E₃ is NH, E₄ is O and E₇ is S.

In an optional embodiment, the present invention relates to a compound having the general formula (IV.2) or a pharmaceutically acceptable derivative thereof, wherein each R₃ is independently selected from —(C₁-C₃)alkyl, optionally —CH₃.

In an optional embodiment, the present invention relates to a compound having the general formula (IV.2) or a pharmaceutically acceptable derivative thereof, wherein a=2.

In an optional embodiment, the present invention relates to a compound having the general formula (IV.2) or a pharmaceutically acceptable derivative thereof, wherein the 5-membered ring denoted as Q is:

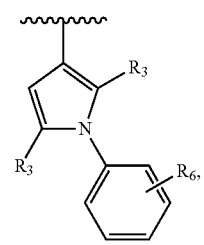

wherein R₃ and R₆ are defined as above.

In an optional embodiment, the present invention relates to a compound having the general formula (IV.2) or a pharmaceutically acceptable derivative thereof, wherein the 5-membered ring denoted as Q is:

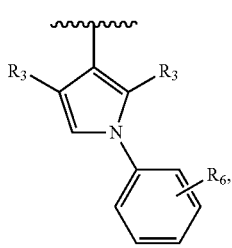

wherein $R_3$ and $R_6$ are defined as above.

In an optional embodiment, the present invention relates to a compound having the general formula (IV.2) or a pharmaceutically acceptable derivative thereof, wherein the 5-membered ring denoted as Q is:

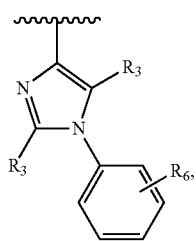

wherein $R_3$ and $R_6$ are defined as above.

In an optional embodiment, the present invention relates to a compound having the general formula (IV.2) or a pharmaceutically acceptable derivative thereof, wherein the 5-membered ring denoted as Q is:

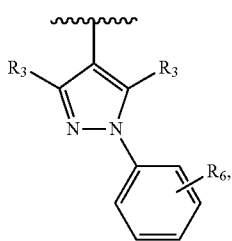

wherein $R_3$ and $R_6$ are defined as above.

In an optional embodiment, the present invention relates to a compound having the general formula (IV.2) or a pharmaceutically acceptable derivative thereof, wherein the 5-membered ring denoted as Q is:

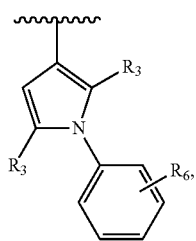

wherein each $R_3$ is —$CH_3$ and $R_6$ is defined as above.

In an optional embodiment, the present invention relates to a compound having the general formula (IV.2) or a pharmaceutically acceptable derivative thereof, wherein halo is —Cl.

In an optional embodiment, the present invention relates to a compound having the general formula (IV.2) or a pharmaceutically acceptable derivative thereof, wherein the phenyl group comprising —$R_6$ is substituted as follows:

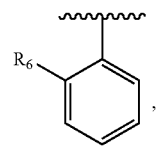

wherein $R_6$ is defined as above.

In an optional embodiment, the present invention relates to a compound having the general formula (IV.2) or a pharmaceutically acceptable derivative thereof, wherein the phenyl group comprising —$R_6$ is substituted as follows:

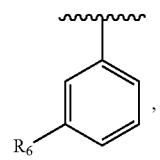

wherein $R_6$ is defined as above.

In an optional embodiment, the present invention relates to a compound having the general formula (IV.2) or a pharmaceutically acceptable derivative thereof, wherein the phenyl group comprising —$R_6$ is substituted as follows:

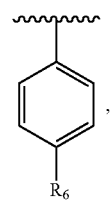

wherein $R_6$ is defined as above.

In an optional embodiment, the present invention relates to a compound having the general formula (IV.2) or a pharmaceutically acceptable derivative thereof, wherein the phenyl group comprising —$R_6$ is substituted as follows:

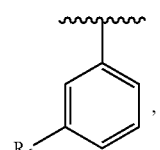

wherein $R_6$ is —Cl.

In an optional embodiment, the present invention relates to a compound having the general formula (IV.2) or a pharmaceutically acceptable derivative thereof, wherein the 5-membered ring denoted as Q is:

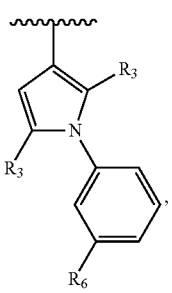

wherein $R_3$ and $R_6$ are defined as above.

In an optional embodiment, the present invention relates to a compound having the general formula (IV.2) or a pharmaceutically acceptable derivative thereof, wherein the 5-membered ring denoted as Q is:

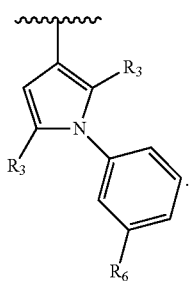

wherein $R_3$ is —$CH_3$ and $R_6$ is —Cl.

In one embodiment, the present invention relates to a compound having the following general formula (V):

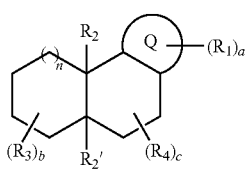

(V)

or a pharmaceutically acceptable derivative thereof wherein:
Q is selected from fused benzo or (5- or 6-membered) heteroaryl;
each $R_1$, $R_3$ and $R_4$ are each independently selected from:
 (a) -halo, —CN, —$NO_2$; or
 (b) —$OT_3$, —OC(=O)$T_3$, —OC(=O)N($T_1$)($T_2$), —OC(=O)O$T_3$; or
 (c) —C(=O)$T_3$, —C(=O)O$T_3$, —C(=O)N($T_1$)($T_2$); or
 (d) —$ST_3$, —S(=O)$T_3$, —S(=O)$_2T_3$, —S(=O)$_2OT_3$, —S(=O)$_2$N($T_1$)($T_2$), —S(=O)O$T_3$, —S(=O)N($T_1$)($T_2$); or
 (e) —N($T_1$)($T_2$), —N($T_3$)N($T_1$)($T_2$), —N($T_3$)C(=O)$T_3$, —N($T_3$)C(=O)O$T_3$, —N($T_3$)C(=O)N($T_1$)($T_2$), —N($T_3$)S(=O)$_2T_3$, —N($T_3$)S(=O)$_2$N($T_1$)($T_2$), —N($T_3$)S(=O)$T_3$, —N($T_3$)S(=O)N($T_1$)($T_2$); or
 (f) —($C_1$-$C_6$)alkyl, —($C_2$-$C_6$)alkenyl, —($C_2$-$C_6$)alkynyl, —($C_1$-$C_6$)alkoxy, —($C_3$-$C_7$)cycloalkyl, —($C_6$-$C_{14}$)bicycloalkyl, each of which is unsubstituted or substituted with 1, 2 or 3 independently selected $R_5$ groups; or
 (g) -phenyl or -(5- or 6-membered)heteroaryl, each of which is unsubstituted or substituted with 1, 2 or 3 independently selected $R_6$ groups;

a is an integer selected from 1, 2 or 3;
b is an integer selected from 1, 2 or 3;
c is an integer selected from 0, 1, 2 or 3;
$R_2$ is selected from —H and —$CH_3$;
$R_2'$ is selected from —H and —$CH_3$;
n is an integer selected from 0 or 1;
each $R_5$ is independently selected from —($C_1$-$C_4$)alkyl, —($C_2$-$C_6$)alkenyl, —($C_2$-$C_6$)alkynyl, -(5- or 6-membered) heteroaryl, -phenyl, —($C_1$-$C_6$)alkylCOO$R_7$, —$OR_7$, —$SR_7$, —C(halo)$_3$, —CH(halo)$_2$, —$CH_2$(halo), —CN, =O, =S, -halo, —$N_3$, —$NO_2$, —CH=N($R_7$), —N$R_7$($C_1$-$C_6$)alkyl-COO$R_7$, —N($R_7$)$_2$, —N($R_7$)OH, —N($R_7$)S(=O)$R_8$, —N($R_7$)S(=O)$_2R_8$, —N($R_7$)C(=O)$R_8$, —N($R_7$)C(=O)N($R_7$)$_2$, —N($R_7$)C(=O)O$R_8$, —C(=O)$R_7$, —C(=O)—C(=O)O$R_7$, —C(=O)N($R_7$)$_2$, —C(=O)O$R_7$, —OC(=O)$R_7$, —OC(=O)N($R_7$)$_2$, —OC(=O)O$R_7$, —S(=O)$R_7$, or —S(=O)$_2R_7$;

each $R_6$ is independently selected from —($C_1$-$C_4$)alkyl, —($C_2$-$C_6$)alkenyl, —($C_2$-$C_6$)alkynyl, —$OR_7$, —$SR_7$, —C(halo)$_3$, —CH(halo)$_2$, —$CH_2$(halo), —CN, -halo, —$N_3$, —$NO_2$, —CH=N($R_7$), —N($R_7$)$_2$, —N($R_7$)OH, —N($R_7$)S(=O)$R_8$, —N($R_7$)S(=O)$_2R_8$, —N($R_7$)C(=O)$R_8$, —N($R_7$)C(=O)N($R_7$)$_2$, —N($R_7$)C(=O)O$R_8$, —C(=O)$R_7$, —C(=O)N($R_7$)$_2$, —C(=O)O$R_7$, —OC(=O)$R_7$, —OC(=O)N($R_7$)$_2$, —OC(=O)O$R_7$, —S(=O)$R_7$, or —S(=O)$_2R_7$;

each $R_7$ is independently selected from —H, —($C_1$-$C_6$)alkyl, —($C_2$-$C_6$)alkenyl, —($C_2$-$C_6$)alkynyl, —($C_1$-$C_6$)alkoxy, —($C_3$-$C_8$)cycloalkyl, —($C_5$-$C_8$)cycloalkenyl, -phenyl, -benzyl, -(3- to 6-membered)heterocycle, -(5- to 10-membered)heteroaryl, —C(halo)$_3$, —CH(halo)$_2$, or —$CH_2$(halo);

each $R_8$ is independently selected from —H or —($C_1$-$C_4$)alkyl;

each $T_1$, $T_2$, and $T_3$ is independently —H or —($C_1$-$C_{10}$)alkyl which is unsubstituted or substituted with 1, 2 or 3 independently selected $R_5$ groups;

each halo is independently selected from —F, —Cl, —Br, or —I.

In a further embodiment, the present invention relates to a compound having the following general formula (V.1):

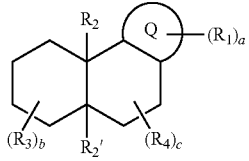

(V.1)

or a pharmaceutically acceptable derivative thereof wherein:
Q is selected from fused benzo or 6-membered heteroaryl;
each $R_1$ is independently selected from:
 (a) -halo, —CN, —$NO_2$; or
 (b) —$OT_3$, —OC(=O)$T_3$; or
 (c) —C(=O)$T_3$, —C(=O)O$T_3$, —C(=O)N($T_1$)($T_2$); or
 (d) —$ST_3$, —S(=O)$T_3$, —S(=O)$_2T_3$, —S(=O)$_2OT_3$; or
 (e) —($C_1$-$C_4$)alkyl, —($C_2$-$C_4$)alkenyl, —($C_2$-$C_4$)alkynyl, —($C_1$-$C_4$)alkoxy, each of which is unsubstituted or substituted with 1 or 2 independently selected $R_5$ groups;

each $R_3$ is independently selected from:
 (a) -halo, —CN, —$NO_2$; or
 (b) —$OT_3$, —OC(=O)$T_3$; or
 (c) —C(=O)$T_3$, —C(=O)O$T_3$, —C(=O)N($T_1$)($T_2$); or (d) —ST₃, —S(═O)T₃, —S(═O)₂T₃, —S(═O)₂OT₃; or
(e) —(C₁-C₄)alkyl, —(C₂-C₄)alkenyl, —(C₂-C₄)alkynyl, —(C₁-C₄)alkoxy, each of which is unsubstituted or substituted with 1 or 2 independently selected R₅ groups;

each R₄ is independently selected from:
(a) -halo, —CN, —NO₂; or
(b) —OT₃, —OC(═O)T₃; or
(c) —C(═O)T₃, —C(═O)OT₃, —C(═O)N(T₁)(T₂); or
(d) —ST₃, —S(═O)T₃, —S(═O)₂T₃, —S(═O)₂OT₃; or
(e) —(C₁-C₄)alkyl, —(C₂-C₄)alkenyl, —(C₂-C₄)alkynyl, —(C₁-C₄)alkoxy, each of which is unsubstituted or substituted with 1 or 2 independently selected R₅ groups;

a is an integer selected from 1 or 2;
b is an integer selected from 1 or 2;
c is an integer selected from 0 or 1;
R₂ is selected from —H and —CH₃;
R₂' is selected from —H and —CH₃;
each R₅ is independently selected from —(C₁-C₃)alkyl, —(C₂-C₃)alkenyl, —(C₂-C₃)alkynyl, —(C₁-C₃)alkyl-COOR₇, —OR₇, —SR₇, —C(halo)₃, —CH(halo)₂, —CH₂(halo), —CN, ═O, ═S, -halo, —N₃, —NO₂, —N(R₇)₂, —N(R₇)OH, —C(═O)R₇, —C(═O)OR₇, —OC(═O)R₇, —S(═O)R₇, or —S(═O)₂R₇;
each R₆ is independently selected from —(C₁-C₃)alkyl, —(C₂-C₃)alkenyl, —(C₂-C₃)alkynyl, —OR₇, —SR₇, —C(halo)₃, —CH(halo)₂, —CH₂(halo), —CN, -halo, —N₃, —NO₂, —N(R₇)₂, —N(R₇)OH, —C(═O)R₇, —C(═O)OR₇, —OC(═O)R₇, —S(═O)R₇, or —S(═O)₂R₇;
each R₇ is independently selected from —H, —CH₃, or —CH₂CH₃;
each T₁, T₂, and T₃ is independently —H or —(C₁-C₅)alkyl which is unsubstituted or substituted with 1 or 2 independently selected R₅ groups; and
each halo is independently selected from —F, —Cl, —Br, or —I.

In a further embodiment, the present invention relates to a compound having the following general formula (V.2):

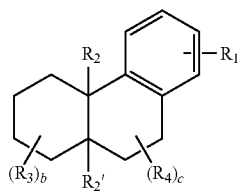

(V.2)

or a pharmaceutically acceptable derivative thereof wherein:
R₁ is selected from —(C₁-C₄)alkyl, —(C₂-C₄)alkenyl, —(C₂-C₄)alkynyl, —(C₁-C₄)alkoxy, each of which is unsubstituted or substituted with 1 or 2 independently selected R₅ groups;
R₂ is selected from —H and —CH₃;
R₂' is selected from —H and —CH₃;
each R₃ is independently selected from:
(a) —OT₃, —OC(═O)T₃; or
(b) —C(═O)T₃, —C(═O)OT₃, —C(═O)N(T₁)(T₂); or
(c) —(C₁-C₃)alkyl, —(C₂-C₃)alkenyl, —(C₂-C₃)alkynyl, —(C₁-C₃)alkoxy;
each R₄ is independently selected from:
(a) -halo, —CN, —NO₂; or
(b) —OT₃, —OC(═O)T₃; or
(c) —C(═O)T₃, —C(═O)OT₃; or
(d) —ST₃, —S(═O)T₃, —S(═O)₂T₃, —S(═O)₂OT₃; or
(e) —(C₁-C₄)alkyl, —(C₂-C₄)alkenyl, —(C₂-C₄)alkynyl, —(C₁-C₄)alkoxy;

each R₅ is independently selected from —H, —(C₁-C₂)alkyl, —(C₂)alkenyl, —(C₂)alkynyl, —OR₇, —SR₇, —C(halo)₃, —CH(halo)₂, —CH₂(halo), —CN, -halo, —N₃, —NO₂, —N(R₇)₂, —N(R₇)OH, —C(═O)R₇, —C(═O)OR₇, —S(═O)R₇, or —S(═O)₂R₇;
b is an integer selected from 1 or 2;
c is an integer selected from 0 or 1;
each R₇ is independently selected from —H, or —CH₃;
each T₁, T₂, and T₃ is independently selected from —H or —CH₃; and
each halo is independently selected from —F, —Cl, —Br, or —I.

In an optional embodiment, the present invention relates to a compound having the general formula (V.2) or a pharmaceutically acceptable derivative thereof, wherein the fused benzo is substituted as follows:

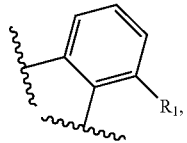

wherein R₁ is defined as above.

In an optional embodiment, the present invention relates to a compound having the general formula (V.2) or a pharmaceutically acceptable derivative thereof, wherein the fused benzo is substituted as follows:

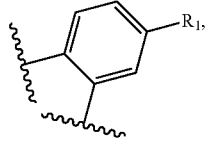

wherein R₁ is defined as above.

In an optional embodiment, the present invention relates to a compound having the general formula (V.2) or a pharmaceutically acceptable derivative thereof, wherein the fused benzo is substituted as follows:

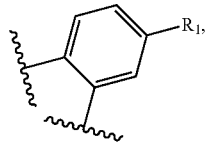

wherein R₁ is —(C₁-C₄)alkyl, optionally isopropyl.

In an optional embodiment, the present invention relates to a compound having the general formula (V.2) or a pharmaceutically acceptable derivative thereof, wherein R₁ is —(C₁-C₄)alkyl, optionally isopropyl.

In an optional embodiment, the present invention relates to a compound having the general formula (V.2) or a pharmaceutically acceptable derivative thereof, wherein the octahydrophenanthrene ring is substituted as follows:

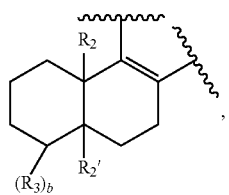

wherein $R_3$, $R_2$, $R_2'$ and b are defined as above.

In an optional embodiment, the present invention relates to a compound having the general formula (V.2) or a pharmaceutically acceptable derivative thereof, wherein the octahydrophenanthrene ring is substituted as follows:

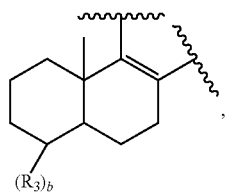

wherein $R_3$ and b are defined as above.

In an optional embodiment, the present invention relates to a compound having the general formula (V.2) or a pharmaceutically acceptable derivative thereof, wherein the octahydrophenanthrene ring is substituted as follows:

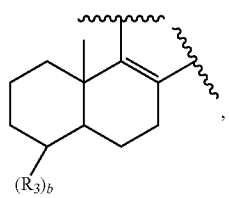

wherein $R_3$ and b=2.

In an optional embodiment, the present invention relates to a compound having the general formula (V.2) or a pharmaceutically acceptable derivative thereof, wherein b=2.

In an optional embodiment, the present invention relates to a compound having the general formula (V.2) or a pharmaceutically acceptable derivative thereof, wherein $R_2$ is —$CH_3$.

In an optional embodiment, the present invention relates to a compound having the general formula (V.2) or a pharmaceutically acceptable derivative thereof, wherein $R_2'$ is —H.

In an optional embodiment, the present invention relates to a compound having the general formula (V.2) or a pharmaceutically acceptable derivative thereof, wherein $R_2$ is —$CH_3$ and $R_2'$ is —H.

In an optional embodiment, the present invention relates to a compound having the general formula (V.2) or a pharmaceutically acceptable derivative thereof, wherein b=2 and one $R_3$ is —C(=O)$OT_3$ or —C(=O)NH-$T_3$ and the other $R_3$ is —($C_1$-$C_3$)alkyl, and wherein $T_3$ is —H or —$CH_3$.

In an optional embodiment, the present invention relates to a compound having the general formula (V.2) or a pharmaceutically acceptable derivative thereof, wherein c=0.

In an optional embodiment, the present invention relates to a compound having the general formula (V.2) or a pharmaceutically acceptable derivative thereof, wherein the octahydrophenanthrene ring is substituted as follows:

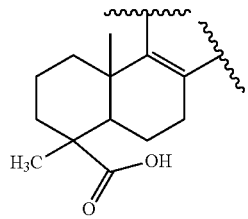

In an optional embodiment, the present invention relates to a compound having the general formula (V.2) or a pharmaceutically acceptable derivative thereof, wherein the octahydrophenanthrene ring is substituted as follows:

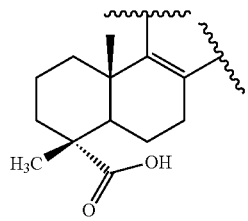

In an optional embodiment, the present invention relates to a compound having the general formula (V.2) or a pharmaceutically acceptable derivative thereof, wherein the octahydrophenanthrene ring is substituted as follows:

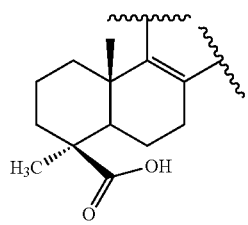

In an optional embodiment, the present invention relates to a compound having the general formula (V.2) or a pharmaceutically acceptable derivative thereof, wherein the octahydrophenanthrene ring is substituted as follows:

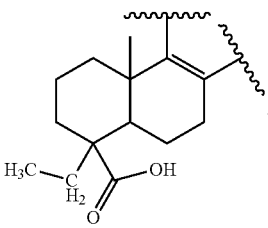

In an optional embodiment, the present invention relates to a compound having the general formula (V.2) or a pharmaceutically acceptable derivative thereof, wherein the octahydrophenanthrene ring is substituted as follows:

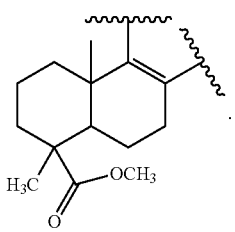

Exemplified Compounds

In an optional embodiment, the present invention relates to the compounds depicted in Table 1 or a pharmaceutically acceptable derivative thereof.

TABLE 1

| Compound | Chemical structure |
|---|---|
| I.3 | 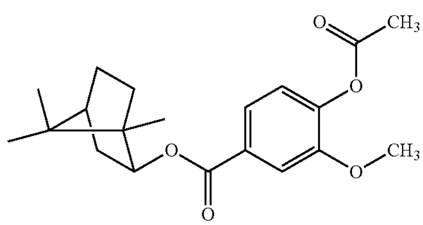 |
| II.3 | 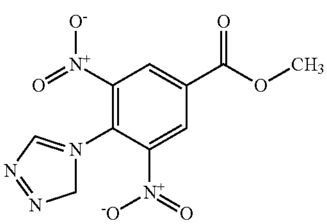 |
| III.3 | 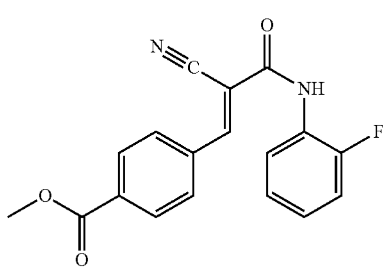 [SMILES: COC(=O)c1ccc(/C=C(\C#N)C(=O)Nc2ccccc2F)cc1] |
| IV.3 | 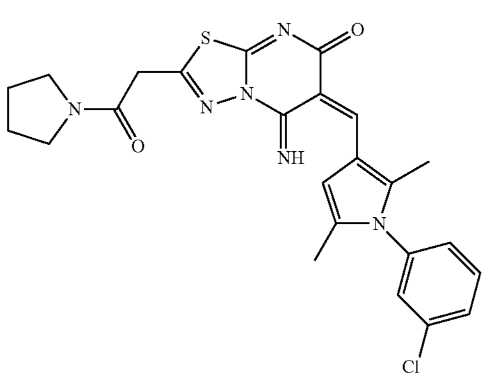 [SMILES: Cc1cc(/C=C2\C(=N)N3N=C(CC(=O)N4CCCC4)SC3=NC2=O)c(C)n1-c1cccc(Cl)c1] |

TABLE 1-continued

| Compound | Chemical structure |
|---|---|
| V.3 | 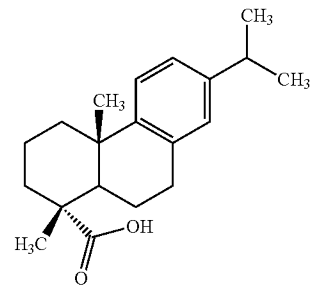 [SMILES: CC(C)c1ccc2c(c1)CCC1[C@](C)(C(=O)O)CCC[C@]21C] |

In an optional embodiment, the present invention relates to a compound having the general formula (I.2) or (I.2.1) or a pharmaceutically acceptable derivative thereof, where Compound (I.3) is excluded.

In an optional embodiment, the present invention relates to a compound having the general formula (II.2) or a pharmaceutically acceptable derivative thereof, where Compound (II.3) is excluded.

In an optional embodiment, the present invention relates to a compound having the general formula (III.2) or a pharmaceutically acceptable derivative thereof, where Compound (III.3) is excluded.

In an optional embodiment, the present invention relates to a compound having the general formula (IV.2) or a pharmaceutically acceptable derivative thereof, where Compound (IV.3) is excluded.

In an optional embodiment, the present invention relates to a compound having the general formula (V.2) or a pharmaceutically acceptable derivative thereof, where Compound (V.3) is excluded.

DEFINITIONS

As used in connection with the Compounds herein, the terms used herein having following meaning:

When a first group is "substituted with one or more" second groups, one or more hydrogen atoms of the first group is replaced with a corresponding number of second groups. When the number of second groups is two or greater, each second group can be the same or different. In one embodiment, a first group is substituted with up to three second groups. In another embodiment, a first group is substituted with one or two second groups. In another embodiment, a first group is substituted with only one second group.

"—($C_1$-$C_{10}$)alkyl" means a straight chain or branched non-cyclic hydrocarbon having from 1 to 10 carbon atoms. Representative straight chain —($C_1$-$C_{10}$)alkyls include -methyl, -ethyl, -n-propyl, -n-butyl, -n-pentyl, -n-hexyl, -n-heptyl, -n-octyl, -n-nonyl, and -n-decyl. A branched alkyl means that one or more straight chain —($C_1$-$C_8$)alkyl groups, such as methyl, ethyl or propyl, replace one or both hydrogens in a —$CH_2$— group of a straight chain alkyl. A branched non-cyclic hydrocarbon means that one or more straight chain —($C_1$-$C_{10}$)alkyl groups, such as methyl, ethyl or propyl, replace one or both hydrogens in a —$CH_2$— group of a straight chain non-cyclic hydrocarbon. Representative branched —($C_1$-$C_{10}$)alkyls include -iso-propyl, -sec-butyl, -iso-butyl, -tert-butyl, -iso-pentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

"—$(C_1-C_6)$alkyl" means a straight chain or branched non-cyclic hydrocarbon having from 1 to 6 carbon atoms. Representative straight chain —$(C_1-C_6)$alkyls include -methyl, -ethyl, -n-propyl, -n-butyl, -n-pentyl, and -n-hexyl. Representative branched —$(C_1-C_6)$alkyls include -iso-propyl, -sec-butyl, -iso-butyl, -tert-butyl, -iso-pentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, and 3,3-dimethylbutyl.

"—$(C_1-C_4)$alkyl" means a straight chain or branched non-cyclic hydrocarbon having from 1 to 4 carbon atoms. Representative straight chain —$(C_1-C_4)$alkyls include -methyl, -ethyl, -n-propyl, and -n-butyl. Representative branched —$(C_1-C_4)$alkyls include -iso-propyl, -sec-butyl, -iso-butyl, and -tert-butyl.

"—$(C_1-C_3)$alkyl" means a straight chain or branched non-cyclic hydrocarbon having from 1 to 3 carbon atoms. Representative straight chain —$(C_1-C_3)$alkyls include -methyl, -ethyl, and -n-propyl. Representative branched —$(C_1-C_3)$alkyls include -iso-propyl.

"—$(C_1-C_2)$alkyl" means a straight chain non-cyclic hydrocarbon having 1 or 2 carbon atoms. Representative straight chain —$(C_1-C_2)$alkyls include -methyl and -ethyl.

"—$(C_2-C_{10})$alkenyl" means a straight chain or branched non-cyclic hydrocarbon having from 2 to 10 carbon atoms and including at least one carbon-carbon double bond. A branched alkenyl means that one or more straight chain —$(C_1-C_8)$alkyl groups, such as methyl, ethyl or propyl, replace one or both hydrogens in a —CH$_2$— or —CH= group of a straight chain alkenyl. Representative straight chain and branched $(C_2-C_{10})$alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl, and the like.

"—$(C_2-C_6)$alkenyl" means a straight chain or branched non-cyclic hydrocarbon having from 2 to 6 carbon atoms and including at least one carbon-carbon double bond. Representative straight chain and branched $(C_2-C_6)$alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, 2-hexenyl, 3-hexenyl, and the like.

"—$(C_2-C_4)$alkenyl" means a straight chain or branched non-cyclic hydrocarbon having from 2 to 4 carbon atoms and including at least one carbon-carbon double bond. Representative $(C_2-C_4)$alkenyls include -vinyl, -allyl, -1-butenyl, -2-butenyl, -iso-butylenyl, and the like.

"—$(C_2-C_3)$alkenyl" means a straight chain or branched non-cyclic hydrocarbon having from 2 to 3 carbon atoms and including at least one carbon-carbon double bond. Representative $(C_2-C_3)$alkenyls include -vinyl, -allyl, and the like.

"—$(C_2)$alkenyl" means a straight chain non-cyclic hydrocarbon having 2 carbon atoms and including one carbon-carbon double bond.

"—$(C_2-C_{10})$alkynyl" means a straight chain or branched non-cyclic hydrocarbon having from 2 to 10 carbon atoms and including at least one carbon-carbon triple bond. A branched alkynyl means that one or more straight chain —$(C_1-C_8)$alkyl groups, such as methyl, ethyl or propyl, replace one or both hydrogens in a —CH$_2$— group of a straight chain alkynyl. Representative straight chain and branched —$(C_2-C_{10})$alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like.

"—$(C_2-C_6)$alkynyl" means a straight chain or branched non-cyclic hydrocarbon having from 2 to 6 carbon atoms and including at least one carbon-carbon triple bond. Representative straight chain and branched $(C_2-C_6)$alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, and the like.

"—$(C_2-C_4)$alkynyl" means a straight chain or branched non-cyclic hydrocarbon having from 2 to 4 carbon atoms and including at least one carbon-carbon triple bond. Representative $(C_2-C_4)$alkynyls include -acetylenyl, -propynyl, -1-butynyl, -2-butynyl, and the like.

"—$(C_2-C_3)$alkynyl" means a straight chain or branched non-cyclic hydrocarbon having from 2 to 3 carbon atoms and including at least one carbon-carbon triple bond. Representative $(C_2-C_3)$alkynyls include -acetylenyl, -propynyl, and the like.

"—$(C_2)$alkynyl" means a straight chain non-cyclic hydrocarbon having 2 carbon atoms and including one carbon-carbon triple bond.

"—$(C_1-C_6)$alkoxy" means a straight chain or branched non-cyclic hydrocarbon having one or more ether groups and from 1 to 6 carbon atoms. Representative straight chain and branched $(C_1-C_6)$alkoxys include -methoxy, -ethoxy, methoxymethyl, 2-methoxyethyl, -5-methoxypentyl, 3-ethoxybutyl and the like.

"—$(C_1-C_4)$alkoxy" means a straight chain or branched non-cyclic hydrocarbon having one or more ether groups and from 1 to 4 carbon atoms. Representative $(C_1-C_4)$ alkoxys include -methoxy, -ethoxy, methoxymethyl, 2-methoxyethyl, and the like.

"—$(C_1-C_3)$alkoxy" means a straight chain or branched non-cyclic hydrocarbon having one or more ether groups and from 1 to 3 carbon atoms. Representative $(C_1-C_3)$ alkoxys include -methoxy, -ethoxy, methoxymethyl, 2-methoxyethyl, and the like.

"—$(C_3-C_{20})$cycloalkyl" means a saturated monocyclic hydrocarbon having from 3 to 20 carbon atoms. Representative $(C_3-C_{20})$cycloalkyls are -cyclopropyl, -cyclobutyl, -cyclopentyl, -cyclohexyl, -cycloheptyl, -cyclooctyl, -cyclononyl, -cyclodecyl, cycloundecyl, and -cyclododecyl, and -cyclotetradecyl.

"—$(C_3-C_{14})$cycloalkyl" means a saturated monocyclic hydrocarbon having from 3 to 14 carbon atoms. Representative $(C_3-C_{14})$cycloalkyls are -cyclopropyl, -cyclobutyl, -cyclopentyl, -cyclohexyl, -cycloheptyl, -cyclooctyl, -cyclononyl, -cyclodecyl, cycloundecyl, and -cyclododecyl, and -cyclotetradecyl.

"—$(C_3-C_{12})$cycloalkyl" means a saturated monocyclic hydrocarbon having from 3 to 12 carbon atoms. Representative ($C_3$-$C_{12}$)cycloalkyls are -cyclopropyl, -cyclobutyl, -cyclopentyl, -cyclohexyl, -cycloheptyl, -cyclooctyl, -cyclononyl, -cyclodecyl, cycloundecyl, and -cyclododecyl.

"—($C_6$-$C_{12}$)cycloalkyl" means a saturated monocyclic hydrocarbon having from 6 to 12 carbon atoms. Representative ($C_6$-$C_{12}$)cycloalkyls are -cyclohexyl, -cycloheptyl, -cyclooctyl, -cyclononyl, -cyclodecyl, cycloundecyl, and -cyclododecyl.

"—($C_4$-$C_8$)cycloalkyl" or "4- to 8-member cycloalkyl ring" means a saturated monocyclic hydrocarbon having from 4 to 8 carbon atoms. Representative —($C_4$-$C_8$)cycloalkyls are -cyclobutyl, -cyclopentyl, -cyclohexyl, -cycloheptyl, and -cyclooctyl.

"—($C_5$)cycloalkyl" or "5-member cycloalkyl ring" means a saturated monocyclic hydrocarbon having 5 carbon atoms (i.e. -cyclopentyl).

"—($C_6$)cycloalkyl" or "6-member cycloalkyl ring" means a saturated monocyclic hydrocarbon having 6 carbon atoms (i.e. -cyclohexyl).

"—($C_7$)cycloalkyl" or "7-member cycloalkyl ring" means a saturated monocyclic hydrocarbon having 7 carbon atoms (i.e. -cycloheptyl).

"—($C_3$-$C_8$)cycloalkyl" means a saturated monocyclic hydrocarbon having from 3 to 8 carbon atoms. Representative ($C_3$-$C_8$)cycloalkyls include -cyclopropyl, -cyclobutyl, -cyclopentyl, -cyclohexyl, -cycloheptyl, and -cyclooctyl.

"—($C_3$-$C_7$)cycloalkyl" means a saturated monocyclic hydrocarbon having from 3 to 7 carbon atoms. Representative ($C_3$-$C_7$)cycloalkyls include cyclopropyl, -cyclobutyl, -cyclopentyl, -cyclohexyl, -and cycloheptyl.

"—(C6-C14)bicycloalkyl" means a bi-cyclic hydrocarbon ring system having from 6 to 14 carbon atoms and at least one saturated cyclic alkyl ring. Representative —($C_6$-$C_{14}$)bicycloalkyls include -indanyl, -norbornyl, -1,2,3,4-tetrahydronaphthalenyl, -5,6,7,8-tetrahydronaphthalenyl, -perhydronaphthalenyl, bicyclo[2.2.1]hexyl, bicyclo[2.2.1.]heptyl, bicyclo[2.2.2]octyl, bicyclo[3.3.1]heptyl, bicyclo[3.2.1]octyl, bicyclo[3.3.1]nonyl, bicyclo[3.3.2]decyl, bicyclo[3.3.3]undecyl, bicyclo[4.2.2]decyl, bicyclo[4.3.2]undecyl, bicyclo[4.3.1]decyl, and the like.

"—($C_8$-$C_{20}$)tricycloalkyl" means a tri-cyclic hydrocarbon ring system having from 8 to 20 carbon atoms and at least one saturated cyclic alkyl ring. Representative —($C_8$-$C_{20}$)tricycloalkyls include -pyrenyl, -adamantyl, noradamantyl, -1,2,3,4-tetrahydroanthracenyl, -perhydroanthracenyl -aceanthrenyl, -1,2,3,4-tetrahydropenanthrenyl, -5,6,7,8-tetrahydrophenanthrenyl, -perhydrophenanthrenyl, tetradecahydro-1H-cyclohepta[a]naphthalenyl, tetradecahydro-1H-cycloocta[e]indenyl, tetradecahydro-1H-cyclohepta[e]azulenyl, hexadecahydrocycloocta[b]naphthalenyl, hexadecahydrocyclohepta[a]heptalenyl, tricyclo-pentadecanyl, tricyclo-octadecanyl, tricyclo-nonadecanyl, tricyclo-icosanyl, and the like.

"—($C_3$-$C_{20}$)cycloalkenyl" means a cyclic non-aromatic hydrocarbon having at least one carbon-carbon double bond in the cyclic system and from 3 to 20 carbon atoms. Representative ($C_3$-$C_{20}$)cycloalkenyls include -cyclopropenyl, -cyclobutenyl, -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl, -cyclotetradecenyl, -cyclododecadienyl, and the like.

"—($C_3$-$C_{14}$)cycloalkenyl" means a cyclic non-aromatic hydrocarbon having at least one carbon-carbon double bond in the cyclic system and from 3 to 14 carbon atoms. Representative ($C_3$-$C_{14}$)cycloalkenyls include -cyclopropenyl, -cyclobutenyl, -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl, -cyclotetradecenyl, -cyclododecadienyl, and the like.

"—($C_5$-$C_{14}$)cycloalkenyl" means a cyclic non-aromatic hydrocarbon having at least one carbon-carbon double bond in the cyclic system and from 5 to 14 carbon atoms. Representative ($C_5$-$C_{14}$)cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl, -cyclotetradecenyl, -cyclododecadienyl, and the like.

"—($C_6$-$C_{12}$)cycloalkenyl" means a cyclic non-aromatic hydrocarbon having at least one carbon-carbon double bond in the cyclic system and from 6 to 12 carbon atoms. Representative ($C_6$-$C_{12}$)cycloalkenyls include -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl, -cyclodo-decadienyl, and the like.

"—($C_5$-$C_{10}$)cycloalkenyl" means a cyclic non-aromatic hydrocarbon having at least one carbon-carbon double bond in the cyclic system and from 5 to 10 carbon atoms. Representative ($C_5$-$C_{10}$)cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl, and the like.

"—($C_5$-$C_8$)cycloalkenyl" means a cyclic non-aromatic hydrocarbon having at least one carbon-carbon double bond in the cyclic system and from 5 to 8 carbon atoms. Representative ($C_5$-$C_8$)cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, and the like.

"—($C_5$)cycloalkenyl" means a cyclic non-aromatic hydrocarbon having at least one carbon-carbon double bond in the cyclic system and 5 carbon atoms. Representative ($C_5$)cycloalkenyls include -cyclopentenyl, -cyclopentadienyl, and the like.

"—($C_6$)cycloalkenyl" means a cyclic non-aromatic hydrocarbon having at least one carbon-carbon double bond in the cyclic system and 6 carbon atoms. Representative ($C_6$)cycloalkenyls include -cyclohexenyl, -cyclohexadienyl, and the like.

"—($C_7$)cycloalkenyl" means a cyclic non-aromatic hydrocarbon having at least one carbon-carbon double bond in the cyclic system and 7 carbon atoms. Representative ($C_7$)cycloalkenyls include -cycloheptenyl, -cycloheptadienyl, and the like.

"—($C_7$-$C_{14}$)bicycloalkenyl" means a bi-cyclic hydrocarbon ring system having at least one carbon-carbon double bond in each ring and from 7 to 14 carbon atoms. Representative —($C_7$-$C_{14}$)bicycloalkenyls include -bicyclo[3.2.0]hept-2-enyl, -indenyl, -pentalenyl, -naphthalenyl, -azulenyl, -heptalenyl, -1,2,7,8-tetrahydronaphthalenyl, norbornenyl, and the like.

"—($C_8$-$C_{20}$)tricycloalkenyl" means a tri-cyclic hydrocarbon ring system having at least one carbon-carbon double bond in each ring and from 8 to 20 carbon atoms.

Representative —(C$_8$-C$_{20}$)tricycloalkenyls include -anthracenyl, -phenanthrenyl, -phenalenyl, -acenaphthalenyl, as-indacenyl, s-indacenyl, 2,3,6,7,8,9,10,11-octahydro-1H-cycloocta[e]indenyl, 2,3,4,7,8,9,10,11-octahydro-1H-cyclohepta[a]naphthalenyl, 8,9,10,11-tetrahydro-7H-cyclohepta[a]naphthalenyl, 2,3,4,5,6,7,8,9,10,11,12,13-dodecahydro-1H-cyclohepta[a]heptalenyl, 1,2,3,4,5,6,7,8,9,10,11,12,13,14-tetradecahydro-dicyclohepta[a,c]cyclooctenyl, 2,3,4,5,6,7,8,9,10,11,12,13-dodecahydro-1H-dibenzo[a,c]cyclononenyl, and the like.

"-(3- to 7-membered)heterocycle" or "-(3- to 7-membered)heterocyclo" means a 3- to 7-membered monocyclic heterocyclic ring which is either saturated, unsaturated non-aromatic, or aromatic. A 3-membered heterocycle can contain up to 1 heteroatom, a 4-membered heterocycle can contain up to 2 heteroatoms, a 5-membered heterocycle can contain up to 4 heteroatoms, a 6-membered heterocycle can contain up to 4 heteroatoms, and a 7-membered heterocycle can contain up to 5 heteroatoms. Each heteroatom is independently selected from nitrogen, which can be quaternized; oxygen; and sulfur, including sulfoxide and sulfone. The -(3- to 7-membered)heterocycle can be attached via a nitrogen or carbon atom. Representative -(3- to 7-membered)heterocycles include pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

"-(5- or 6-membered)heterocycle" or "-(5- or 6-membered)heterocyclo" means a 5- or 6-membered monocyclic heterocyclic ring which is either saturated, unsaturated non-aromatic, or aromatic. A 5-membered heterocycle can contain up to 4 heteroatoms and a 6-membered heterocycle can contain up to 4 heteroatoms. Each heteroatom is independently selected from nitrogen, which can be quaternized; oxygen; and sulfur, including sulfoxide and sulfone. The -(5- or 6-membered)heterocycle can be attached via a nitrogen or carbon atom.

Representative -(5- or 6-membered)heterocycles include pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, tetrahydrofuranyl, tetrahydropyranyl, dihydropyridinyl, tetrahydropyridinyl, tetrahydropyrimidinyl, tetrahydrothiophenyl, tetrahydrothiopyranyl, tetrazolyl, and the like.

"-(3- to 5-membered)heterocycle" or "-(3- to 5-membered)heterocyclo" means a 3- to 5-membered monocyclic heterocyclic ring which is either saturated, unsaturated non-aromatic, or aromatic. A 3-membered heterocycle can contain up to 1 heteroatom, a 4-membered heterocycle can contain up to 2 heteroatoms, and a 5-membered heterocycle can contain up to 4 heteroatoms. Each heteroatom is independently selected from nitrogen, which can be quaternized; oxygen; and sulfur, including sulfoxide and sulfone. The -(3- to 5-membered)heterocycle can be attached via a nitrogen or carbon atom. Representative -(3- to 5-membered)heterocycles include furyl, thiophenyl, pyrrolyl, oxazolyl, imidazolyl, thiazolidinyl, thiadiazolyl, thiazolyl, isoxazolyl, pyrazolyl, isothiazolyl, triazinyl, pyrrolidinonyl, pyrrolidinyl, 2,3-dihydrofuranyl, hydantoinyl, oxiranyl, oxetanyl, tetrahydrofuranyl, tetrahydrothiophenyl, pyrazolidinyl and the like.

"-(7- to 10-membered)bicycloheterocycle" or "-(7- to 10-membered)bicycloheterocyclo" means a 7- to 10-membered bicyclic, heterocyclic ring which is either saturated, unsaturated non-aromatic, or aromatic. A -(7- to 10-membered)bicycloheterocycle contains from 1 to 4 heteroatoms independently selected from nitrogen, which can be quaternized; oxygen; and sulfur, including sulfoxide and sulfone. The -(7- to 10-membered)bicycloheterocycle can be attached via a nitrogen or carbon atom. Representative -(7- to 10-membered)bicycloheterocycles include -quinolinyl, -isoquinolinyl, -chromonyl, -coumarinyl, -indolyl, -indolizinyl, -benzo[b]furanyl, -benzo[b]thiophenyl, -indazolyl, -purinyl, -4H-quinolizinyl, -isoquinolyl, -quinolyl, -phthalazinyl, -naphthyridinyl, -carbazolyl, -β-carbolinyl, -indolinyl, -isoindolinyl, -1,2,3,4-tetrahydroquinolinyl, -1,2,3,4-tetrahydroisoquinolinyl, pyrrolopyrrolyl and the like.

"—(C$_3$-C$_{12}$)cycloalkoxy" means a saturated monocyclic hydrocarbon having from 3 to 12 carbon atoms where at least one of the carbon atoms is replaced by an oxygen atom. Representative (C$_3$-C$_{12}$)cycloalkoxy are -oxiranyl, -oxetanyl, -tetrahydrofuranyl, -tetrahydro-2H-pyranyl, -1,4-dioxanyl, -oxepanyl, -1,4-dioxepanyl, -oxocanyl, -1,5-dioxocanyl, -1,3,5-trioxocanyl, -oxonanyl, -1,5-dioxonanyl, -1,4,7-trioxonanyl, -oxacyclododecanyl, -1,7-dioxacyclododecanyl, and -1,5,9-trioxacyclododecanyl.

"—(C$_3$-C$_7$)cycloalkoxy" means a saturated monocyclic hydrocarbon having from 3 to 7 carbon atoms where at least one of the carbon atoms is replaced by an oxygen atom. Representative (C$_3$-C$_7$)cycloalkoxy are -oxiranyl, -oxetanyl, -tetrahydrofuranyl, -tetrahydro-2H-pyranyl, -1,4-dioxanyl, -oxepanyl, and -1,4-dioxepanyl.

"—(C$_{1-4}$)aryl" means a 14-membered aromatic carbocyclic moiety such as -anthryl or -phenanthryl.

"-(5- to 10-membered)heteroaryl" means an aromatic heterocycle ring of 5 to 10 members, including both mono- and bicyclic ring systems, where at least one carbon atom of one or both of the rings is replaced with a heteroatom independently selected from nitrogen, oxygen, and sulfur, or at least two carbon atoms of one or both of the rings are replaced with a heteroatom independently selected from nitrogen, oxygen, and sulfur. In one embodiment, one of the -(5- to 10-membered)heteroaryl's rings contain at least one carbon atom. In another embodiment, both of the -(5- to 10-membered)heteroaryl's rings contain at least one carbon atom. Representative -(5- to 10-membered)heteroaryls include pyridyl, furyl, benzofuranyl, thiophenyl, benzothiophenyl, quinolinyl, isoquinolinyl, pyrrolyl, indolyl, oxazolyl, benzoxazolyl, imidazolyl, benzimidazolyl, thiazolyl, benzothiazolyl, isoxazolyl, oxadiazolinyl, pyrazolyl, isothiazolyl, pyridazinyl, pyrimidyl, pyrimidinyl, pyrazinyl, thiadiazolyl, triazinyl, thienyl, cinnolinyl, phthalazinyl, and quinazolinyl.

"-(5- or 6-membered)heteroaryl" means a monocyclic aromatic heterocycle ring of 5 or 6 members where at least one carbon atom is replaced with a heteroatom independently selected from nitrogen, oxygen, and sulfur. In one embodiment, one of the -(5- or 6-membered)heteroaryl's ring contains at least one carbon atom. Representative -(5- or 6-membered)heteroaryls include pyridyl, furyl, pyrrolyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, pyrazolyl, isothiazolyl, pyridazinyl, pyrimidyl, pyrazinyl, 1,2,3-thiadiazolyl, 1,3,4-thiadiazolyl, 1,2,5-thiadiazolyl, 1,3,5-triazinyl, and thiophenyl.

"—CH$_2$(halo)" means a methyl group where one of the hydrogens of the methyl group has been replaced with a halogen. Representative —CH$_2$(halo) groups include —CH$_2$F, —CH$_2$Cl, —CH$_2$Br, and —CH$_2$I.

"—CH(halo)$_2$" means a methyl group where two of the hydrogens of the methyl group have been replaced with a halogen. Representative —CH(halo)$_2$ groups include —CHF$_2$, —CHCl$_2$, —CHBr$_2$, —CHBrCl, —CHClI, and —CHI$_2$.

"—C(halo)$_3$" means a methyl group where each of the hydrogens of the methyl group has been replaced with a halogen. Representative —C(halo)$_3$ groups include —CF$_3$, —CCl$_3$, —CBr$_3$, and —Cl$_3$.

"-Halogen" or "-halo" means —F, —Cl, —Br, or —I.

"Oxo", "=O", and the like as used herein mean an oxygen atom doubly bonded to carbon or another element.

"Thiooxo", "thioxo", "=S", and the like as used herein mean a sulfur atom doubly bonded to carbon or another element.

"Imino", "=NT$_3$", and the like as used herein mean a nitrogen atom doubly bonded to carbon or another element.

As used herein in connection with Formula (I.1), when the dashed lines between R13' and R14', and between R14' and R15' each denote the presence or absence of a bond, then Formula (I.1) is understood to appear as follows:

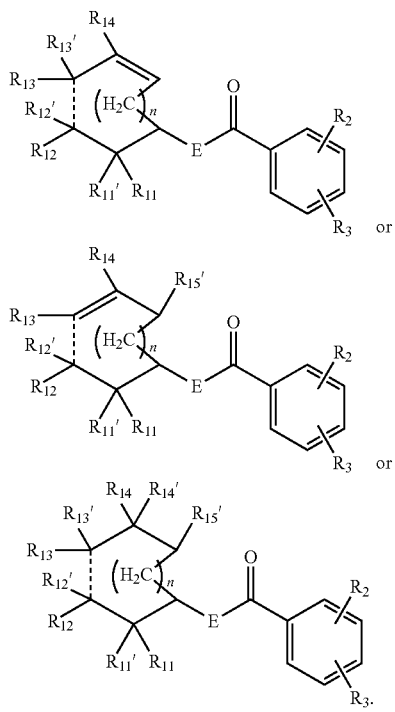

As used herein in connection with Formula (I.1), when the bond indicated by the dashed line between $R_{12}'$ and $R_{13}'$ is absent and $R_{12}'$ and $R_{13}'$ together form a —(C$_3$-C$_7$)cycloalkyl, —(C$_6$-C$_{14}$)bicycloalkyl, —(C$_5$-C$_{10}$)cycloalkenyl, —(C$_7$-C$_{14}$)bicycloalkenyl, each of which is unsubstituted or substituted with 1, 2 or 3 independently selected R$_5$ groups, then Formula (I.1) is e.g. understood to appear as follows if $R_{12}'$ and $R_{13}'$ together form a —(C$_6$)cycloalkenyl:

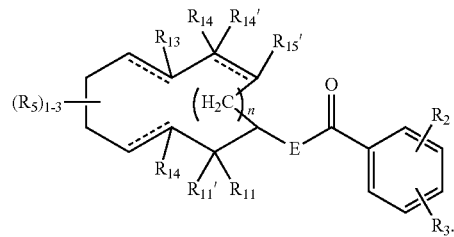

As used herein in connection with Formula (I.1.1) and R$_1$=(i), when the dashed lines between R$_{13}$' and R$_{14}$' and R$_{14}$' and R$_{15}$' each denote the presence or absence of a bond, then R$_1$ of Formula (I.1.1) is understood to appear as follows:

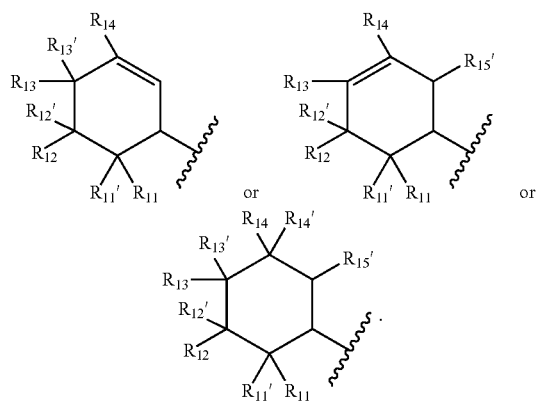

As used herein in connection with Formula (I.1.1) and Ri=(i), when R$_{11}$' and R$_{14}$' together form a (C$_1$-C$_2$) bridge which is unsubstituted or substituted with 1, 2, 3 or 4 substituents independently selected from —OH, —(C$_1$-C$_4$) alkyl, -halo, and —C(halo)$_3$, then R$_1$ of Formula (III) is understood to appear as follows:

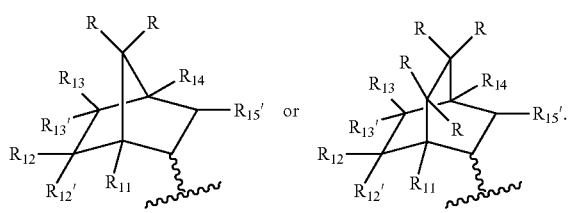

As used herein in connection with Formula (I.1.1) or (I.2.1) and Ri=(ii), when the dashed line between R$_{14}$' and R$_{15}$' denotes the presence or absence of a bond, then R$_1$ of Formula (I.1.1) or (I.2.1) is understood to appear as follows:

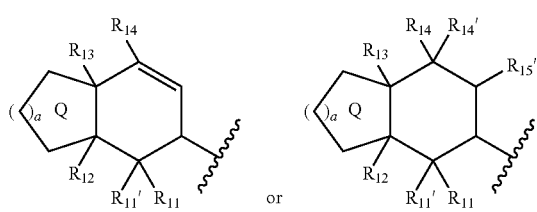

wherein Q is defined as above.

As used herein in connection with Formula (I.1.1) and $R_1$=(iii), when the dashed line between $R_{14}'$ and $R_{15}'$ denotes the presence or absence of a bond, then $R_1$ of Formula (I.1.1) is understood to appear as follows:

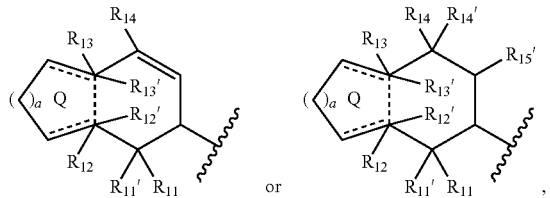

wherein Q is defined as above.

As used herein in connection with Formula (I.1.1) and Ri=(iii), when the dashed line between $R_{12}$ and $R_{13}$ denotes the absence of a bond, and the dashed lines together with the solid lines in the ring denoted as Q each independently denote the presence or absence of a double bond, wherein $R_{12}'$ is absent if the carbon atom carrying $R_{12}'$ is unsaturated, and wherein $R_{13}'$ is absent if the carbon atom carrying $R_{13}'$ is unsaturated, then $R_1$ of Formula (I.1.1) is understood to appear as follows:

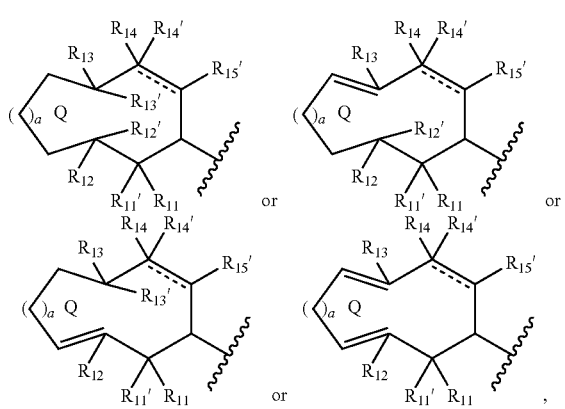

wherein Q is defined as above.

As used herein in connection with Formula (I.1.1) or (I.2.1) and Ri=(iv), when the dashed lines between $R_{13}'$ and $R_{14}'$ and $R_{14}'$ and $R_{15}'$ each denote the presence or absence of a bond, then $R_1$ of Formula (I.1.1) or (I.2.1) is understood to appear as follows:

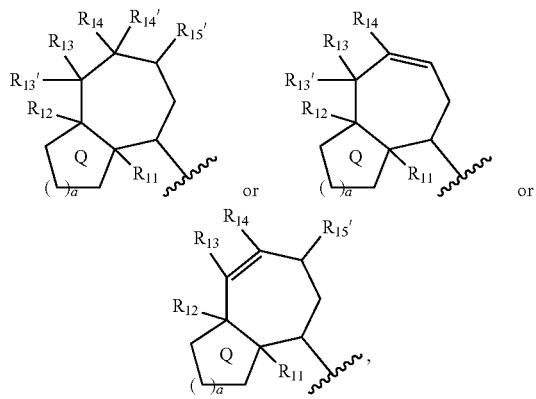

wherein Q is defined as above.

As used herein in connection with Formula (I.2), when the dashed line between $R_{14}'$ and $R_{15}'$ denotes the presence or absence of a bond, then Formula (I.2) is understood to appear as follows:

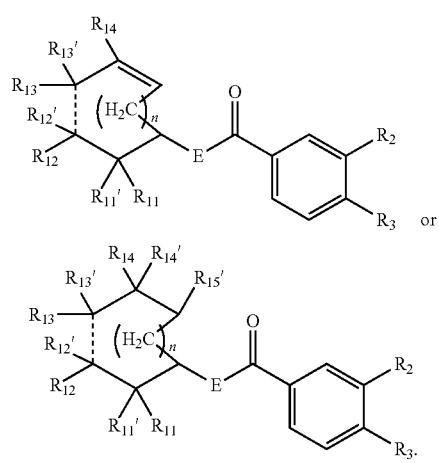

As used herein in connection with Formula (I.2), when n=0 and $R_{12}'$ and $R_{13}'$ together form a —$(C_5-C_7)$cycloalkyl or —$(C_5-C_7)$cycloalkenyl, each of which is unsubstituted or substituted with 1, 2, 3 or 4 independently selected $R_5$ groups, and wherein the bond indicated by the dashed line between $R_{12}'$ and $R_{13}'$ can be present or absent, then Formula (I.2) is understood to appear as follows:

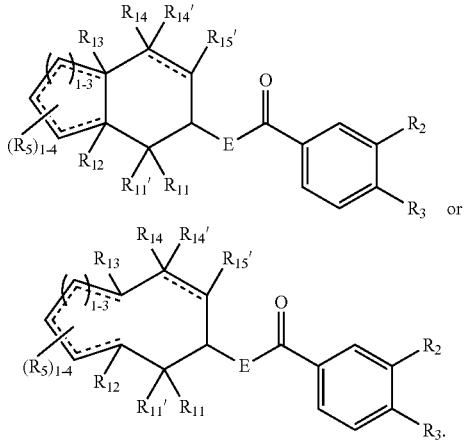

As used herein in connection with Formula (I.2.1) and Ri=(iii), when the dashed line between $R_{14}'$ and $R_{15}'$ denotes the presence or absence of a bond, then $R_1$ of Formula (I.2.1) is understood to appear as follows:

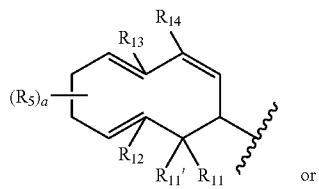

or

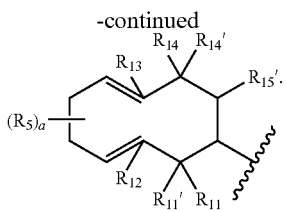

As used herein in connection with Formula (III), when the dashed line denotes the presence or absence of a bond, then Formula (III) is understood to appear as follows:

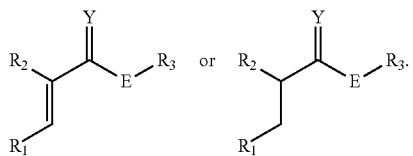

As used herein in connection with Formula (IV), when the dashed lines each denote the presence or absence of a bond, then Formula (IV) is understood to appear as follows:

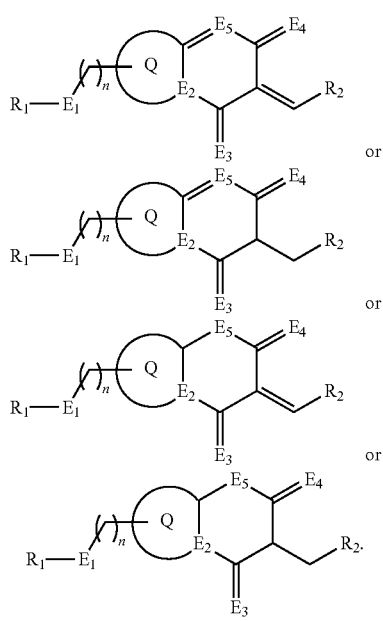

As used herein in connection with Formula (IV.1), when the dashed lines each denote the presence or absence of a bond, then Formula (IV.1) is understood to appear as follows:

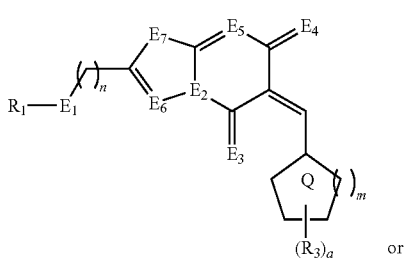

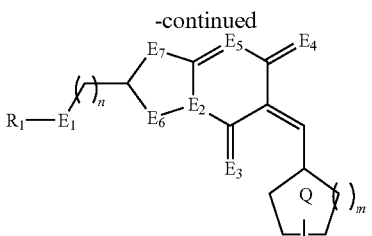

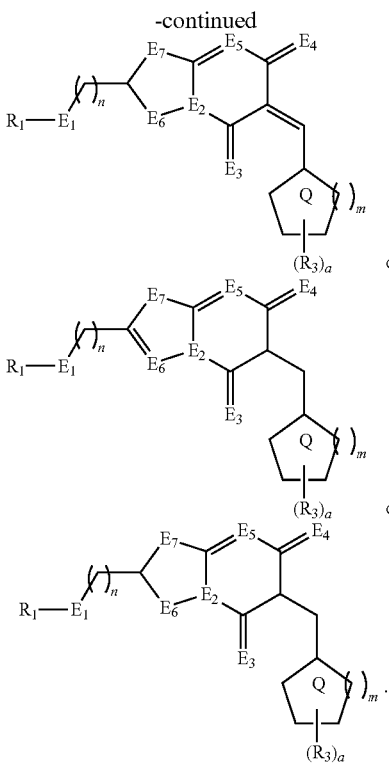

"$(C_2\text{-}C_6)$bridge" as used in connection with the Formulas disclosed herein means a hydrocarbon chain containing 2 to 6 carbon atoms joining two indicated carbon atoms to form a cyclic ring system. Exemplary compounds of the invention include those with a $(C_2)$bridge, —$CH_2$-$CH_2$—, joining the two carbon atoms; a $(C_3)$bridge, —$CH_2$-$CH_2$-$CH_2$—, joining the two carbon atoms; a $(C_4)$bridge, —$CH_2$-$CH_2$—$CH_2$-$CH_2$—, joining the two carbon atoms; a $(C_5)$bridge, —$CH_2$-$CH_2$—$CH_2$-$CH_2$-$CH_2$—, joining the two carbon atoms; or a $(C_6)$bridge, —$CH_2$-$CH_2$—$CH_2$-$CH_2$—$CH_2$-$CH_2$—, joining the two carbon atoms. Examples of a $(C_2\text{-}C_6)$bridge which optionally contains —HC=CH— within the $(C_2\text{-}C_6)$bridge include —HC=CH—, —$CH_2$—HC=CH—, —HC=CH—$CH_2$—, —$CH_2$—HC=CH—$CH_2$—, and the like. Examples of a $(C_2\text{-}C_6)$bridge which optionally contains —O— within the $(C_2\text{-}C_6)$bridge include —$CH_2$—O—$CH_2$— (containing 2 carbon atoms), —$CH_2$—O—$CH_2$—$CH_2$— and —$CH_2$—$CH_2$—O—$CH_2$— (each containing 3 carbon atoms), —$CH_2$—$CH_2$—O—$CH_2$—$CH_2$—, —$CH_2$—O—$CH_2$—$CH_2$—$CH_2$— and —$CH_2$—$CH_2$—$CH_2$—O—$CH_2$— (each containing 4 carbon atoms), and the like.

The phrase "benzo", "benzo group" and the like, when used in connection with the optionally-substituted fused Q group in Formula (IV), means

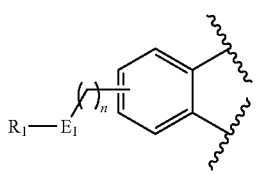

where $R_1$ and $E_1$ and n are defined above for the compounds of Formula (IV).

The phrase "(5- or 6-membered)heteroaryl" when used in connection with the optionally-substituted fused Q group in Formula (IV), means

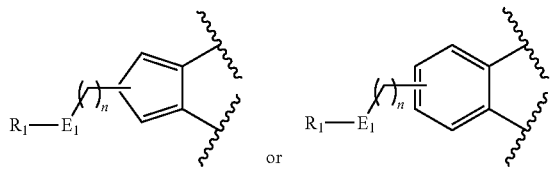

or where at least one carbon atom is replaced with a heteroatom independently selected from nitrogen, oxygen, and sulfur and $R_1$ and $E_1$ and n are defined above for the compounds of Formula (IV). Representative -(5- or 6-membered)heteroaryls include pyridyl, furyl, pyrrolyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, pyrazolyl, isothiazolyl, pyridazinyl, pyrimidyl, pyrazinyl, 1,2,3-thiadiazolyl, 1,3,4-thiadiazolyl, 1,2,5-thiadiazolyl, 1,3,5-triazinyl, and thiophenyl.

The phrase "benzo", "benzo group" and the like, when used in connection with the optionally-substituted fused Q group in Formulas (V) and (V.1), means

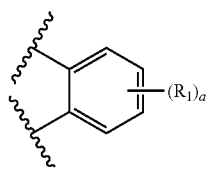

where $R_1$ a are defined above for the compounds of Formulas (V) and (V.1).

The phrase "(5- or 6-membered)heteroaryl" when used in connection with the optionally-substituted fused Q group in Formulas (V) and (V.1), means

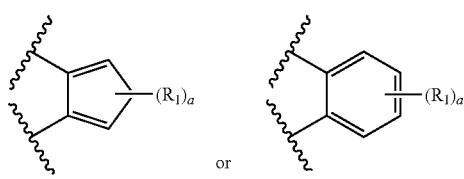

or where at least one carbon atom is replaced with a heteroatom independently selected from nitrogen, oxygen, and sulfur and $R_1$ and a are defined above for the compounds of Formulas (V) and (V.1). Representative -(5- or 6-membered) heteroaryls include pyridyl, furyl, pyrrolyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, pyrazolyl, isothiazolyl, pyridazinyl, pyrimidyl, pyrazinyl, 1,2,3-thiadiazolyl, 1,3,4-thiadiazolyl, 1,2,5-thiadiazolyl, 1,3,5-triazinyl, and thiophenyl.

The phrase "pyrrolino", "pyrrolino group" and the like, when used in connection with the optionally-substituted fused Q group, means optionally substituted

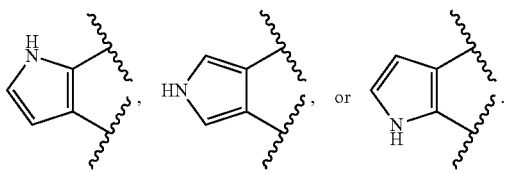 [SMILES: *c1cc[nH]c1* ; *c1c[nH]cc1* ; *c1cc[nH]c1*]

The phrase "imidazolino", "imidazolino group" and the like, when used in connection with the optionally-substituted fused Q group, means optionally substituted

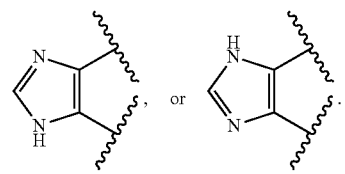 [SMILES: *c1nc[nH]c1* ; *c1nc[nH]c1*]

The phrase "pyrazolino", "pyrazolino group" and the like, when used in connection with the optionally-substituted fused Q group, means optionally substituted

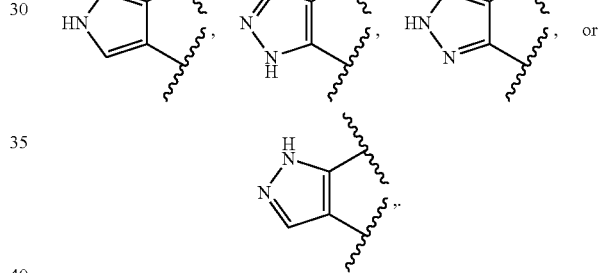

The phrase "triazolino", "triazolino group" and the like, when used in connection with the optionally-substituted fused Q group, means optionally substituted

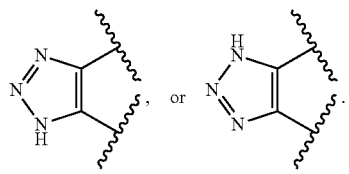 [SMILES: *c1nn[nH]c1* ; *c1nn[nH]c1*]

The phrase "furano", "furano group" and the like, when used in connection with the optionally-substituted fused Q group, means optionally substituted

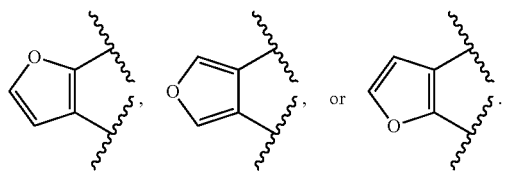 [SMILES: *c1ccoc1* ; *c1cocc1* ; *c1ccoc1*]

The phrase "oxazolino", "oxazolino group" and the like, when used in connection with the optionally-substituted fused Q group, means optionally substituted

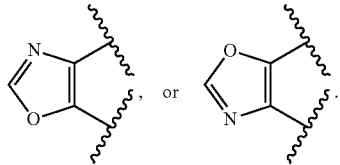 [SMILES: *c1ncoc1* ; *c1ncoc1*]

The phrase "isoxazolino", "isoxazolino group" and the like, when used in connection with the optionally-substituted fused Q group, means optionally substituted

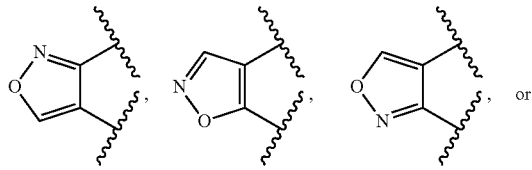

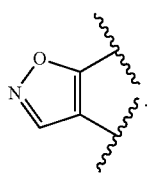

The phrase "oxadiazolino", "oxadiazolino group" and the like, when used in connection with the optionally-substituted fused Q group, means optionally substituted

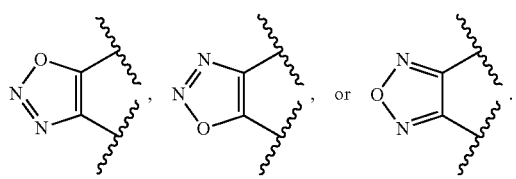 [SMILES: *c1nnoc1* ; *c1nnoc1* ; *c1nonc1*]

The phrase "thiopheno", "thiopheno group" and the like, when used in connection with the optionally-substituted fused Q group, means optionally substituted

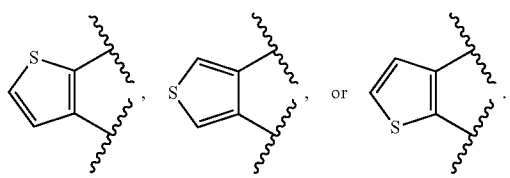 [SMILES: *c1ccsc1* ; *c1cscc1* ; *c1ccsc1*]

The phrase "thiazolino", "thiazolino group" and the like, when used in connection with the optionally-substituted fused Q group, means optionally substituted

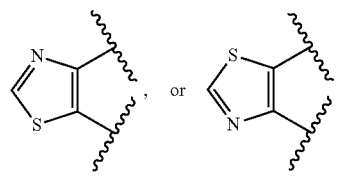

The phrase "isothiazolino", "isothiazolino group" and the like, when used in connection with the optionally-substituted fused Q group, means optionally substituted

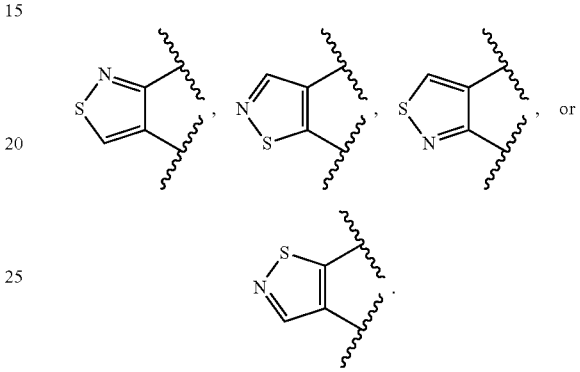

The phrase "thiadiazolino", "thiadiazolino group" and the like, when used in connection with the optionally-substituted fused Q group, means optionally substituted

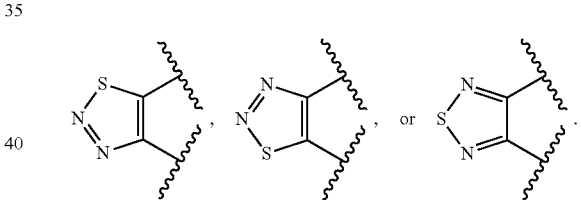

The phrase "pyridine", "pyridino group" and the like, when used in connection with the optionally-substituted fused Q group means optionally substituted

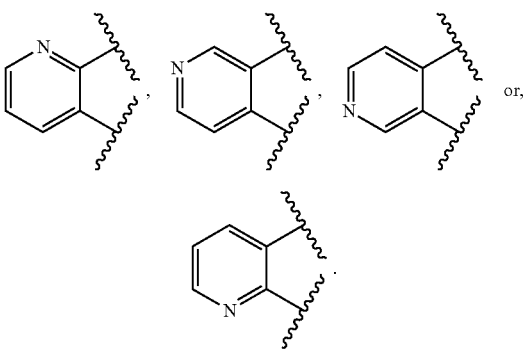

The phrase "pyrimidino", "pyrimidino group" and the like, when used in connection with the optionally-substituted fused Q group means optionally substituted

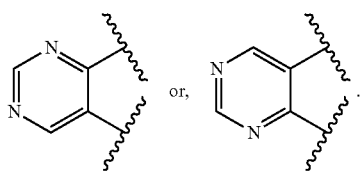 [SMILES: *c1cncnc1* ; *c1cncnc1*] or,

The phrase "pyrazino", "pyrazino group" and the like, when used in connection with the optionally-substituted fused Q group means optionally substituted

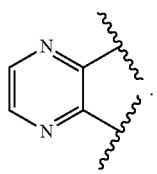 [SMILES: *c1nccnc1*]

The phrase "pyridazino", "pyridazino group" and the like, when used in connection with the optionally-substituted fused Q group means optionally substituted

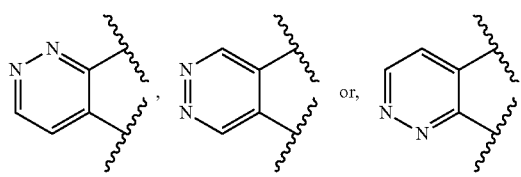 or,

The phrase "diazole", "diazole group" and the like, when used in connection with the formulas disclosed herein means "pyrazolinyl", "pyrazoline group" and the like as well as "imidazolyl", "imidazoline group" and the like.

The phrase "imidazolino", "imidazolino group" and the like, when used in connection with formula (II.2), means optionally substituted

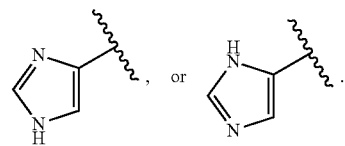 [SMILES: *c1c[nH]cn1 ; *c1cnc[nH]1] or

The phrase "pyrazolino", "pyrazolino group" and the like, when used in connection with formula (II.2), means optionally substituted

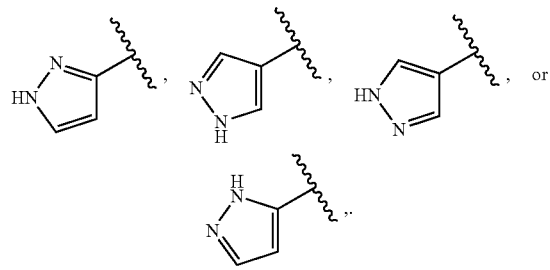 or

The phrase "triazolino", "triazolino group" and the like, when used in connection with formula (II.2), means optionally substituted

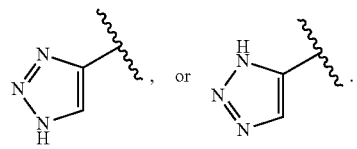 [SMILES: *c1c[nH]nn1 ; *c1cnn[nH]1] or

The phrase "pyridine", "pyridino group" and the like, when used in connection with the formulas disclosed herein means optionally substituted

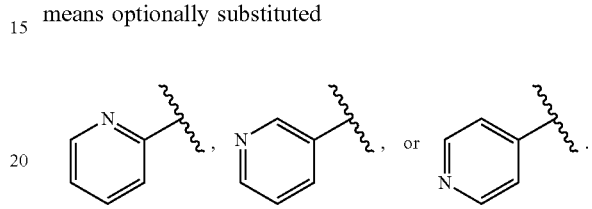 or

The phrase "pyrimidine", "pyrimidino group" and the like, when used in connection with the formulas disclosed herein means optionally substituted

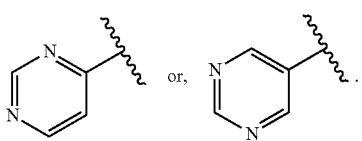 [SMILES: *c1ccncn1 ; *c1cncnc1] or,

The phrase "pyrazine", "pyrazino group" and the like, when used in connection with the formulas disclosed herein means optionally substituted

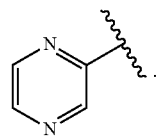 [SMILES: *c1cnccn1]

The phrase "pyridazine", "pyridazino group" and the like, when used in connection with the formulas disclosed herein means optionally substituted

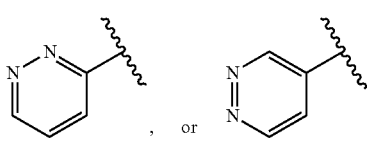 or

The phrase "(C$_6$)cycloalkyl" when used herein means optionally substituted

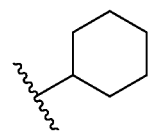

The phrase "(C$_6$)cycloalkenyl" when used herein means optionally substituted

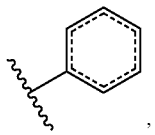, where the cyclic non-aromatic hydrocarbon has at least one carbon-carbon double bond in the cyclic system.

The phrase "(6-membered)heterocycle" when used herein means optionally substituted

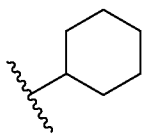 [SMILES: *C1CCCCC1]

where at least one carbon atom in the ring is replaced with a heteroatom independently selected from nitrogen, oxygen, and sulfur.

The phrase "(6-membered)heteroaryl" when used herein means optionally substituted

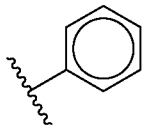

where at least one carbon atom in the ring is replaced with a nitrogen.

The term "animal" includes, but is not limited to, a human or a non-human animal, such as a companion animal or livestock, e.g., a cow, monkey, baboon, chimpanzee, horse, sheep, pig, chicken, turkey, quail, cat, dog, mouse, rat, rabbit or guinea pig.

The phrase "pharmaceutically acceptable derivative", as used herein, includes any pharmaceutically acceptable salt, solvate, prodrug, radio labeled, stereoisomer, enantiomer, diastereomer, other stereoisomeric form, racemic mixture, geometric isomer, and/or tautomer, e.g., of a compound disclosed herein. In one embodiment, the pharmaceutically acceptable derivative is a pharmaceutically acceptable salt, solvate, radio labeled, stereoisomer, enantiomer, diastereomer, other stereoisomeric form, racemic mixture, geometric isomer, and/or tautomer, e.g., of a compound disclosed herein. In another embodiment, the pharmaceutically acceptable derivative is a pharmaceutically acceptable salt, e.g., of a compound disclosed herein.

The phrase "pharmaceutically acceptable salt", as used herein, is any pharmaceutically acceptable salt that can be prepared from a compound disclosed herein including a salt formed from an acid and a basic functional group, such as a nitrogen group, of a compound disclosed herein. Illustrative salts include, but are not limited to, sulfate, citrate, acetate, trifluoroacetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucoronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also includes a salt prepared from a compound disclosed herein having an acidic functional group, such as a carboxylic acid functional group, and a pharmaceutically acceptable inorganic or organic base. Suitable bases include, but are not limited to, hydroxides of alkali metals such as sodium, potassium, cesium, and lithium; hydroxides of alkaline earth metal such as calcium and magnesium; hydroxides of other metals, such as aluminum and zinc; ammonia and organic amines, such as unsubstituted or hydroxy-substituted mono-, di-, or trialkylamines; dicyclohexylamine; tributyl amine; pyridine; picoline; N-methyl,N-ethylamine; diethylamine; triethylamine; mono-, bis-, or tris-(2-hydroxy-(C$_1$-C$_3$)alkyl amines), such as mono-, bis-, or tris-(2-hydroxyethyl)amine, 2-hydroxy-tert-butylamine, or tris-(hydroxymethyl)methylamine, N,N-di-[(C$_1$-C$_3$)alkyl]-N-(hydroxy-(C$_1$-C$_3$)alkyl)-amines, such as N,N-dimethyl-N-(2-hydroxyethyl)amine, or tri-(2-hydroxyethyl)amine; N-methyl-D-glucamine; and amino acids such as arginine, lysine, and the like. One skilled in the art will recognize that, e.g., acid addition salts of a compound disclosed herein can be prepared by reaction of the compounds with the appropriate acid via a variety of known methods.

A compound disclosed herein can contain one or more asymmetric centers and can thus give rise to enantiomers, diastereomers, and other stereoisomeric forms. The invention is also meant to encompass all such possible forms as well as their racemic and resolved forms or any mixture thereof. When a compound disclosed herein contains an olefinic double bond or other center of geometric asymmetry, and unless specified otherwise, it is intended to include all "geometric isomers", e.g., both E and Z geometric isomers. All "tautomers", e.g., ketone-enol, amide-imidic acid, lactam-lactim, enamine-imine, amine-imine, and enamine-enimine tautomers, are intended to be encompassed by the invention as well.

As used herein, the terms "stereoisomer", "stereoisomeric form", and the like are general terms for all isomers of individual molecules that differ only in the orientation of their atoms in space. It includes enantiomers and isomers of compounds with more than one chiral center that are not mirror images of one another ("diastereomers").

The term "chiral center" refers to a carbon atom to which four different groups are attached.

The term "enantiomer" or "enantiomeric" refers to a molecule that is nonsuperimposeable on its mirror image and hence optically active where the enantiomer rotates the plane of polarized light in one direction and its mirror image rotates the plane of polarized light in the opposite direction.

The term "racemic" refers to a mixture of equal parts of enantiomers which is optically inactive.

The term "resolution" refers to the separation or concentration or depletion of one of the two enantiomeric forms of a molecule.

Optical isomers of a compound disclosed herein can be obtained by known techniques such as chiral chromatography or formation of diastereomeric salts from an optically active acid or base.

Accordingly, as used herein in connection with Formula (I.2.1) and R$_1$=(i), R$_1$ of Formula (I.2.1) is understood to appear as follows:

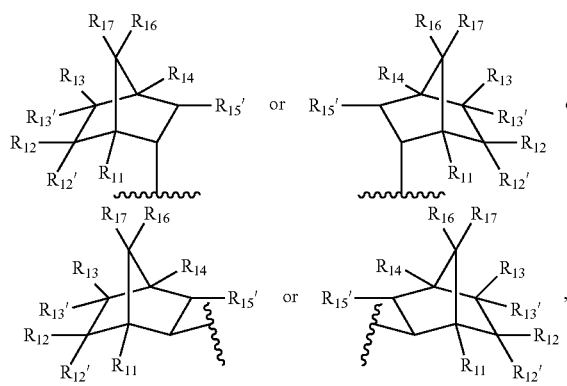

wherein $R_{11}$ to $R_{17}$ are defined as above.

The phrases "treatment of", "treating", and the like include the amelioration or cessation of a condition or a symptom thereof. In one embodiment, treating includes inhibiting, for example, decreasing the overall frequency of episodes of a condition or a symptom thereof. The phrases "prevention of", "preventing", and the like include the avoidance of the onset of a condition or a symptom thereof. A "disorder" includes, but is not limited to, the conditions defined above.

The term "half maximal effective concentration" or "$EC_{50}$" refers to the concentration of a compound disclosed herein which induces a response on a channel halfway between the baseline and maximum after some specified exposure time. The $EC_{50}$ of a graded dose response curve therefore represents the concentration of a compound where 50% of its maximal effect (which may be either agonistic or antagonistic) on the respective channel is observed.

Throughout the literature several different synonyms are used for "TRPA1": ANKTM1, p120, transient receptor potential ankyrin 1, transient receptor potential cation channel subfamily A member 1. All these synonyms are all included in terms of the present invention. Included as well are all functional modifications of the ion channel and the analog receptors from different organisms like human, mouse and rat. The according sequence data is available to the skilled person.

According to the present invention, an antagonist and/or a compound exhibiting "antagonistic activity" refers to a pharmaceutical and/or cosmetic active inhibitor of the TRPA1 related bioactivity (acting in vivo and/or in vitro). The antagonist can bind to the ion channel in a specific or unspecific, reversible or irreversible manner.

According to the present invention, the term "selective antagonistic activity" describes the exclusive inhibition of the TRPA1 ion channel by the respective compound without substantial influence on other ion channels and/or receptor proteins.

According to the present invention, the term "partial antagonistic activity" describes the partial inhibition of the TRPA1 ion channel by the respective compound. The compound reduces the response of the channel to a certain extend without complete inhibition of the TRPA1 related bioactivity.

The term "half maximal inhibitory concentration" or "$IC_{50}$" refers to the concentration of a compound disclosed herein which reduces the response of a channel by half. The $IC_{50}$ of a dose response curve therefore represents the concentration of an antagonist where 50% of its maximal effect on the respective channel is observed.

The term "$EC_{80}$" refers to the concentration of an agonist disclosed herein which gives 80% of its maximal effect on the respective channel.

Preparation of the Compounds

The compounds disclosed herein are either commercially available or can be made using conventional organic synthesis which are known to the person skilled in the art.

Screening Method

As part of the invention, compound libraries can be employed comprising compounds to be tested for having modulating activity for one or more members of the transient receptor potential cation channel families. The methods of the invention can employ such compound libraries e.g. for identifying suitable modulators of TRPA1 and/or any further member of the transient receptor potential cation channel families.

In the context of the present invention, the term "chemical library" means a collection of chemical compounds. A "chemical library" employed in the present invention will comprise at least 2 different compounds, rarely less than about 5 compounds, usually at least about 10 compounds, frequently will have about 50 compounds or more, usually more than about 500 compounds such as about 15,000 compounds or more.

The activity of the compounds comprised by such compound libraries at TRPA1 or TRPM8 (or any further member of the transient receptor potential cation channel families) can be evaluated in a functional cell based assay. In such "functional cell based assays" a compound-channel interaction can lead to a functional response of the cell. The physiological response of the cell, initiated by a screening compound can be quantified by using recombinant reporter technology. It is known in the art that the TRP channels are a family of ion channel proteins that mediate ion influx of $Na^+$ and $Ca^{2+}$ and, in several cases, $Mg^{2+}$. For instance, in the case of TRPA1 and TRPM8, assembly of the channel subunits as tetramers results in the formation of cation-selective channels that permeate calcium ions. This calcium influx can be used as read-out in functional cell based assays.

Furthermore, a cell-based (label-free) impedance assay may be used to validate the antagonistic activity of the tested compounds at TRPA1. In particular, cellular changes (like alterations in cell adherence, shape, volume, and interaction) due to channel activation can be monitored using a label-free, non-invasive assay platform based on cellular dielectric spectroscopy (such as CellKey™ system, Molecular Devices).

The sequences that encode the members of the transient receptor potential cation channel families are available to the person skilled in the art (cf. National Center for Biotechnology Information website: http://www.ncbi.nlm.nih.gov). The methods of amplifying and cloning such sequences (e.g., by PCR) are also commonly known in the art. According to an optional embodiment, TRPM8 (human) has the nucleic acid or amino acid sequence as disclosed in GenBank Accession Number NM_024080 or NP_076985.4 and TRPA1 (human) has the nucleic acid or amino acid sequence as disclosed in GenBank Accession Number NM_007332 or NP_015628.2.

Methods of providing suitable test systems are known to the person skilled in the art. For example, a cell based test system can be based on stably transfected cell lines expressing human TRPM8 or TRPA1. Methods of producing suitable test systems are disclosed, inter alia, in Behrendt H J et al., Br. J. Pharmacol. 2004, 141:737-745, which is enclosed herein by reference. According to an optional embodiment, the functional cell based assay utilizes human HEK293 cells recombinantly expressing human TRPM8 or TRPA1. Agonistic or antagonistic action of a compound can be quantified via a $Ca^{2+}$-sensitive dye (such as FURA, Fluo-4, etc.), wherein agonists produce an increase of intracellular calcium ions and antagonists inhibit an increase of intracellular calcium ions (e.g., triggered by endogenous ligands). Such assays are routine and well known to the person skilled in the art.

According to an optional embodiment of the present invention, a compound library comprising suitable compounds is tested in a screening for antagonistic activity towards TRPA1 and/or other channels. Optionally, compounds can be selected as development candidates, which compounds are antagonists or partial antagonists of TRPA1 in cells expressing the channel. Optionally, the compounds can further be analyzed with regard to their $IC_{50}$ values as well as their efficacy values and/or can be analyzed in a structure-action relationship. Such screening methods are routine and well known to the person skilled in the art.

According to an embodiment, the present invention further encompasses compounds which are identified in such a screening as development candidates.

Embodiments of the Invention

The present invention relates to compounds which are capable of producing a soothing effect when they are brought into contact with the human body. Such compounds have applications in many fields, for example in oral and personal hygiene products and foodstuffs, but also in cosmetics, pharmaceutical composition products, textile products and packaging products.

For instance, a known compound for producing a sensation of cold is menthol (2-isopropyl-5-methyl-cyclohexanol), which has been extensively applied as an additive in, for example, foodstuffs and oral hygiene products. It is used primarily because it elicits a sensation of coolness in the mouth, and because it has a pleasing mint flavour and odour. However, the use of menthol is limited by its strong minty smell which is undesirable for some applications and its relative volatility and burning sensations at high concentrations through unintentional activation of other TRPs/ion channels, such as TRPA1.

It is believed that TRPA1 plays a role in the mechanisms of mechanical and cold hypersensitivity produced by skin irritation or inflammation. Furthermore, TRPA1 responds to a wide variety of stimuli and is activated by a multitude of exogenous and endogenous chemicals, i.e. it can serve as a sensor for reactive and therefore potentially harmful chemicals. As indicated above, certain substances cosmetic and/or pharmaceutical compositions can cause skin irritation if they are applied to the skin, especially the face. This may lead to unpleasant sensations like stinging, burning, and itching, especially in persons with sensitive skin. It is known to persons skilled in the art that these nociceptive sensations are at least to a certain extent mediated by TRPA1. Symptoms like stinging, burning, and itching may lead to dissatisfaction and thereby influence life quality and consumer preferences.

The compounds and compositions disclosed in the present invention exhibit a certain antagonist activity at TRPA1 and have thus the ability to produce a soothing effect when in contact with the skin and/or mucosal membrane of a human or animal body. The term "soothing effect", as used herein, is thus intended to mean any alleviation of unpleasant sensations like stinging, burning, and itching produced by compounds of e.g. cosmetic and/or pharmaceutical compositions.

Such a soothing effect can be desirable in many different applications. For example, the compounds and compositions of the invention have applications in a number of products, such as personal-care products, pharmaceutical compositions, textile products, medical devices, packaging products, and food products.

In an embodiment, the present invention relates to a product comprising a compound that, optionally selectively, exhibits antagonist activity at the TRPA1 channel (e.g. as evaluated in a functional cell based assay under standard conditions as described herein or as evaluated in a cell-based (label-free) impedance assay under standard conditions as described herein), and wherein the product is selected from the group consisting of a personal-care product, a pharmaceutical composition, a textile product, a medical device, a packaging product, and a food product. It is understood that such products can comprise any combination of compounds as described herein above, and optionally can also comprise further agents.

In an embodiment, the present invention relates to a product comprising a compound that selectively exhibits antagonist activity at the TRPA1 channel (e.g. as evaluated in a functional cell based assay under standard conditions as described herein or as evaluated in a cell-based (label-free) impedance assay under standard conditions as described herein), and wherein the product is selected from the group consisting of a personal-care product, a pharmaceutical composition, a textile product, a medical device, a packaging product, and a food product. It is understood that such products can comprise any combination of compounds as described herein above, and optionally can also comprise further agents.

In a further embodiment, the present invention relates to a product comprising a compound that acts as an, optionally selective, TRPA1 antagonist or partial antagonist (e.g. as evaluated in a functional cell based assay under standard conditions as described herein or as evaluated in a cell-based (label-free) impedance assay under standard conditions as described herein), and wherein the product is selected from the group consisting of a personal-care product, a pharmaceutical composition, a textile product, a medical device, a packaging product, and a food product.

In a further embodiment, the present invention relates to a product comprising an effective amount of a compound that acts as an, optionally selective, TRPA1 antagonist or partial antagonist (e.g. as evaluated in a functional cell based assay under standard conditions as described herein or as evaluated in a cell-based (label-free) impedance assay under standard conditions as described herein), and wherein the product is selected from the group consisting of a personal-care product, a pharmaceutical composition, a textile product, a medical device, a packaging product, and a food product.

In a further embodiment, the present invention relates to a product comprising a compound that exhibits antagonist activity at TRPA1, which activity is at least three times, at least five times, or even at least ten times, greater than the activity of the compound at a different ion channel or receptor, optionally at TRPM8 (e.g. as evaluated in a functional cell based assay under standard conditions as described herein), and wherein the product is selected from the group consisting of a personal-care product, a pharmaceutical composition, a medical device, a textile product, a packaging product, and a food product.

In a further embodiment, the present invention relates to a product comprising a compound, wherein in a functional cell based assay the compound inhibits an increase in intracellular calcium concentration in human cells recombinantly expressing human TRPA1 at least three times, at least five times, or even at least ten times more efficient than that of human cells recombinantly expressing a different human ion channel and/or receptor, optionally TRPM8 (e.g. as evaluated in a functional cell based assay under standard conditions as described herein), and wherein the product is selected from the group consisting of a personal-care product, a pharmaceutical composition, a textile product, a medical device, a packaging product, and a food product.

In a further embodiment, the present invention relates to a product selected from the group consisting of a personal-care product, a pharmaceutical composition, a textile product, a medical device, a packaging product, and a food product, which product comprises a compound selected from the group consisting of Compounds I, II, III, IV, V, I.1, I.1.1, II.1, III.1, IV.1, V.1, I.2, I.2.1, I.2A, I.2B, I.2C, I.2D, I.2E, I.2F, I.2G, I.2H, I.2I, I.2J, I.2K, I.2L, I.2M, I.2N, I.2O, I.2P, II.2, III.2, IV.2, V.2, I.3, II.3, III.3, IV.3, and V.3, wherein the Compounds have the chemical structures as defined herein above.

In a further embodiment, the present invention relates to a product selected from the group consisting of a personal-care product, a pharmaceutical composition, a textile product, a medical device, a packaging product, and a food product, which product comprises a compound selected from the group consisting of Compounds I.1, I.1.1, II.1, III.1, IV.1, V.1, I.2, I.2.1, I.2A, I.2B, I.2C, I.2D, I.2E, I.2F, I.2G, I.2H, I.2I, I.2J, I.2K, I.2L, I.2M, I.2N, I.2O, I.2P, II.2, III.2, IV.2, V.2, I.3, II.3, III.3, IV.3, and V.3, wherein the Compounds have the chemical structures as defined herein above.

In a further embodiment, the present invention relates to a product selected from the group consisting of a personal-care product, a pharmaceutical composition, a textile product, a medical device, a packaging product, and a food product, which product comprises a compound selected from the group consisting of Compounds I.2, I.2.1, I.2A, I.2B, I.2C, I.2D, I.2E, I.2F, I.2G, I.2H, I.2I, I.2J, I.2K, I.2L, I.2M, I.2N, I.2O, I.2P, II.2, III.2, IV.2, V.2, I.3, II.3, III.3, IV.3, and V.3, wherein the Compounds have the chemical structures as defined herein above.

In a further embodiment, the present invention relates to a product selected from the group consisting of a personal-care product, a pharmaceutical composition, a textile product, a medical device, a packaging product, and a food product, which product comprises a compound selected from the group consisting of Compounds I.3, II.3, III.3, IV.3, and V.3, wherein the Compounds have the chemical structures as defined herein above.

In a further embodiment, the present invention relates to a compound selected from the group consisting of Compounds I, II, III, IV, V, I.1, I.1.1, II.1, III.1, IV.1, V.1, I.2, I.2.1, I.2A, I.2B, I.2C, I.2D, I.2E, I.2F, I.2G, I.2H, I.2I, I.2J, I.2K, I.2L, I.2M, I.2N, II.2O, I.2P, II.2, III.2, IV.2, V.2, I.3, II.3, III.3, IV.3, and V.3, wherein the Compounds have the chemical structures as defined herein above. In a further embodiment, the present invention relates to a compound selected from the group consisting of Compounds I.1, I.1.1, II.1, III.1, IV.1, V.1, I.2, I.2.1, I.2A, I.2B, I.2C, I.2D, I.2E, I.2F, I.2G, I.2H, I.2I, I.2J, I.2K, I.2L, I.2M, I.2N, I.2O, I.2P, II.2, III.2, IV.2, V.2, I.3, II.3, III.3, IV.3, and V.3, wherein the Compounds have the chemical structures as defined herein above. In a further embodiment, the present invention relates to a compound selected from the group consisting of Compounds I.2, I.2.1, I.2A, I.2B, I.2C, I.2D, I.2E, I.2F, I.2G, I.2H, I.2I, I.2J, I.2K, I.2L, I.2M, I.2N, I.2O, I.2P, II.2, III.2, IV.2, V.2, I.3, II.3, III.3, IV.3, and V.3, wherein the Compounds have the chemical structures as defined herein above. In a further embodiment, the present invention relates to a compound selected from the group consisting of Compounds I.2.1, I.2A, I.2B, I.2C, I.2D, I.2E, I.2F, I.2G, I.2H, I.2I, I.2J, I.2K, I.2L, I.2M, I.2N, I.2O, I.2P, II.2, III.2, IV.2, V.2, I.3, II.3, III.3, IV.3, and V.3, wherein the Compounds have the chemical structures as defined herein above. In a further embodiment, the present invention relates to a compound selected from the group consisting of Compounds I.3, II.3, III.3, IV.3, and V.3, wherein the Compounds have the chemical structures as defined herein above.

Optionally, the compound exhibits an antagonist activity at TRPA1, which activity is at least three times, optionally at least four times, five times, seven times, ten times, 12 times, 15 times or 20 times, greater than the antagonist activity of the compound at TRPM8 (e.g. as evaluated in a functional cell based assay under standard conditions as described herein).

According to an optional embodiment, the compound acts as a TRPA1 partial antagonist or antagonist (e.g. as evaluated in a functional cell based assay under standard conditions as described herein or as evaluated in a cell-based (label-free) impedance assay under standard conditions as described herein).

According to an optional embodiment, the compound acts as a selective TRPA1 partial antagonist or antagonist (e.g. as evaluated in a functional cell based assay under standard conditions as described herein or as evaluated in a cell-based (label-free) impedance assay under standard conditions as described herein).

According to a further optional embodiment, in a functional cell based assay the compound inhibits an increase in intracellular calcium concentration in human cells recombinantly expressing human TRPA1 at least four times, five times, seven times, ten times, 12 times, 15 times or 20 times more efficient than that of human cells recombinantly expressing human TRPM8 (e.g. as evaluated in a functional cell based assay under standard conditions as described herein).

According to an optional embodiment of the present invention, the $IC_{50}$ value of the compound with regard to TRPA1 (antagonistic activity against menthol) is less than 20 µM, 15 µM, 12 µM, 10 µM, 8 µM, 6 µM, 4 µM, 2 µM, 1 µM or 0.5 µM (as evaluated in a functional cell based assay under standard conditions as described herein). According to an optional embodiment of the present invention, the $IC_{50}$ value of the compound with regard to TRPA1 (antagonistic activity against propylparaben) is less than 20 µM, 15 µM, 12 µM, 10 µM, 8 µM, 6 µM, 4 µM, 2 µM, 1 µM or 0.5 µM (as evaluated in a functional cell based assay under standard conditions as described herein). According to an optional embodiment of the present invention, the $IC_{50}$ value of the compound with regard to TRPA1 (antagonistic activity against retinol) is less than 20 µM, 15 µM, 12 µM, 10 µM, 8 µM, 6 µM, 4 µM, 2 µM, 1 µM or 0.5 µM (as evaluated in a functional cell based assay under standard conditions as described herein). According to an optional embodiment of the present invention, the $IC_{50}$ value of the compound with regard to TRPA1 (antagonistic activity against allyl isothiocyanate) is less than 20 µM, 15 µM, 12 µM, 10 µM, 8 µM, 6 µM, 4 µM, 2 µM, 1 µM or 0.5 µM (as evaluated in a functional cell based assay under standard conditions as described herein).

Optionally, the compound is selected from the group consisting of Compounds I, II, III, IV, V, I.1, I.1.1, II.1, III.1, IV.1, V.1, I.2, I.2.1, I.2A, I.2B, I.2C, I.2D, I.2E, I.2F, I.2G, I.2H, I.2I, I.2J, I.2K, I.2L, I.2M, I.2N, I.2O, I.2P, II.2, III.2, IV.2, V.2, I.3, II.3, III.3, IV.3, and V.3, wherein the Compounds have the chemical structures as defined herein above. Optionally, the compound is selected from the group consisting of Compounds I.1, I.1.1, II.1, III.1, IV.1, V.1, I.2, I.2.1, I.2A, I.2B, I.2C, I.2D, I.2E, I.2F, I.2G, I.2H, I.2I, I.2J, I.2K, I.2L, I.2M, I.2N, I.2O, I.2P, II.2, III.2, IV.2, V.2, I.3, II.3, III.3, IV.3, and V.3, wherein the Compounds have the chemical structures as defined herein above. Optionally, the compound is selected from the group consisting of Compounds I.2, I.2.1, I.2A, I.2B, I.2C, I.2D, I.2E, I.2F, I.2G, I.2H, I.2I, I.2J, I.2K, I.2L, I.2M, I.2N, I.2O, I.2P, II.2, III.2, IV.2, V.2, I.3, II.3, III.3, IV.3, and V.3, wherein the Compounds have the chemical structures as defined herein above. Optionally, the compound is selected from the group consisting of Compounds I.3, II.3, III.3, IV.3, and V.3, wherein the Compounds have the chemical structures as defined herein above.

In one further embodiment, the present invention relates to the use of a compound as defined herein above in a product selected from the group consisting of a personal-care product, a pharmaceutical composition, a textile product, a packaging product, a medical device, and a food product. In one further embodiment, the present invention relates to a compound as defined herein above for use in therapy. In one further embodiment, the present invention relates to a compound as defined herein above for use in the treatment of pain. In one further embodiment, the present invention relates to the use of a compound as defined herein for the modulation of the taste of a food product. In one further embodiment, the present invention relates to an in vitro, in vivo or ex vivo use of a compound as defined herein above as soothing agent. In one further embodiment, the present invention relates to a cosmetic use of a compound as defined herein above as soothing agent, i.e. its use as soothing agent in a cosmetic product, a wound dressing or a hygiene product. In one further embodiment, the present invention relates to an in vitro method of inhibiting TRPA1, wherein TRPA1 is contacted with a compound as defined herein above.

In the context of the present invention, the phrase "effective amount", when used in connection with a compound of the invention, means an amount effective for: (a) treating or preventing a condition; or (b) detectably blocks binding of another agent (such as an endogenous ligand) to TRPA1 in a cell or detectably blocks the functional modulation of TRPA1 by another agent (such as an endogenous ligand) in a cell (e.g. as evaluated in a functional cell based assay under standard conditions as described herein or as evaluated in a cell-based (label-free) impedance assay under standard conditions as described herein).

The terms "modulate", "modulating", and the like as used herein with respect to TRPM8 or TRPA1 mean the mediation of a pharmacodynamic response in a cell from (i) inhibiting or activating the respective channel, or (ii) directly or indirectly affecting the normal regulation of the channel activity (e.g., as evaluated in a functional cell based assay under standard conditions as described herein). Compounds that modulate the channel activity include agonists, partial agonists, antagonists, mixed agonists/antagonists, mixed partial agonists/antagonists and compounds which directly or indirectly affect regulation of the channel activity (as evaluated in a functional cell based assay under standard conditions as described herein).

The terms "selective modulation", "selectively modulate", and the like as used herein with respect to TRPM8 or TRPA1 mean the mediation of a pharmacodynamic response in a cell from (i) inhibiting or activating the respective channel (in particular, TRPA1) without substantially triggering another channel (in particular, TRPM8), or (ii) directly or indirectly affecting the normal regulation of the activity of the respective channel (in particular, TRPA1) without substantially affecting the normal regulation of the activity of another channel (in particular, TRPM8) (e.g., as evaluated in a functional cell based assay under standard conditions as described herein).

As used herein, a compound disclosed herein that binds to a channel and mimics the regulatory effect(s) of an endogenous ligand is defined as an "agonist" (e.g., as evaluated in a functional cell based assay under standard conditions as described herein). As used herein, a compound that binds to a channel and is only partly effective as an agonist is defined as a "partial agonist" (e.g., as evaluated in a functional cell based assay under standard conditions as described herein). As used herein, a compound that binds to a channel but produces no regulatory effect, but rather blocks binding of another agent to the channel or blocks the functional modulation of the channel by another agent is defined as an "antagonist" or "silent agonist" (i.e. a compound with no efficacy but binding capacity). For an overview of drug binding mechanisms see: Ross and Kenakin, *Pharmacodynamics: Mechanisms of Drug Action and the Relationship Between Drug Concentration and Effect*, Chapter 2 in *Goodman & Gilman's The Pharmacological Basis of Therapeutics* 31-32 (J. G. Hardman, L. E. Limbird and A. Goodman-Gilman eds., $10^{th}$ ed 2001).

In the context of the present invention, the phrase "antagonist", when used in connection with a compound of the invention, means a compound according to the invention that binds to a channel (in particular, TRPA1) and produces no regulatory effect, but rather blocks binding of another agent to the channel or blocks the functional modulation of the channel by another agent such as an endogenous ligand, e.g., as evaluated in a functional cell based assay under standard conditions as described herein.

In the context of the present invention, the phrase "selective antagonist", and the like, when used in connection with a compound of the invention, means a compound according to the invention that binds to a channel (in particular, TRPA1) and produces no regulatory effect, but rather blocks binding of another agent to the channel or blocks the functional modulation of the channel by another agent such as an endogenous ligand, however without substantially affecting the normal regulation of the activity of another channel (in particular, TRPM8) (e.g., as evaluated in a functional cell based assay under standard conditions as described herein). However, it can be desirable to provide a compound that binds to a channel (in particular, TRPA1) and produces no regulatory effect, but rather blocks binding of another agent to the channel or blocks the functional modulation of the channel by another agent such as an endogenous ligand, but which compound antagonizes another channel (in particular, TRPM8), e.g., as evaluated in a functional cell based assay under standard conditions as described herein.

The term "exhibit antagonist activity on TRPA1" and the like as used herein with respect to TRPA1 mean the inhibitory activity (if the compound acts as antagonist) at TRPA1, as can be evaluated in a functional cell based assay under standard conditions as described herein. In particular, the term "exhibit antagonist activity" and the like as used herein with respect to e.g. TRPA1 mean the mediation of a pharmacodynamic response in a cell from (i) inhibiting the respective channel (in particular, TRPA1), or (ii) blocking binding of another agent to the channel (in particular, TRPA1) or blocking the functional modulation of the channel (in particular, TRPA1) by another agent such as an endogenous ligand.

As used herein, a functional cell based assay under standard conditions means evaluating the cellular activity of compounds with regard to the modulation of the intracellular calcium level using cells recombinantly expressing human TRPM8 or human TRPA1. In particular, in this context the term "standard conditions" means an activity test using HEK293 cells recombinantly expressing either human TRPM8 or human TRPA1, which cells have been contacted with a calcium-sensitive dye (such as Fluo-4AM, i.e. Fluo-4-acetoxymethylester), wherein the cells are incubated with the compound to be tested, and receptor modulation is quantitatively detected by calcium-dependent changes is fluorescence intensity. Such a test system is disclosed, inter alia, in Behrendt H J et al., Br. J. Pharmacol. 2004, 141: 737-745, which is enclosed herein by reference.

As used herein, a cell-based (label-free) impedance assay under standard conditions means evaluating the antagonistic activity of compounds by measuring changes in the complex impedance of the confluent cell monolayer. In particular, in this context the term "standard conditions" means an activity test using HaCaT cells (immortalized human epithelial keratinocytes) (Boukamp, 1988), wherein the measurement is performed when the cells established a confluent monolayer (roughly 24 h after seeding) and cellular changes (like alterations in cell adherence, shape, volume, and interaction) due to channel activation are monitored using a label-free, non-invasive assay platform based on cellular dielectric spectroscopy (such as, e.g., CellKey™ system, Molecular Devices). Performing such a cell-based (label-free) impedance assay is routine to a person skilled in the art.

According to an optional embodiment, the personal-care product is selected from the group consisting of a cosmetic product, a wound dressing or a hygiene product. According to an optional embodiment, the cosmetic product is selected from the group consisting of an insect repellent composition, an oral hygiene composition, a skin care composition, and a hair care composition. Personal hygiene applications such as skin care compositions and hair care compositions include lotions, shaving cream, post shaving preparations, shampoos, conditioners, facial cleansers, soaps, bath oils and foams, antiperspirants, deodorants. Oral hygiene applications include toothpastes, mouthwashes, dental floss, chewing gum and breath fresheners.

In one embodiment the food product is selected from beverages and edibles. According to an optional embodiment the beverages are selected from wine, coffee, fruit juices or tea. According to another optional embodiment the beverages are selected from wine, coffee or fruit juices. According to an optional embodiment the edibles are selected from bakery and dairy products, products based on fruit or vegetables, convenience meals, sweets or snack food. According to another optional embodiment, the food product is selected from the group consisting of ice cream, mousse, crème, beverages and confectionery.

In a further embodiment of the invention the food product comprises one or more ingredient(s) which impart(s) a strong and potentially unpleasant, e.g. astringent and/or pungent taste to the food product. Such a strong and potentially unpleasant taste may be caused by compounds present in fruits, vegetables, wines, spices or nuts. Optionally, these ingredients may include, without limitation, vitamins, minerals, cinnamaldehyde, carvacrol, menthol and/or organosulfur compounds such as allylisothiocyanat, allicin and diallyl sulphides.

In a further embodiment, the present invention relates to a food product, which product comprises one or more ingredient(s) imparting a strong and potentially unpleasant taste as described above and a compound selected from the group consisting of Compounds I.3, II.3, III.3, IV.3, and V.3, wherein said compounds have the chemical structures as defined herein above.

According to an optional embodiment, the textile product is selected from the group consisting of shirts, trousers, socks, towels, headgear, underwear and shoes.

According to an optional embodiment, the pharmaceutical composition is selected from the group consisting of medicaments for the treatment of pain. The present invention further relates to a compound as defined herein above for use in the treatment of (e.g. inflammatory) pain.

A soothing effect can also be desirable in packaging products, wherein such soothing effect is particularly desired upon contact with the content of such packaging products (which can comprise different materials such as paper or plastics). Compounds according to the present invention may be associated with the packaging product material in various ways, e.g., by spin coating, printing, micro capsules, direct incorporation into the material (e.g. extrusion), covalent binding to molecules of the packaging material etc. Suitable methods are known to the person skilled in the art.

A soothing effect can also be desirable in textile products, wherein such soothing effect is particularly desired by wearing such products. Compounds according to the present invention may be associated with the textile product material in various ways, e.g., by spin coating, printing, micro capsules, direct incorporation into the material (e.g. extrusion), covalent binding to molecules of the packaging material etc. Suitable methods are known to the person skilled in the art.

A further embodiment of the present invention relates to the use of the compounds as defined herein, and in particular as defined in Table 1 herein above, and methods of using said compounds. A further embodiment of the present invention also relates to the use of variants of the compounds and methods of using said compounds. In a preferred embodiment of the present invention, said compounds or the corresponding (e.g. cosmetic) compositions are to be applied to the skin of a human subject. In a further preferred embodiment, said application has a skin irritation-reducing (soothing) effect on the part of the body to which the compound or cosmetic composition is applied to.

The specific nature of the products and compositions of the present invention (e.g. the nature of the additional components, the relative proportions of the components and the physical nature of the composition) will depend on the particular application and are known to the skilled person. While the above invention has been described with respect to some of its preferred embodiments, this is in no way to limit the scope of the invention. The person skilled in the art is clearly aware of further embodiments and alterations to the previously described embodiments that are still within the scope of the present invention.

EXAMPLES

Experimental Procedures and Methods

Calcium influx into cells (under defined buffer conditions) was measured by a calcium-sensitive fluorescence assay (cf.

example 3) to quantify activation of the non-selective TRPA1 cation channel. The assay system was used to screen a library of commercially available substances (of synthetic or natural origin) with respect to their antagonistic activity. Afterwards, the activity of hit compounds was tested against different TRPA1 agonists that are relevant in the technical field referred to. A cell-based impedance assay system was used to confirm the antagonistic activity of the screened compounds in a more physiological context (cf. example 4).

Example 1

Cloning of Human TRPA1

The human TRPA1 ion channel was cloned from cDNA derived from a human fetal lung fibroblast cell line (type: IMR-90). First-strand cDNA was generated from total RNA by standard techniques. The TRPA1 coding sequence (according to the NCBI database entry NM_007332) was cloned using standard PCR methods. The isolated gene was confirmed (with a known SNP (single nucleotide polymorphism) in exon 1 leading to an arginine at position 3) by DNA sequencing and subcloned to generate a suitable expression vector equipped with a tetracycline-regulated promoter for controlled expression of the ion channel. The generation of such expression systems are routine to the person skilled in the art. Alternatively, the expression system could have been generated by chemical DNA synthesis of the TRPA1 gene.

Example 2

Establishment of a Cell-Based Screening System

To identify substances with antagonistic activity a high-throughput cell-based in vitro assay system was established. For this purpose, a stable TRPA1 expressing human embryonic kidney cell line (type: HEK293) was generated using a suitable expression vector (cf. example 1). For the present invention, stable cell lines were generated by transfection of vector DNA using Lipofectamine™ 2000 reagent, purchased from Invitrogen, according to the instructions in the suppliers' manual. Techniques for the generation of stable cell lines are known to persons skilled in the art.

Example 3

Cell-Based Calcium Assay for the Identification of TRPA1 Modulators

The HEK293 cell line expressing recombinant human TRPA1 under the control of a tetracycline-regulated promoter was used in this assay (cf. example 2). Functional modulation of TRPA1 by the tested compounds was measured and quantified using the calcium sensitive fluorescent probe Fluo-4 AM on a fluorescence microplate reader. Activation of TRPA1 by an agonist led to an increase in the intracellular calcium concentration and thus an increase in fluorescence intensity. Inhibition of the TRPA1 related bioactivity by an antagonist reduced an agonist-evoked increase in fluorescence intensity significantly or preferably blocked the agonist-evoked signal completely.

Procedure: Cells were cultured in DMEM (high glucose) supplemented with tetracycline-free FCS (10% v/v), L-glutamine (4 mM), blasticidin (15 µg/ml) and hygromycin (100 µg/mL) in a water-saturated atmosphere at 37° C. and 5% $CO_2$. Cells were seeded onto 96-well clear-bottom black-walled assay plates at a density of 70,000 cells per well in 100 µl of cell culture medium. Expression of the ion channel was induced or not induced by addition of tetracycline (1 µg/ml final concentration) to the cell culture medium (while seeding the cells). Calcium influx into the living cells due to channel activation was monitored 24 h later using the calcium sensitive fluorescent probe Fluo-4 AM on a fluorescence microplate reader (FlexStation® system, Molecular Devices). Therefore 100 µl Krebs-HEPES (1(H) buffer (118 mM NaCl; 4.7 mM KCl; 1.3 mM $CaCl_2$; 1.2 mM $MgSO_4$; 1.2 mM $KH_2PO_4$; 4.2 mM $NaHCO_3$; 10 mM Hepes, pH 7.4) supplemented with sulfinpyrazone (250 µM) and Fluo-4 AM (4 µM) were added and the cells were incubated for an additional hour in a water-saturated atmosphere at 37° C. and 5% $CO_2$.

Measurement of agonistic activity: Medium was replaced with 200 µl KH buffer supplemented with sulfinpyrazone (250 µM). Subsequently, 50 µl KH buffer supplemented with the agonists or control substances were added. Changes in fluorescence were recorded at 20-26° C.

Measurement of antagonistic activity (screening): Medium was replaced with 150 µl KH buffer supplemented with sulfinpyrazone (250 µM). Subsequently, 50 µl KH buffer supplemented with the screening compounds (50 µM; leading to a final concentration of 10 µM under measurement conditions) or control substances were added and the cells were incubated for 10 min. under assay conditions in the microplate reader. Changes in fluorescence were recorded at 20-26° C. after addition of 50 µl KH buffer supplemented with the TRPA1 agonist menthol (175 µM; leading to a final concentration of 35 µM under measurement conditions). The published TRPA1 antagonist AP-18 (Petrus, 2007) was used as a control for TRPA1-specific agonistic activity. Subsequently, the inventive compounds were tested for their capacity to reduce signals triggered by addition of propylparaben ($EC_{80}$=80 µM), retinol ($EC_{80}$=150 µM), and allyl isothiocyanate ($EC_{80}$=5 µM) (cf. Table 2).

Analysis: Calcium mobilization was quantified as the change of peak fluorescence (ΔF) over the baseline level (F). The data was analyzed with the software of the microplate reader. Potential TRPA1 antagonists were tested in an effective range of 0.1-50 µM for their capacity to reduce the menthol-evoked signal.

Example 4

Cell-Based (Label-Free) Impedance Assay

HaCaT cells (immortalized human epithelial keratinocytes) were used in this assay (Boukamp, 1988). Antagonistic activity of the tested compounds was quantified by measuring changes in the complex impedance of the confluent cell monolayer.

Procedure: Cells were cultured in DMEM (low glucose) supplemented with FCS (10% v/v) and L-glutamine (4 mM) in a water-saturated atmosphere at 37° C. and 5% $CO_2$. Cells were seeded onto CellKey™ standard 96W microplates at a density of 80000 cells per well in 100 µl of cell culture medium. The measurement was performed when the cells established a confluent monolayer (roughly 24 h after seeding). Cellular changes (like alterations in cell adherence, shape, volume, and interaction) due to channel activation were monitored using a label-free, non-invasive assay platform based on cellular dielectric spectroscopy (CellKey™ system, Molecular Devices).

Medium was replaced with 135 µl CellKey™ assay buffer (HBSS buffer; 20 mM Hepes; 0.1% BSA) in the microplate reader by the embedded "fluid exchange" protocol. Measurement was performed after an equilibration period of approximately 1 h under assay conditions according to the embedded "antagonist adherent cell" protocol: The compounds were applied in 15 µl CellKey™ assay buffer 15 min. prior to the agonist. Cellular responses were recorded at 30° C. after addition of 15 µl CellKey™ assay buffer supplemented with propylparaben (200 µM final concentration) or retinol (300 µM final concentration).

Analysis: Cellular changes were quantified as changes in complex impedance (dZ) of the cell layer. The data was analyzed with the software of the microplate reader. Potential TRPA1 antagonists were tested in an effective range of 1-50 µM.

Example 5

Exemplary Values for the Antagonistic Efficacy of the Compounds Disclosed Herein

TABLE 2

Antagonistic efficacy ($IC_{50}$ values) of compounds measured with the calcium assay

| Compounds | Antagonistic activity ($IC_{50}$ [µM] values) | | | |
|---|---|---|---|---|
| | Menthol | Propylparaben | Retinol | Allyl isothiocyanate |
| I.3 | 3.5 | 4.7 | 3.4 | 2.5 |
| II.3 | 1.5 | 0.9 | 0.6 | 1.6 |
| III.3 | 0.1 | 0.4 | 0.4 | 1.2 |
| IV.3 | 0.3 | 4.3 | 3.3 | 3.5 |
| V.3 | 4.5 | 26 | 14 | 26*⁾ |

*⁾only partial antagonistic activity

Surprisingly, analysis of the data revealed that TRPA1 antagonists according to the present invention could be described which antagonize activation of the TRPA1 ion channel by various agonists acting through different mechanisms.

Exemplary dose-response curves are shown in FIGS. 1 and 2 (calcium assay) and FIGS. 3 and 4 (impedance assay), but should not be construed as being limiting.

Example 6

Test for Cross-Selectivity of the Compounds on TRPM8

The test for cross-selectivity of the compounds on TRPM8 was performed in much the same way as the initial screening on TRPA1 (described in example 3). A HEK293 cell line expressing recombinant human TRPM8 under the control of a tetracycline-regulated promoter was used. Cells were cultured under the conditions mentioned in example 3. Functional modulation of TRPM8 was measured and quantified using the calcium sensitive fluorescent probe Fluo-4 AM on a fluorescence microplate reader. The assay was performed as described in example 3. Changes in fluorescence were recorded at 26-30° C. after addition of the compounds and/or the TRPM8 agonist menthol ($EC_{80}$=12 µM). Dose-response curves are shown in FIGS. 5 to 9 (calcium assay) against menthol, which is known to trigger both TRPA1 as well as TRPM8. In particular, the antagonistic activity of compound I.3, II.3, III.3, IV.3 and V.3 at TRPA1 (open circles, continuous line) as well as the antagonistic activity of said compounds at TRPM8 (filled squares, dotted line) was measured and compared. Activation of the two ion channels was triggered by addition of menthol ($EC_{80}$[TRPA1]=35 µM and $EC_{80}$[TRPM8]=12 µM). The receptor signals were normalized to the pure menthol signal in each case.

Example 7

Test for In Vivo Activity of the Compounds

Antagonistic in vivo activity at TRPA1 was tested in a blinded study on the lid-cheek junction of 16 test persons. The ion channel was stimulated using a known TRPA1 agonist: flufenamic acid, a member of the group of NSAIDs (non-steroidal anti-inflammatory drugs) (Hu et al., 2010). The concentration of flufenamic acid was adjusted to a level that induced a pronounced stinging/burning sensation in the majority of the testers (0.75%).

Procedure: One side of the face (the lid-cheek junction) was pre-incubated with the antagonist (compound I.3, 0.05%)—the other side with placebo. Afterwards, flufenamic acid was applied to both sides simultaneously. Testers were asked several questions regarding their individual perception of irritation.

Analysis: Testers were asked if they could feel the NSAID-triggered stinging/burning. The strength of the stimulus was not judged. Then they were asked if they could perceive a difference between the two areas. If the answer was yes, they were asked which side was perceived as more pleasant. The antagonistic effect was graded in three categories: no reduction, reduction and strong reduction of the irritation. 10 out of 14 testers perceived a soothing effect by the use of the antagonist (two individuals felt no stimulus at all).

The results of this test are shown in FIG. 10.

REFERENCES

Atoyan R, Shander D, and Botchkareva N V (2009) Non-neuronal expression of transient receptor potential type A1 (TRPA1) in human skin. *J Invest Dermatol* 129:2312-2315.

Bandell M, Story G M, Hwang S W, Viswanath V, Eid S R, Petrus M J, Earley T J, and Patapoutian A (2004) Noxious cold ion channel TRPA1 is activated by pungent compounds and bradykinin. *Neuron* 41:849-857.

Bautista D M, Jordt S E, Nikai T, Tsuruda P R, Read A J, Poblete J, Yamoah E N, Basbaum A I, and Julius D (2006) TRPA1 mediates the inflammatory actions of environmental irritants and proalgesic agents. *Cell* 124:1269-1282.

Bautista D M, Movahed P, Hinman A, Axelsson H E, Sterner O, Högestätt E D, Julius D, Jordt S E, and Zygmunt P M (2005) Pungent products from garlic activate the sensory ion channel TRPA1. *Proc Natl Acad Sci USA* 102:12248-12252.

Boukamp P, Petrussevska R T, Breitkreutz D, Hornung J, Markham A, and Fusenig N E (1988) Normal keratinization in a spontaneously immortalized aneuploid human keratinocyte cell line. *J Cell Biol* 106:761-71.

Clapham D E (2003) TRP channels as cellular sensors. *Nature* 426:517-524.

Clapham D E (2007) SnapShot: mammalian TRP channels. *Cell* 129:220.

Corey D P, García-Añoveros J, Holt J R, Kwan K Y, Lin S Y, Vollrath M A, Amalfitano A, Cheung E L, Derfler B H, Duggan A, et al. (2004) TRPA1 is a candidate for the mechanosensitive transduction channel of vertebrate hair cells. *Nature* 432:723-730.

da Costa D S, Meotti F C, Andrade E L, Leal P C, Motta E M, Calixto J B (2010) The involvement of the transient receptor potential A1 (TRPA1) in the maintenance of mechanical and cold hyperalgesia in persistent inflammation. *Pain* 148:431-7.

Farage M A, Maibach H I (2010) Sensitive skin: closing in on a physiological cause. *Contact Dermatitis* 62:137-49.

Fujita F, Moriyama T, Higashi T, Shima A, Tominaga M (2007) Methyl p-hydroxybenzoate causes pain sensation through activation of TRPA1 channels. *Br J Pharmacol* 151:153-60.

Gaudet R (2008) TRP channels entering the structural era. *J Physiol* 586:3565-75.

Hinman A, Chuang H H, Bautista D M, and Julius D (2006) TRP channel activation by reversible covalent modification. *Proc Natl Acad Sci USA* 103:19564-19568.

Howard J and Bechstedt S (2004) Hypothesis: a helix of ankyrin repeats of the NOMPC-TRP ion channel is the gating spring of mechanoreceptors. *Curr Biol* 14:R224-R226.

Hu H, Tian J, Zhu Y, Wang C, Xiao R, Herz J M, Wood J D and Zhu M X (2010) Activation of TRPA1 channels by fenamate nonsteroidal anti-inflammatory drugs. *Pflugers Arch.* 459:579-92.

Jordt S E, Bautista D M, Chuang H H, McKemy D D, Zygmunt P M, Hogestatt E D, Meng I D, and Julius D (2004) Mustard oils and cannabinoids excite sensory nerve fibres through the TRP channel ANKTM1. *Nature* 427:260-265.

Kang K, Pulver S R, Panzano V C, Chang E C, Griffith L C, Theobald D L, Garrity P A (2010) Analysis of Drosophila TRPA1 reveals an ancient origin for human chemical nociception. *Nature* 464:597-600.

Karashima Y, Damann N, Prenen J, Talayera K, Segal A, Voets T, and Nilius B (2007) Bimodal action of menthol on the transient receptor potential channel TRPA1. *J Neurosci* 27:9874-9884.

Kremeyer B, Lopera F, Cox J J, Momin A, Rugiero F, Marsh S, Woods C G, Jones N G, Paterson K J, Fricker F R, et al. (2010) A gain-of-function mutation in TRPA1 causes familial episodic pain syndrome. *Neuron* 66:671-680.

Kwan K Y, Glazer J M, Corey D P, Rice F L, and Stucky C L (2009) TRPA1 modulates mechanotransduction in cutaneous sensory neurons. *J Neurosci* 29:4808-4819.

Lishko P V, Procko E, Jin X, Phelps C B, and Gaudet R (2007) The ankyrin repeats of TRPV1 bind multiple ligands and modulate channel sensitivity. *Neuron* 54:905-918.

Lee E, An S, Choi D, Moon S, Chang I (2007) Comparison of objective and sensory skin irritations of several cosmetic preservatives. *Contact Dermatitis* 56:131-6.

Macpherson L J, Geierstanger B H, Viswanath V, Bandell M, Eid S R, Hwang S, and Patapoutian A (2005) The pungency of garlic: activation of TRPA1 and TRPV1 in response to allicin. *Curr Biol.* 15:929-934.

Macpherson L J, Dubin A E, Evans M J, Marr F, Schultz P G, Cravatt B F, and Patapoutian A (2007) Noxious compounds activate TRPA1 ion channels through covalent modification of cysteines. *Nature* 445:541-545.

McNamara C R, Mandel-Brehm J, Bautista D M, Siemens J, Deranian K L, Zhao M, Hayward N J, Chong J A, Julius D, Moran M M, Fanger C M (2007) TRPA1 mediates formalin-induced pain. *Proc Natl Acad Sci USA* 104: 13525-30.

Petrus M, Peier A M, Bandell M, Hwang S W, Huynh T, Olney N, Jegla T, Patapoutian A (2007) A role of TRPA1 in mechanical hyperalgesia is revealed by pharmacological inhibition. *Mol. Pain.* 3:40.

Ramsey I S, Delling M, and Clapham D E (2006) An introduction to TRP channels. *Annu Rev Physiol* 68:619-647.

Sone T, Yamada H, Endo H (1990) Pharmacological studies of stinging caused by parabens. *J Jpn Cosmet Sci Soci* 14:8-16.

Sotomayor M, Corey D P, and Schulten K (2005) In search of the hair-cell gating spring elastic properties of ankyrin and cadherin repeats. *Structure* 13:669-682.

Story G M, Peier A M, Reeve A J, Eid S R, Mosbacher J, Hricik T R, Earley T J, Hergarden A C, Andersson D A, Hwang S W, et al. (2003) ANKTM1, a TRP-like channel expressed in nociceptive neurons, is activated by cold temperatures. *Cell* 112:819-829.

Taylor-Clark T E, Undem B J, Macglashan D W, Jr., Ghatta S, Carr M J, and Mc-Alexander M A (2008) Prostaglandin-induced activation of nociceptive neurons via direct interaction with transient receptor potential A1 (TRPA1). *Mol Pharmacol* 73:274-281.

Trevisani M, Siemens J, Materazzi S, Bautista D M, Nassini R, Campi B, Imamachi N, AndreE, Patacchini R, Cottrell G S, et al. (2007) 4-Hydroxynonenal, an endogenous aldehyde, causes pain and neurogenic inflammation through activation of the irritant receptor TRPA1. *Proc Natl Acad Sci USA* 104:13519-13524.

Wang Y Y, Chang R B, Waters H N, McKemy D D, Liman E R (2008) The nociceptor ion channel TRPA1 is potentiated and inactivated by permeating calcium ions. *J Biol Chem* 283:32691-703.

Wang Y Y, Chang R B, Liman E R (2010) TRPA1 is a component of the nociceptive response to CO2. *Neurosci* 30:12958-63.

Wei H, Hämäläinen M M, Saarnilehto M, Koivisto A, Pertovaara A (2009) Attenuation of mechanical hypersensitivity by an antagonist of the TRPA1 ion channel in diabetic animals. *Anesthesiology* 111:147-54.

Wei H, Koivisto A, Saarnilehto M, Chapman H, Kuokkanen K, Hao B, Huang J L, Wang Y X, Pertovaara A (2011) Spinal transient receptor potential ankyrin 1 channel contributes to central pain hypersensitivity in various pathophysiological conditions in the rat. *Pain* 152:582-91.

Wu L J, Sweet T B, Clapham D E (2010) International Union of Basic and Clinical Pharmacology. LXXVI. Current progress in the mammalian TRP ion channel family. *Pharmacol Rev* 62:381-404.

Zurborg S, Yurgionas B, Jira J A, Caspani O, and Heppenstall P A (2007) Direct activation of the ion channel TRPA1 by $Ca^{2+}$. *Nat Neurosci* 10:277-279.

The invention claimed is:

1. A method of soothing skin irritation in a human in need thereof, comprising administering to the human an effective amount of a compound of Formula I.2.1:

(I.2.1)

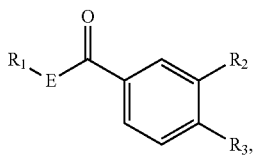

or a pharmaceutically acceptable derivative thereof, wherein:
E is O or N(T$_3$);
R$_1$ has a structure as shown in formula (i), (ii), (iii) or (iv):

(i)

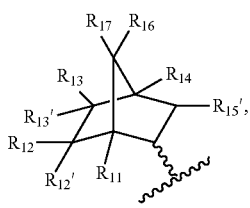

wherein:
R$_{11}$, R$_{12}$, R$_{13}$, and R$_{14}$ are each independently —H, —(C$_1$-C$_4$)alkyl, —(C$_2$-C$_4$)alkenyl, —(C$_2$-C$_4$)alkynyl, —OR$_7$, —SR$_7$, —C(halo)$_3$, —CH(halo)$_2$, —CH$_2$(halo), —CN, -halo, —N$_3$, —NO$_2$, —N(R$_7$)$_2$, —N(R$_7$)OH, —C(=O)R$_7$, —C(=O)N(R$_7$)$_2$, —C(=O)OR$_7$, —OC(=O)R$_7$, —S(=O)R$_7$, or —S(=O)$_2$R$_7$;
R$_{12}$', R$_{13}$', and R$_{15}$' are each independently —H or —(C$_1$-C$_3$)alkyl; and
R$_{16}$ and R$_{17}$ are each independently —H, —OH, —(C$_1$-C$_2$)alkyl, -halo, or —C(halo)$_3$; or (ii)

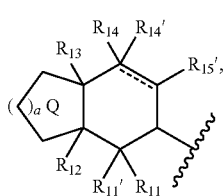

wherein:
R$_{11}$, R$_{12}$, R$_{13}$, and R$_{14}$ are each independently —H, —(C$_1$-C$_4$)alkyl, —(C$_2$-C$_4$)alkenyl, —(C$_2$-C$_4$)alkynyl, —OR$_7$, —SR$_7$, —C(halo)$_3$, —CH(halo)$_2$, —CH$_2$(halo), —CN, -halo, —N$_3$, —NO$_2$, —N(R$_7$)$_2$, —N(R$_7$)OH, —C(=O)R$_7$, —C(=O)N(R$_7$)$_2$, —C(=O)OR$_7$, —OC(=O)R$_7$, —S(=O)R$_7$, or —S(=O)$_2$R$_7$;
the dashed line between R$_{14}$' and R$_{15}$' denotes the presence or absence of a bond, wherein:
  (a) R$_{14}$' and R$_{15}$' are present if the bond is absent; or
  (b) R$_{14}$' and R$_{15}$' are absent if the bond is present;
R$_{11}$', R$_{14}$', and R$_{15}$', if present, are each independently —H or —(C$_1$-C$_3$)alkyl; and
a is 2 or 3; wherein:
  (a) if a is 2, the ring denoted as Q is —(C$_6$)cycloalkyl, or —(C$_6$)cycloalkenyl, each of which is unsubstituted or substituted with 1, 2 or 3 independently selected R$_5$ groups;
  (b) if a is 3, the ring denoted as Q is —(C$_7$)cycloalkyl, or —(C$_7$)cycloalkenyl, each of which is unsubstituted or substituted with 1, 2, 3 or 4 independently selected R$_5$ groups; or (iii)

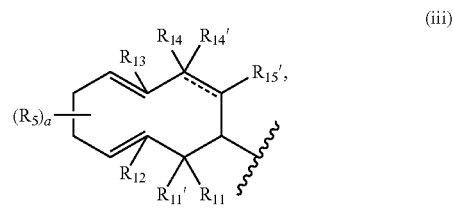

wherein:
R$_{11}$, R$_{12}$, R$_{13}$, and R$_{14}$ are each independently —H, —(C$_1$-C$_4$)alkyl, —(C$_2$-C$_4$)alkenyl, —(C$_2$-C$_4$)alkynyl, —OR$_7$, —SR$_7$, —C(halo)$_3$, —CH(halo)$_2$, —CH$_2$(halo), —CN, -halo, —N$_3$, —NO$_2$, —N(R$_7$)$_2$, —N(R$_7$)OH, —C(=O)R$_7$, —C(=O)N(R$_7$)$_2$, —C(=O)OR$_7$, —OC(=O)R$_7$, —S(=O)R$_7$, or —S(=O)$_2$R$_7$;
the dashed line between R$_{14}$' and R$_{15}$' denotes the presence or absence of a bond, wherein:
  (a) R$_{14}$' and R$_{15}$' are present if the bond is absent; or
  (b) R$_{14}$' and R$_{15}$' are absent if the bond is present;
R$_{11}$', R$_{14}$', and R$_{15}$', if present, are each independently —H or —(C$_1$-C$_3$)alkyl; and
a is 1, 2 or 3; or (iv)

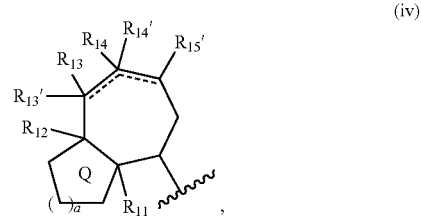

wherein:
R$_{11}$, R$_{12}$, R$_{13}$, and R$_{14}$ are each independently —H, —(C$_1$-C$_4$)alkyl, —(C$_2$-C$_4$)alkenyl, —(C$_2$-C$_4$)alkynyl, —OR$_7$, —SR$_7$, —C(halo)$_3$, —CH(halo)$_2$, —CH$_2$(halo), —CN, -halo, —N$_3$, —NO$_2$, —N(R$_7$)$_2$, —N(R$_7$)OH, —C(=O)R$_7$, —C(=O)N(R$_7$)$_2$, —C(=O)OR$_7$, —OC(=O)R$_7$, —S(=O)R$_7$, or —S(=O)$_2$R$_7$;
the dashed lines between R$_{13}$' and R$_{14}$' and R$_{14}$' and R$_{15}$' each denote the presence or absence of a bond, wherein:
  (a) R$_{13}$', R$_{14}$' and R$_{15}$' are each present if both bonds are absent; or
  (b) R$_{13}$' and R$_{14}$' are each absent and R$_{15}$' is present if the bond between R$_{13}$' and R$_{14}$' is present and the bond between R$_{14}$' and R$_{15}$' is absent; or
  (c) R$_{13}$' is present and R$_{14}$' and R$_{15}$' are absent if the bond between R$_{13}$' and R$_{14}$' is absent and the bond between R$_{14}$' and R$_{15}$' is present;
R$_{13}$', R$_{14}$', R$_{15}$', if present, are each independently —H or —(C$_1$-C$_3$)alkyl; and a is 1 or 2; wherein:
(a) if a is 1, the ring denoted as Q is —(C$_5$) cycloalkyl, or —(C$_5$)cycloalkenyl, each of which is unsubstituted or substituted with 1, 2 or 3 independently selected R$_5$ groups;
(b) if a is 2, the ring denoted as Q is —(C$_6$) cycloalkyl, or —(C$_6$)cycloalkenyl, each of which is unsubstituted or substituted with 1, 2 or 3 independently selected R$_5$ groups;

R$_2$ and R$_3$ are each independently -halo, —CN, —NO$_2$, -OT$_3$, —OC(=O)T$_3$, —C(=O)T$_3$, —C(=O)OT$_3$, —C(=O)N(T$_1$)(T$_2$), —(C$_1$-C$_3$)alkyl, —(C$_2$-C$_3$)alkenyl, —(C$_2$-C$_3$)alkynyl, or —(C$_1$-C$_3$)alkoxy,
wherein the —(C$_1$-C$_3$)alkyl, —(C$_2$-C$_3$)alkenyl, —(C$_2$-C$_3$)alkynyl, and —(C$_1$-C$_3$)alkoxy are each unsubstituted or substituted with 1 or 2 independently selected R$_5$ groups;

each R$_5$ is independently —H, —(C$_1$-C$_3$)alkyl, —(C$_3$) alkenyl, —(C$_3$)alkynyl, —OR$_7$, —C(halo)$_3$, —CH(halo)$_2$, —CH$_2$(halo), —CN, -halo, —N$_3$, —NO$_2$, —N(R$_7$)$_2$, —N(R$_7$)OH, —C(=O)R$_7$, or —C(=O) OR$_7$;

each R$_7$ is independently —H, or —CH$_3$;

each T$_1$, T$_2$, and T$_3$ is independently —H or —CH$_3$; and each halo is independently —F, —Cl, —Br, or —I.

2. The method of claim 1, wherein the compound of Formula I.2.1 is:

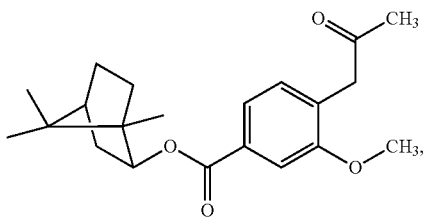

or a pharmaceutically acceptable derivative thereof.

3. The method of claim 1, wherein the compound or a pharmaceutically acceptable derivative thereof is administered to the human in a personal-care product.

4. The method of claim 3, wherein the personal-care product is a cosmetic product or a wound dressing.

5. The method of claim 4, wherein the personal-care product is a cosmetic product, and wherein the cosmetic product is an oral hygiene composition, a skin care composition, or a hair care composition.

6. The method of claim 4, wherein the personal-care product is a cosmetic product, and wherein the cosmetic product is an insect repellent, a lotion, a shaving cream, a post-shaving preparation, a shampoo, a conditioner, a facial cleanser, a soap, a bath oil, a bath foam, an antiperspirant, a deodorant, a toothpaste, a mouthwash, a dental floss, a chewing gum, or a breath freshener.

7. The method of claim 3, wherein the personal-care product comprises a personal-care agent, wherein the personal-care agent is an emulsifier, a detergent, a preservative, an anti-aging compound, a depilation agent, or a peeling agent.

8. A method of modulating the taste of a food product to a human, comprising combining a food product and a compound of Formula I.2.1:

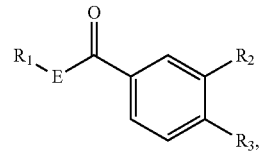

or a pharmaceutically acceptable derivative thereof, wherein:
E is O or N(T$_3$);
R$_1$ has a structure as shown in formula (i), (ii), (iii) or (iv):

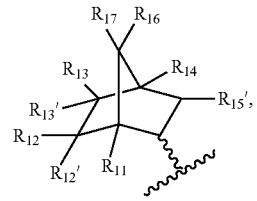

wherein:
R$_{11}$, R$_{12}$, R$_{13}$, and R$_{14}$ are each independently —H, —(C$_1$-C$_4$)alkyl, —(C$_2$-C$_4$)alkenyl, —(C$_2$-C$_4$) alkynyl, —OR$_7$, —SR$_7$, —C(halo)$_3$, —CH(halo)$_2$, —CH$_2$(halo), —CN, -halo, —N$_3$, —NO$_2$, —N(R$_7$)$_2$, —N(R$_7$)OH, —C(=O)R$_7$, —C(=O)N(R$_7$)$_2$, —C(=O)OR$_7$, —OC(=O)R$_7$, —S(=O)R$_7$, or —S(=O)$_2$R$_7$;
R$_{12}$', R$_{13}$', and R$_{15}$' are each independently —H or —(C$_1$-C$_3$)alkyl; and
R$_{16}$ and R$_{17}$ are each independently —H, —OH, —(C$_1$-C$_2$)alkyl, -halo, or —C(halo)$_3$; or

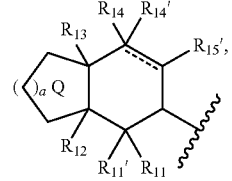

wherein:
R$_{11}$, R$_{12}$, R$_{13}$, and R$_{14}$ are each independently —H, —(C$_1$-C$_4$)alkyl, —(C$_2$-C$_4$)alkenyl, —(C$_2$-C$_4$) alkynyl, —OR$_7$, —SR$_7$, —C(halo)$_3$, —CH(halo)$_2$, —CH$_2$(halo), —CN, -halo, —N$_3$, —NO$_2$, —N(R$_7$)$_2$, —N(R$_7$)OH, —C(=O)R$_7$, —C(=O)N(R$_7$)$_2$, —C(=O)OR$_7$, —OC(=O)R$_7$, —S(=O)R$_7$, or —S(=O)$_2$R$_7$;
the dashed line between R$_{14}$' and R$_{15}$' denotes the presence or absence of a bond, wherein:
(a) R$_{14}$' and R$_{15}$' are present if the bond is absent; or
(b) R$_{14}$' and R$_{15}$' are absent if the bond is present;
R$_{11}$', R$_{14}$', and R$_{15}$', if present, are each independently —H or —(C$_1$-C$_3$)alkyl; and
a is 2 or 3; wherein:
(a) if a is 2, the ring denoted as Q is —(C$_6$) cycloalkyl, or —(C$_6$)cycloalkenyl, each of which is unsubstituted or substituted with 1, 2 or 3 independently selected $R_5$ groups;

(b) if a is 3, the ring denoted as Q is —($C_7$)cycloalkyl, or —($C_7$)cycloalkenyl, each of which is unsubstituted or substituted with 1, 2, 3 or 4 independently selected $R_5$ groups; or

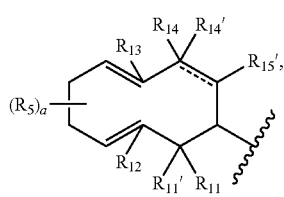
(iii)

wherein:
$R_{11}$, $R_{12}$, $R_{13}$, and $R_{14}$ are each independently —H, —($C_1$-$C_4$)alkyl, —($C_2$-$C_4$)alkenyl, —($C_2$-$C_4$)alkynyl, —$OR_7$, —$SR_7$, —C(halo)$_3$, —CH(halo)$_2$, —CH$_2$(halo), —CN, -halo, —$N_3$, —$NO_2$, —N($R_7$)$_2$, —N($R_7$)OH, —C(=O)$R_7$, —C(=O)N($R_7$)$_2$, —C(=O)O$R_7$, —OC(=O)$R_7$, —S(=O)$R_7$, or —S(=O)$_2$$R_7$;

the dashed line between $R_{14'}$ and $R_{15'}$ denotes the presence or absence of a bond, wherein:
(a) $R_{14}'$ and $R_{15}'$ are present if the bond is absent; or
(b) $R_{14}'$ and $R_{15}'$ are absent if the bond is present;
$R_{11}'$, $R_{14}'$, and $R_{15}'$, if present, are each independently —H or —($C_1$-$C_3$)alkyl; and
a is 1, 2 or 3; or

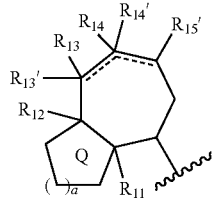
(iv)

wherein:
$R_{11}$, $R_{12}$, $R_{13}$, and $R_{14}$ are each independently —H, —($C_1$-$C_4$)alkyl, —($C_2$-$C_4$)alkenyl, —($C_2$-$C_4$)alkynyl, —$OR_7$, —$SR_7$, —C(halo)$_3$, —CH(halo)$_2$, —CH$_2$(halo), —CN, -halo, —$N_3$, —$NO_2$, —N($R_7$)$_2$, —N($R_7$)OH, —C(=O)$R_7$, —C(=O)N($R_7$)$_2$, —C(=O)O$R_7$, —OC(=O)$R_7$, —S(=O)$R_7$, or —S(=O)$_2$$R_7$;

the dashed lines between $R_{13}'$ and $R_{14}'$ and $R_{14}'$ and $R_{15}'$ each denote the presence or absence of a bond, wherein:
(a) $R_{13}'$, $R_{14}'$ and $R_{15}'$ are each present if both bonds are absent; or
(b) $R_{13}'$ and $R_{14}'$ are each absent and $R_{15}'$ is present if the bond between $R_{13}'$ and $R_{14}'$ is present and the bond between $R_{14}'$ and $R_{15}'$ is absent; or
(c) $R_{13}'$ is present and $R_{14}'$ and $R_{15}'$ are absent if the bond between $R_{13}'$ and $R_{14}'$ is absent and the bond between $R_{14}'$ and $R_{15}'$ is present;
$R_{13}'$, $R_{14}'$, and $R_{15}'$, if present, are each independently —H or —($C_1$-$C_3$)alkyl; and a is 1 or 2; wherein:
(a) if a is 1, the ring denoted as Q is —($C_5$)cycloalkyl, or —($C_5$)cycloalkenyl, each of which is unsubstituted or substituted with 1, 2 or 3 independently selected $R_5$ groups;
(b) if a is 2, the ring denoted as Q is —($C_6$)cycloalkyl, or —($C_6$)cycloalkenyl, each of which is unsubstituted or substituted with 1, 2 or 3 independently selected $R_5$ groups;

$R_2$ and $R_3$ are each independently -halo, —CN, —$NO_2$, -$OT_3$, —OC(=O)$T_3$, —C(=O)$T_3$, —C(=O)O$T_3$, —C(=O)N($T_1$)($T_2$), —($C_1$-$C_3$)alkyl, —($C_2$-$C_3$)alkenyl, —($C_2$-$C_3$)alkynyl, or —($C_1$-$C_3$)alkoxy,
wherein the —($C_1$-$C_3$)alkyl, —($C_2$-$C_3$)alkenyl, —($C_2$-$C_3$)alkynyl, and —($C_1$-$C_3$)alkoxy are each unsubstituted or substituted with 1 or 2 independently selected $R_5$ groups;

each $R_5$ is independently —H, —($C_1$-$C_3$)alkyl, —($C_3$)alkenyl, —($C_3$)alkynyl, —$OR_7$, —C(halo)$_3$, —CH(halo)$_2$, —CH$_2$(halo), —CN, -halo, —$N_3$, —$NO_2$, —N($R_7$)$_2$, —N($R_7$)OH, —C(=O)$R_7$, or —C(=O)O$R_7$;

each $R_7$ is independently —H, or —$CH_3$;

each $T_1$, $T_2$, and $T_3$ is independently —H or —$CH_3$; and each halo is independently —F, —Cl, —Br, or —I.

9. The method of claim 8, wherein the compound of Formula I.2.1 is:

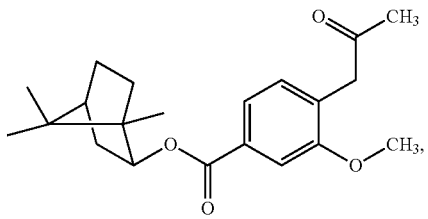

or a pharmaceutically acceptable derivative thereof.

10. The method of claim 8, wherein the food product is a beverage.

11. The method of claim 10, wherein the beverage is wine, coffee, fruit juice, or tea.

12. The method of claim 8, wherein the food product is an edible.

13. The method of claim 12, wherein the edible is a bakery product, a dairy product, a fruit product, a vegetable product, a convenience meal, a sweet, or a snack food.

14. The method of claim 8, wherein the food product comprises one or more ingredients with a strong taste, a pungent taste, or an astringent taste, or any combinations thereof.

15. An in vitro method of inhibiting TRPA1, comprising contacting TRPA1 with a compound of Formula I.2.1:

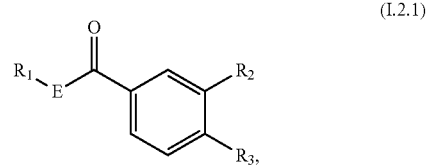
(I.2.1)

or a pharmaceutically acceptable derivative thereof, wherein:

E is O or N(T$_3$);

R$_1$ has a structure as shown in formula (i), (ii), (iii) or (iv):

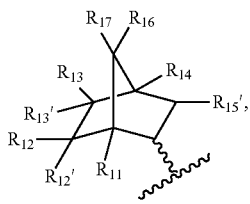

(i)

wherein:
R$_{11}$, R$_{12}$, R$_{13}$, and R$_{14}$ are each independently —H, —(C$_1$-C$_4$)alkyl, —(C$_2$-C$_4$)alkenyl, —(C$_2$-C$_4$)alkynyl, —OR$_7$, —SR$_7$, —C(halo)$_3$, —CH(halo)$_2$, —CH$_2$(halo), —CN, -halo, —N$_3$, —NO$_2$, —N(R$_7$)$_2$, —N(R$_7$)OH, —C(=O)R$_7$, —C(=O)N(R$_7$)$_2$, —C(=O)OR$_7$, —OC(=O)R$_7$, —S(=O)R$_7$, or —S(=O)$_2$R$_7$;

R$_{12}'$, R$_{13}'$, and R$_{15}'$ are each independently —H or —(C$_1$-C$_3$)alkyl; and R$_{16}$ and R$_{17}$ are each independently —H, —OH, —(C$_1$-C$_2$)alkyl, -halo, or —C(halo)$_3$; or

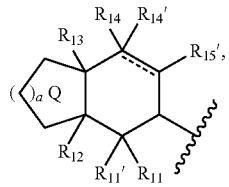

(ii)

wherein:
R$_{11}$, R$_{12}$, R$_{13}$, and R$_{14}$ are each independently —H, —(C$_1$-C$_4$)alkyl, —(C$_2$-C$_4$)alkenyl, —(C$_2$-C$_4$)alkynyl, —OR$_7$, —SR$_7$, —C(halo)$_3$, —CH(halo)$_2$, —CH$_2$(halo), —CN, -halo, —N$_3$, —NO$_2$, —N(R$_7$)$_2$, —N(R$_7$)OH, —C(=O)R$_7$, —C(=O)N(R$_7$)$_2$, —C(=O)OR$_7$, —OC(=O)R$_7$, —S(=O)R$_7$, or —S(=O)$_2$R$_7$;

the dashed line between R$_{14}'$ and R$_{15}'$ denotes the presence or absence of a bond, wherein:
(a) R$_{14}'$ and R$_{15}'$ are present if the bond is absent; or
(b) R$_{14}'$ and R$_{15}'$ are absent if the bond is present;

R$_{11}'$, R$_{14}'$, and R$_{15}'$, if present, are each independently —H or —(C$_1$-C$_3$)alkyl; and a is 2 or 3; wherein:
(a) if a is 2, the ring denoted as Q is —(C$_6$)cycloalkyl, or —(C$_6$)cycloalkenyl, each of which is unsubstituted or substituted with 1, 2 or 3 independently selected R$_5$ groups;
(b) if a is 3, the ring denoted as Q is —(C$_7$)cycloalkyl, or —(C$_7$)cycloalkenyl, each of which is unsubstituted or substituted with 1, 2, 3 or 4 independently selected R$_5$ groups; or

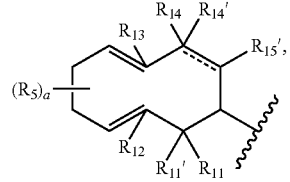

(iii)

wherein:
R$_{11}$, R$_{12}$, R$_{13}$, and R$_{14}$ are each independently —H, —(C$_1$-C$_4$)alkyl, —(C$_2$-C$_4$)alkenyl, —(C$_2$-C$_4$)alkynyl, —OR$_7$, —SR$_7$, —C(halo)$_3$, —CH(halo)$_2$, —CH$_2$(halo), —CN, -halo, —N$_3$, —NO$_2$, —N(R$_7$)$_2$, —N(R$_7$)OH, —C(=O)R$_7$, —C(=O)N(R$_7$)$_2$, —C(=O)OR$_7$, —OC(=O)R$_7$, —S(=O)R$_7$, or —S(=O)$_2$R$_7$;

the dashed line between R$_{14}'$ and R$_{15}'$ denotes the presence or absence of a bond, wherein:
(a) R$_{14}'$ and R$_{15}'$ are present if the bond is absent; or
(b) R$_{14}'$ and R$_{15}'$ are absent if the bond is present;

R$_{11}'$, R$_{14}'$, and R$_{15}'$, if present, are each independently —H or —(C$_1$-C$_3$)alkyl; and a is 1, 2 or 3; or

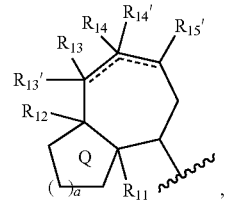

(iv)

wherein:
R$_{11}$, R$_{12}$, R$_{13}$, and R$_{14}$ are each independently —H, —(C$_1$-C$_4$)alkyl, —(C$_2$-C$_4$)alkenyl, —(C$_2$-C$_4$)alkynyl, —OR$_7$, —SR$_7$, —C(halo)$_3$, —CH(halo)$_2$, —CH$_2$(halo), —CN, -halo, —N$_3$, —NO$_2$, —N(R$_7$)$_2$, —N(R$_7$)OH, —C(=O)R$_7$, —C(=O)N(R$_7$)$_2$, —C(=O)OR$_7$, -OC(=O)R$_7$, —S(=O)R$_7$, or —S(=O)$_2$R$_7$;

the dashed lines between R$_{13}'$ and R$_{14}'$ and R$_{14}'$ and R$_{15}'$ each denote the presence or absence of a bond, wherein:
(a) R$_{13}'$, R$_{14}'$ and R$_{15}'$ are each present if both bonds are absent; or
(b) R$_{13}'$ and R$_{14}'$ are each absent and R$_{15}'$ is present if the bond between R$_{13}'$ and R$_{14}'$ is present and the bond between R$_{14}'$ and R$_{15}'$ is absent; or
(c) R$_{13}'$ is present and R$_{14}'$ and R$_{15}'$ are absent if the bond between R$_{13}'$ and R$_{14}'$ is absent and the bond between R$_{14}'$ and R$_{15}'$ is present;

R$_{13}'$, R$_{14}'$, and R$_{15}'$, if present, are each independently —H or —(C$_1$-C$_3$)alkyl; and a is 1 or 2; wherein:
(a) if a is 1, the ring denoted as Q is —(C$_5$)cycloalkyl, or —(C$_5$)cycloalkenyl, each of which is unsubstituted or substituted with 1, 2 or 3 independently selected R$_5$ groups;
(b) if a is 2, the ring denoted as Q is —(C$_6$)cycloalkyl, or —(C$_6$)cycloalkenyl, each of which is unsubstituted or substituted with 1, 2 or 3 independently selected $R_5$ groups;

$R_2$ and $R_3$ are each independently -halo, —CN, —NO$_2$, -OT$_3$, —OC(=O)T$_3$, —C(=O)T$_3$, —C(=O)OT$_3$, —C(=O)N(T$_1$)(T$_2$), —(C$_1$-C$_3$)alkyl, —(C$_2$-C$_3$)alkenyl, —(C$_2$-C$_3$)alkynyl, or —(C$_1$-C$_3$)alkoxy, wherein the —(C$_1$-C$_3$)alkyl, —(C$_2$-C$_3$)alkenyl, —(C$_2$-C$_3$)alkynyl, and —(C$_1$-C$_3$)alkoxy are each unsubstituted or substituted with 1 or 2 independently selected $R_5$ groups;

each $R_5$ is independently —H, —(C$_1$-C$_3$)alkyl, —(C$_3$)alkenyl, —(C$_3$)alkynyl, —OR$_7$, —C(halo)$_3$, —CH(halo)$_2$, —CH$_2$(halo), —CN, -halo, —N$_3$, —NO$_2$, —N(R$_7$)$_2$, —N(R$_7$)OH, —C(=O)R$_7$, or —C(=O)OR$_7$;

each $R_7$ is independently —H, or —CH$_3$;

each $T_1$, $T_2$, and $T_3$ is independently —H or —CH$_3$; and each halo is independently —F, —Cl, —Br, or —I.

16. The method of claim 15, wherein the compound of Formula I.2.1 is:

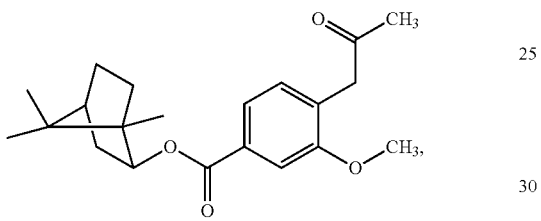

or a pharmaceutically acceptable derivative thereof.

17. A food composition, comprising one or more food ingredients and a compound of Formula I.2.1:

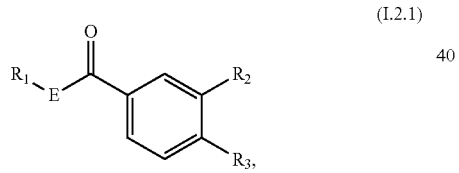

(I.2.1)

or a pharmaceutically acceptable derivative thereof, wherein:

E is O or N(T$_3$);

$R_1$ has a structure as shown in formula (i), (ii), (iii) or (iv):

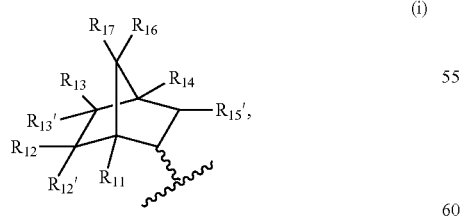

(i)

wherein:

$R_{11}$, $R_{12}$, $R_{13}$, and $R_{14}$ are each independently —H, —(C$_1$-C$_4$)alkyl, —(C$_2$-C$_4$)alkenyl, —(C$_2$-C$_4$)alkynyl, —OR$_7$, —SR$_7$, —C(halo)$_3$, —CH(halo)$_2$, —CH$_2$(halo), —CN, -halo, —N$_3$, —NO$_2$, —N(R$_7$)$_2$, —N(R$_7$)OH, —C(=O)R$_7$, —C(=O)N(R$_7$)$_2$, —C(=O)OR$_7$, —OC(=O)R$_7$, —S(=O)R$_7$, or —S(=O)$_2$R$_7$;

$R_{12}'$, $R_{13}'$, and $R_{15}'$ are each independently —H or —(C$_1$-C$_3$)alkyl; and $R_{16}$ and $R_{17}$ are each independently —H, —OH, —(C$_1$-C$_2$)alkyl, -halo, or —C(halo)$_3$; or

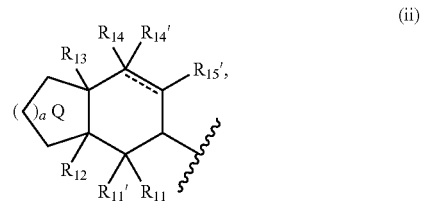

(ii)

wherein:

$R_{11}$, $R_{12}$, $R_{13}$, and $R_{14}$ are each independently —H, —(C$_1$-C$_4$)alkyl, —(C$_2$-C$_4$)alkenyl, —(C$_2$-C$_4$)alkynyl, —OR$_7$, —SR$_7$, —C(halo)$_3$, —CH(halo)$_2$, —CH$_2$(halo), —CN, -halo, —N$_3$, —NO$_2$, —N(R$_7$)$_2$, —N(R$_7$)OH, —C(=O)R$_7$, —C(=O)N(R$_7$)$_2$, —C(=O)OR$_7$, —OC(=O)R$_7$, —S(=O)R$_7$, or —S(=O)$_2$R$_7$;

the dashed line between $R_{14}'$ and $R_{15}'$ denotes the presence or absence of a bond, wherein:

(a) $R_{14}'$ and $R_{15}'$ are present if the bond is absent; or (b) $R_{14}'$ and $R_{15}'$ are absent if the bond is present;

$R_{11}'$, $R_{14}'$, and $R_{15}'$, if present, are each independently —H or —(C$_1$-C$_3$)alkyl; and a is 2 or 3; wherein:

(a) if a is 2, the ring denoted as Q is —(C$_6$)cycloalkyl, or —(C$_6$)cycloalkenyl, each of which is unsubstituted or substituted with 1, 2 or 3 independently selected $R_5$ groups;

(b) if a is 3, the ring denoted as Q is —(C$_7$)cycloalkyl, or —(C$_7$)cycloalkenyl, each of which is unsubstituted or substituted with 1, 2, 3 or 4 independently selected $R_5$ groups; or

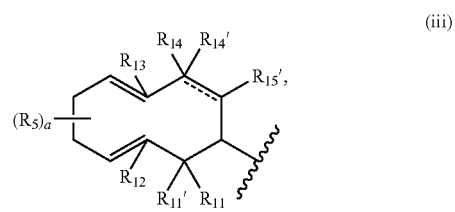

(iii)

wherein:

$R_{11}$, $R_{12}$, $R_{13}$, and $R_{14}$ are each independently —H, —(C$_1$-C$_4$)alkyl, —(C$_2$-C$_4$)alkenyl, —(C$_2$-C$_4$)alkynyl, —OR$_7$, —SR$_7$, —C(halo)$_3$, —CH(halo)$_2$, —CH$_2$(halo), —CN, -halo, —N$_3$, —NO$_2$, —N(R$_7$)$_2$, —N(R$_7$)OH, —C(=O)R$_7$, —C(=O)N(R$_7$)$_2$, —C(=O)OR$_7$, —OC(=O)R$_7$, —S(=O)R$_7$, or —S(=O)$_2$R$_7$;

the dashed line between $R_{14}'$ and $R_{15}'$ denotes the presence or absence of a bond, wherein:

(a) $R_{14}'$ and $R_{15}'$ are present if the bond is absent; or (b) $R_{14}'$ and $R_{15}'$ are absent if the bond is present;

$R_{11}'$, $R_{14}'$, and $R_{15}'$, if present, are each independently —H or —$(C_1-C_3)$alkyl; and a is 1, 2 or 3; or

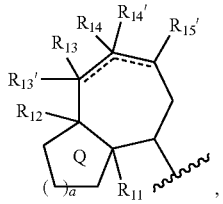

(iv)

wherein:

$R_{11}$, $R_{12}$, $R_{13}$, and $R_{14}$ are each independently —H, —$(C_1-C_4)$alkyl, —$(C_2-C_4)$alkenyl, —$(C_2-C_4)$alkynyl, —$OR_7$, —$SR_7$, —$C(halo)_3$, —$CH(halo)_2$, —$CH_2(halo)$, —CN, -halo, —$N_3$, —$NO_2$, —$N(R_7)_2$, —$N(R_7)OH$, —$C(=O)R_7$, —$C(=O)N(R_7)_2$, —$C(=O)OR_7$, —$OC(=O)R_7$, —$S(=O)R_7$, or —$S(=O)_2R_7$;

the dashed lines between $R_{13}'$ and $R_{14}'$ and $R_{14}'$ and $R_{15}'$ each denote the presence or absence of a bond, wherein:

(a) $R_{13}'$, $R_{14}'$ and $R_{15}'$ are each present if both bonds are absent; or (b) $R_{13}'$ and $R_{14}'$ are each absent and $R_{15}'$ is present if the bond between $R_{13}'$ and $R_{14}'$ is present and the bond between $R_{14}'$ and $R_{15}'$ is absent; or (c) $R_{13}'$ is present and $R_{14}'$ and $R_{15}'$ are absent if the bond between $R_{13}'$ and $R_{14}'$ is absent and the bond between $R_{14}'$ and $R_{15}'$ is present;

$R_{13}'$, $R_{14}'$, and $R_{15}'$, if present, are each independently —H or —$(C_1-C_3)$alkyl; and a is 1 or 2; wherein:

(a) if a is 1, the ring denoted as Q is —$(C_5)$cycloalkyl, or —$(C_5)$cycloalkenyl, each of which is unsubstituted or substituted with 1, 2 or 3 independently selected $R_5$ groups;

(b) if a is 2, the ring denoted as Q is —$(C_6)$cycloalkyl, or —$(C_6)$cycloalkenyl, each of which is unsubstituted or substituted with 1, 2 or 3 independently selected $R_5$ groups;

$R_2$ and $R_3$ are each independently -halo, —CN, —$NO_2$, -$OT_3$, —$OC(=O)T_3$, —$C(=O)T_3$, —$C(=O)OT_3$, —$C(=O)N(T))(T_2)$, —$(C_1-C_3)$alkyl, —$(C_2-C_3)$alkenyl, —$(C_2-C_3)$alkynyl, or —$(C_1-C_3)$alkoxy, wherein the —$(C_1-C_3)$alkyl, —$(C_2-C_3)$alkenyl, —$(C_2-C_3)$alkynyl, and —$(C_1-C_3)$alkoxy are each unsubstituted or substituted with 1 or 2 independently selected $R_5$ groups;

each $R_5$ is independently —H, —$(C_1-C_3)$alkyl, —$(C_3)$alkenyl, —$(C_3)$alkynyl, —$OR_7$, —$C(halo)_3$, —$CH(halo)_2$, —$CH_2(halo)$, —CN, -halo, —$N_3$, —$NO_2$, —$N(R_7)_2$, —$N(R_7)OH$, —$C(=O)R_7$, or —$C(=O)OR_7$;

each $R_7$ is independently —H, or —$CH_3$;

each $T_1$, $T_2$, and $T_3$ is independently —H or —$CH_3$; and each halo is independently —F, —Cl, —Br, or —I.

18. The food composition of claim 17, wherein the compound of Formula I.2.1 is:

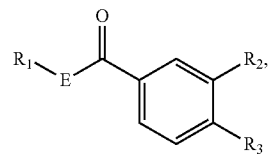

(I.2.1)

or a pharmaceutically acceptable derivative thereof.

19. The food composition of claim 17, wherein the food composition is a beverage.

20. The food composition of claim 19, wherein the beverage is wine, coffee, fruit juice, or tea.

21. The food composition of claim 17, wherein the food composition is an edible.

22. The food composition of claim 21, wherein the edible is a bakery product, a dairy product, a fruit product, a vegetable product, a convenience meal, a sweet, or a snack food.

23. The food composition of claim 17, wherein the food composition comprises one or more ingredients with a strong taste, a pungent taste, or an astringent taste, or any combinations thereof.

24. A personal-care composition, comprising a personal-care agent and a compound of Formula I.2.1:

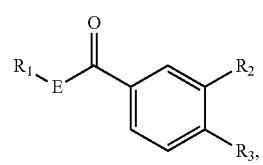

(I.2.1)

or a pharmaceutically acceptable derivative thereof, wherein:

E is O or $N(T_3)$;

$R_1$ has a structure as shown in formula (i), (ii), (iii) or (iv):

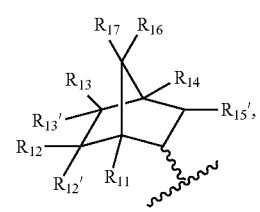

(i)

wherein:

$R_{11}$, $R_{12}$, $R_{13}$, and $R_{14}$ are each independently —H, —$(C_1-C_4)$alkyl, —$(C_2-C_4)$alkenyl, —$(C_2-C_4)$alkynyl, —$OR_7$, —$SR_7$, —$C(halo)_3$, —$CH(halo)_2$, —$CH_2(halo)$, —CN, -halo, —$N_3$, —$NO_2$, —$N(R_7)_2$, —$N(R_7)OH$, —$C(=O)R_7$, —$C(=O)N(R_7)_2$, —$C(=O)OR_7$, —$OC(=O)R_7$, —$S(=O)R_7$, or —$S(=O)_2R_7$;

$R_{12}'$, $R_{13}'$, and $R_{15}'$ are each independently —H or —$(C_1-C_3)$alkyl; and $R_{16}$ and $R_{17}$ are each independently —H, —OH, —$(C_1-C_2)$alkyl, -halo, or —$C(halo)_3$; or

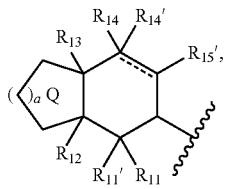

(ii)

wherein:

$R_{11}$, $R_{12}$, $R_{13}$, and $R_{14}$ are each independently —H, —$(C_1$-$C_4)$alkyl, —$(C_2$-$C_4)$alkenyl, —$(C_2$-$C_4)$alkynyl, —$OR_7$, —$SR_7$, —$C(halo)_3$, —$CH(halo)_2$, —$CH_2(halo)$, —CN, -halo, —$N_3$, —$NO_2$, —$N(R_7)_2$, —$N(R_7)OH$, —$C(=O)R_7$, —$C(=O)N(R_7)_2$, —$C(=O)OR_7$, —$OC(=O)R_7$, —$S(=O)R_7$, or —$S(=O)_2R_7$;

the dashed line between $R_{14}'$ and $R_{15}'$ denotes the presence or absence of a bond, wherein:

(a) $R_{14}'$ and $R_{15}'$ are present if the bond is absent; or (b) $R_{14}'$ and $R_{15}'$ are absent if the bond is present;

$R_{11}'$, $R_{14}'$, and $R_{15}'$, if present, are each independently —H or —$(C_1$-$C_3)$alkyl; and a is 2 or 3; wherein:

(a) if a is 2, the ring denoted as Q is —$(C_6)$cycloalkyl, or —$(C_6)$cycloalkenyl, each of which is unsubstituted or substituted with 1, 2 or 3 independently selected $R_5$ groups;

(b) if a is 3, the ring denoted as Q is —$(C_7)$cycloalkyl, or —$(C_7)$cycloalkenyl, each of which is unsubstituted or substituted with 1, 2, 3 or 4 independently selected $R_5$ groups; or

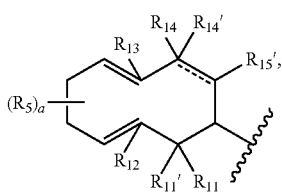

(iii)

wherein:

$R_{11}$, $R_{12}$, $R_{13}$, and $R_{14}$ are each independently —H, —$(C_1$-$C_4)$alkyl, —$(C_2$-$C_4)$alkenyl, —$(C_2$-$C_4)$alkynyl, —$OR_7$, —$SR_7$, —$C(halo)_3$, —$CH(halo)_2$, —$CH_2(halo)$, —CN, -halo, —$N_3$, —$NO_2$, —$N(R_7)_2$, —$N(R_7)OH$, —$C(=O)R_7$, —$C(=O)N(R_7)_2$, —$C(=O)OR_7$, —$OC(=O)R_7$, —$S(=O)R_7$, or —$S(=O)_2R_7$;

the dashed line between $R_{14}'$ and $R_{15}'$ denotes the presence or absence of a bond, wherein:

(a) $R_{14}'$ and $R_{15}'$ are present if the bond is absent; or (b) $R_{14}'$ and $R_{15}'$ are absent if the bond is present;

$R_{11}'$, $R_{14}'$, and $R_{15}'$, if present, are each independently —H or —$(C_1$-$C_3)$alkyl; and a is 1, 2 or 3; or

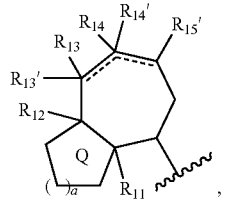

(iv)

wherein:

$R_{11}$, $R_{12}$, $R_{13}$, and $R_{14}$ are each independently —H, —$(C_1$-$C_4)$alkyl, —$(C_2$-$C_4)$alkenyl, —$(C_2$-$C_4)$alkynyl, —$OR_7$, —$SR_7$, —$C(halo)_3$, —$CH(halo)_2$, —$CH_2(halo)$, —CN, -halo, —$N_3$, —$NO_2$, —$N(R_7)_2$, —$N(R_7)OH$, —$C(=O)R_7$, —$C(=O)N(R_7)_2$, —$C(=O)OR_7$, —$OC(=O)R_7$, —$S(=O)R_7$, or —$S(=O)_2R_7$;

the dashed lines between $R_{13}'$ and $R_{14}'$ and $R_{14}'$ and $R_{15}'$ each denote the presence or absence of a bond, wherein:

(a) $R_{13}'$, $R_{14}'$ and $R_{15}'$ are each present if both bonds are absent; or (b) $R_{13}'$ and $R_{14}'$ are each absent and $R_{15}'$ is present if the bond between $R_{13}'$ and $R_{14}'$ is present and the bond between $R_{14}'$ and $R_{15}'$ is absent; or (c) $R_{13}'$ is present and $R_{14}'$ and $R_{15}'$ are absent if the bond between $R_{13}'$ and $R_{14}'$ is absent and the bond between $R_{14}'$ and $R_{15}'$ is present;

$R_{13}'$, $R_{14}'$, and $R_{15}'$, if present, are each independently —H or —$(C_1$-$C_3)$alkyl; and a is 1 or 2; wherein:

(a) if a is 1, the ring denoted as Q is —$(C_5)$cycloalkyl, or —$(C_5)$cycloalkenyl, each of which is unsubstituted or substituted with 1, 2 or 3 independently selected $R_5$ groups;

(b) if a is 2, the ring denoted as Q is —$(C_6)$cycloalkyl, or —$(C_6)$cycloalkenyl, each of which is unsubstituted or substituted with 1, 2 or 3 independently selected $R_5$ groups;

$R_2$ and $R_3$ are each independently -halo, —CN, —$NO_2$, -$OT_3$, —$OC(=O)T_3$, —$C(=O)T_3$, —$C(=O)OT_3$, —$C(=O)N(T_1)(T_2)$, —$(C_1$-$C_3)$alkyl, —$(C_2$-$C_3)$alkenyl, —$(C_2$-$C_3)$alkynyl, or —$(C_1$-$C_3)$alkoxy, wherein the —$(C_1$-$C_3)$alkyl, —$(C_2$-$C_3)$alkenyl, —$(C_2$-$C_3)$alkynyl, and —$(C_1$-$C_3)$alkoxy are each unsubstituted or substituted with 1 or 2 independently selected $R_5$ groups;

each $R_5$ is independently —H, —$(C_1$-$C_3)$alkyl, —$(C_3)$alkenyl, —$(C_3)$alkynyl, —$OR_7$, —$C(halo)_3$, —$CH(halo)_2$, —$CH_2(halo)$, —CN, -halo, —$N_3$, —$NO_2$, —$N(R_7)_2$, —$N(R_7)OH$, —$C(=O)R_7$, or —$C(=O)OR_7$;

each $R_7$ is independently —H, or —$CH_3$;

each $T_1$, $T_2$, and $T_3$ is independently —H or —$CH_3$; and each halo is independently —F, —Cl, —Br, or —I.

25. The personal-care composition of claim 24, wherein the compound of Formula I.2.1 is:

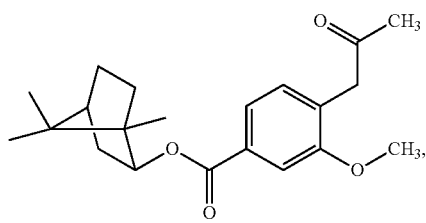 [SMILES: COc1cc(C(=O)OC2CC3CCC2(C)C3(C)C)ccc1CC(C)=O]

or a pharmaceutically acceptable derivative thereof.

26. The personal-care composition of claim 24, wherein the personal-care product is a cosmetic product or a wound dressing.

27. The personal-care composition of claim 26, wherein the personal-care composition is a cosmetic product, wherein the cosmetic product is an oral hygiene composition, a skin care composition, or a hair care composition.

28. The personal-care composition of claim 26, wherein the personal-care composition is a cosmetic product, wherein the cosmetic product is an insect repellent, a lotion, a shaving cream, a post-shaving preparation, a shampoo, a conditioner, a facial cleanser, a soap, a bath oil, a bath foam, an antiperspirant, a deodorant, a toothpaste, a mouthwash, a dental floss, a chewing gum, or a breath freshener.

29. The personal-care composition of claim 24, wherein the personal-care agent is an emulsifier, a detergent, a preservative, an anti-aging compound, a depilation agent, or a peeling agent.

\* \* \* \* \*

UNITED STATES PATENT AND TRADEMARK OFFICE
CERTIFICATE OF CORRECTION

Page 1 of 2

PATENT NO. : 9,440,993 B2
APPLICATION NO. : 14/116832
DATED : September 13, 2016
INVENTOR(S) : Michael Krohn et al.

It is certified that error appears in the above-identified patent and that said Letters Patent is hereby corrected as shown below:

In the Claims

At Column 87, Claim number 2, Line number 30, please replace:

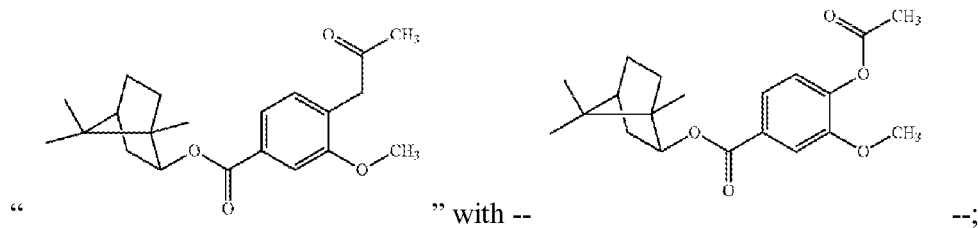

" with -- --;

At Column 90, Claim number 9, Line number 30, please replace:

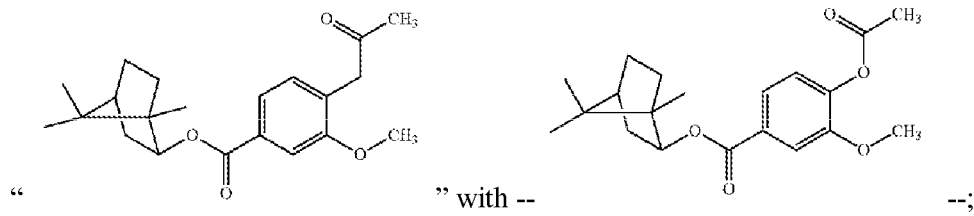

" with -- --;

At Column 93, Claim number 16, Line number 22, please replace:

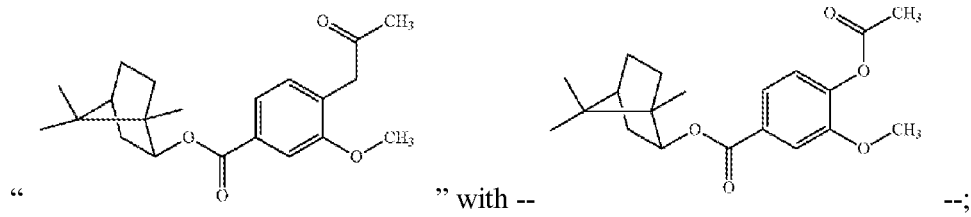

" with -- --;

Signed and Sealed this
Eighth Day of August, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,440,993 B2

At Column 96, Claim number 18, Line number 1, please replace:

" 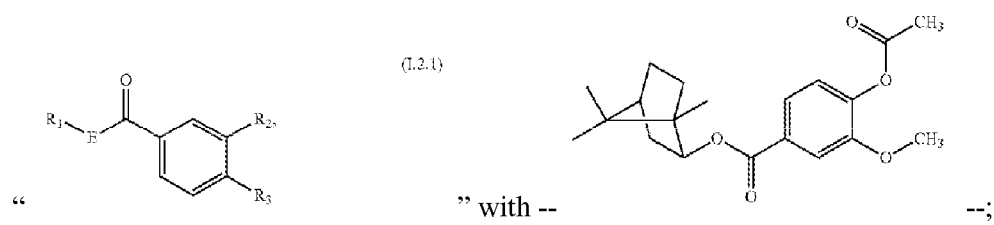 " with -- --;

At Column 99, Claim number 25, Line number 1, please replace:

" 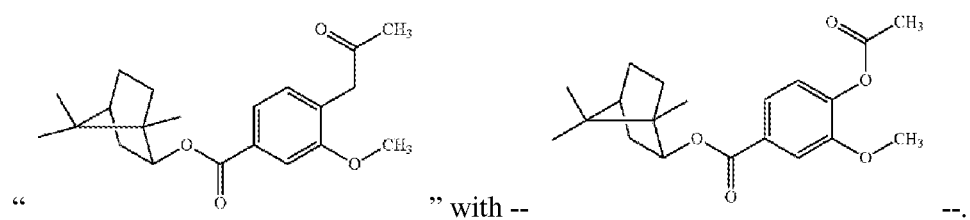 " with -- --.